United States Patent
Wu et al.

(10) Patent No.: US 11,633,379 B2
(45) Date of Patent: Apr. 25, 2023

(54) METHODS OF INHIBITING PCSK9

(71) Applicants: TRUSTEES OF DARTMOUTH COLLEGE, Hanover, NH (US); Oregon Health & Science University, Portland, OR (US)

(72) Inventors: Jimmy Wu, Hanover, NH (US); Sergio Fazio, Portland, OR (US); Hagai Tavori, Portland, OR (US)

(73) Assignees: Trustees of Dartmouth College, Hanover, NH (US); Oregon Health & Science University, Portland, OR (US)

( * ) Notice: Subject to any disclaimer, the term of this patent is extended or adjusted under 35 U.S.C. 154(b) by 873 days.

(21) Appl. No.: 16/475,553

(22) PCT Filed: Jan. 4, 2018

(86) PCT No.: PCT/US2018/012411
§ 371 (c)(1),
(2) Date: Jul. 2, 2019

(87) PCT Pub. No.: WO2018/129205
PCT Pub. Date: Jul. 12, 2018

(65) Prior Publication Data
US 2019/0336480 A1    Nov. 7, 2019

Related U.S. Application Data

(60) Provisional application No. 62/442,196, filed on Jan. 4, 2017.

(51) Int. Cl.
*A61K 31/404*    (2006.01)
*A61P 3/06*    (2006.01)
(Continued)

(52) U.S. Cl.
CPC .......... *A61K 31/404* (2013.01); *A61K 9/0053* (2013.01); *A61K 31/407* (2013.01); *A61K 31/475* (2013.01); *A61P 3/06* (2018.01)

(58) Field of Classification Search
CPC ................ A61K 31/404; A61K 31/407; A61K 31/4748; A61K 31/475; A61K 9/0053;
(Continued)

(56) References Cited

U.S. PATENT DOCUMENTS

| | | |
|---|---|---|
| 5,489,611 A | 2/1996 | Lee et al. |
| 5,635,516 A | 6/1997 | Caubere et al. |

(Continued)

FOREIGN PATENT DOCUMENTS

| | | |
|---|---|---|
| WO | WO 2004/063156 | 7/2004 |
| WO | WO 2016/100711 | 6/2016 |

OTHER PUBLICATIONS

International Preliminary Report on Patentability in PCT/US2018/012411 dated Jul. 9, 2019.

(Continued)

*Primary Examiner* — Savitha M Rao
(74) *Attorney, Agent, or Firm* — Neal, Gerber & Eisenberg LLP; Kevin A. O'Connor

(57) ABSTRACT

Provided herein are methods for inhibiting PCSK9, reducing PCSK9 levels, and for treating or preventing related conditions and disorders, in a subject, which includes administering to a subject an effective amount of a compound which includes derivatized cycloalkyl[b]indoles, e.g., cyclopenta-, cyclohexa- and cyclohepta[b]indoles.

8 Claims, 17 Drawing Sheets

(51) Int. Cl.
*A61K 9/00* (2006.01)
*A61K 31/407* (2006.01)
*A61K 31/475* (2006.01)

(58) Field of Classification Search
CPC ....... A61P 3/06; C07D 209/80; C07D 209/86; C07D 209/94; C07D 405/04; C07D 409/04
See application file for complete search history.

(56) References Cited

U.S. PATENT DOCUMENTS

| | | | |
|---|---|---|---|
| 9,598,365 B2 | 3/2017 | Wu | |
| 2015/0057326 A1* | 2/2015 | Wu | C07D 209/94 548/425 |

OTHER PUBLICATIONS

International Search Report in PCT/US2018/012411 dated Mar. 20, 2018.
Mitchell et al. "Pharmacologic Profile of the Adnectin BMS-962476, a Small Protein Biologic Alternative to PCSK9 Antibodies for Low-Density Lipoprotein Lowering," The Journal of Pharmcology and Experimental Therapeutics, 2014, vol. 350, pp. 412-424.
Zhang et al. An Anti-PCSK9 Antibody Reduces LDL-Cholesterol On Top Of A Stain And Suppresses Hepatocyte SREBP-Regulated Genes, International Journal of Biological Sciences, 2012, vol. 8, pp. 310-327, abstract; p. 321, col. 2, para 2 to p. 322, col. 1, para 1.

* cited by examiner

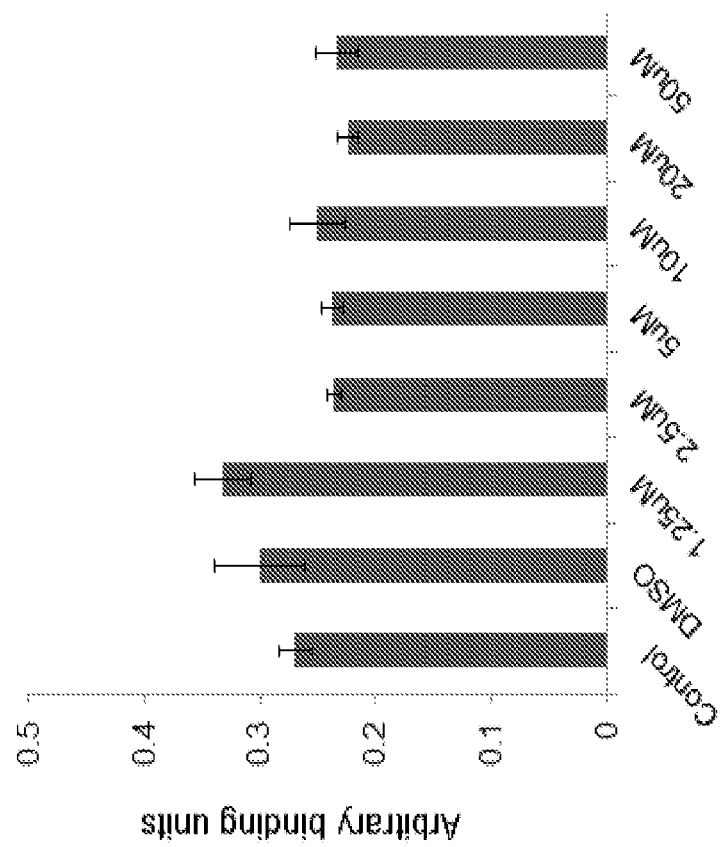
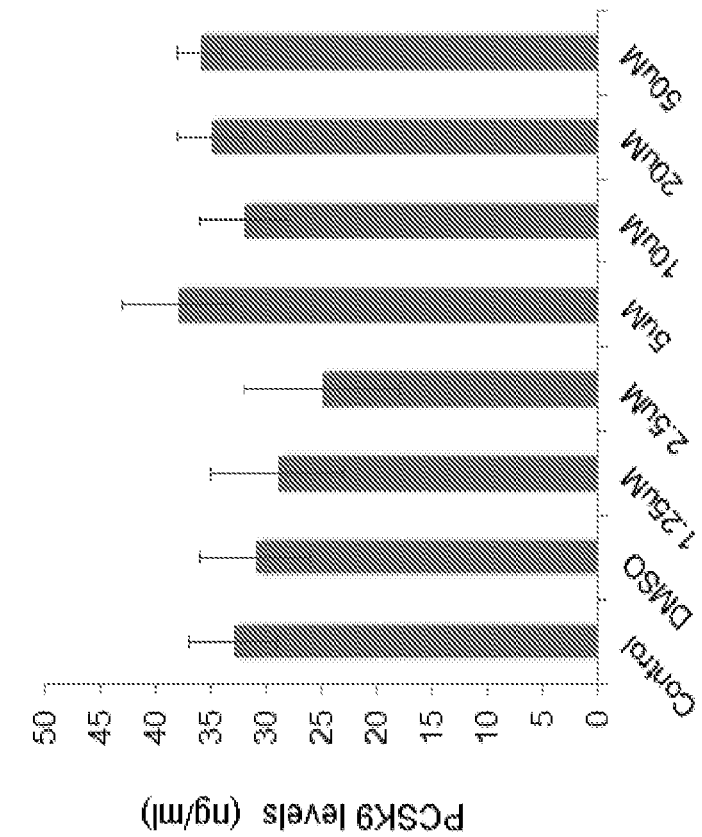
Figure 5A
Figure 5B

METHODS OF INHIBITING PCSK9

CROSS-REFERENCE TO RELATED APPLICATIONS

This application is a National Stage Entry of International Application Number PCT/US2018/012411, which was filed on Jan. 4, 2018 and claims the benefit of and priority to U.S. Provisional Patent Application No. 62/442,196, filed Jan. 4, 2017. The contents of each of the aforementioned applications are incorporated herein by reference in their entireties.

BACKGROUND

Proprotein convertase subtilisin/kexin type 9 (PCSK9), also known as neural apoptosis-regulated convertase (NARC-1), is a proteinase K-like subtilase identified as the ninth member of the secretory subtilase family. PCSK9 is a natural inhibitor of LDL receptor (LDLR) and plays a critical role in cholesterol metabolism. PCSK9 binds the extracellular domain of LDLR and triggers its intracellular degradation, thereby controlling the levels of LDL particles that circulate in the bloodstream. Elevated levels of PCSK9 have been shown to reduce the levels of LDLR in the liver, resulting in increased levels of LDL-cholesterol in the plasma and increased susceptibility to diseases or conditions associated with an elevated level of LDL-cholesterol. As such, there is a need for inhibitors of PCSK9. Currently, the only FDA approved inhibitors of PCSK9 are monoclonal antibodies, and PCSK9 inhibitors currently in clinical trials are biologics, including monoclonal antibodies and oligonucleotides.

SUMMARY

In one aspect, provided herein is a method for reducing the PCSK9 level in a subject, the method comprising administering to the subject an effective amount of a compound of Formula I, or a pharmaceutically acceptable stereoisomer, isotope, solvate or salt thereof:

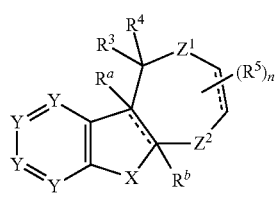

(I)

wherein dashed bonds, independently, are present or absent;

X is O, S, $CR_2$ or $NR^1$;

Y is, for each occurrence, independently N or $C(R_6)$;

$Z^1$ is $CH_2$, $CH(R^5)$, $C(R^5)_2$ or is absent;

$Z^2$ is $CH_2$, $CH(R^5)$, $C(R^5)_2$, $NR_2$ or is absent;

$R^a$ and $R^b$ are absent, or independently selected from hydrogen, alkyl, hydroxyl, and amino; wherein $R_a$ and $R_b$ may combine to form a 5- or 6-membered ring;

$R^1$ is hydrogen, alkyl, alkenyl, alkynyl or aryl;

$R^2$ is, for each occurrence, independently selected from the group consisting of hydrogen, halogen, haloalkyl, alkyl, alkoxy, alkenyl, alkynyl, cycloalkyl, cycloalkenyl, —$R^7$-cycloalkyl, aryl, —$NHR^7$, Het, —NHHet, —$NHR^7$Het, —$OR^8$, —O-aryl, —OHet, —$R^7OR^8$, —$NR^8R^9$, —$NR^8$-aryl, —$R^7NR^8R^9$, —$R^7NR^8$-aryl, —$R^7C(O)R^8$, —$C(O)R^8$, —$CO_2R^8$, —$R^7CO_2R^8$, —$C(O)NR^8R^9$, —$C(O)aryl$, —$C(O)NR^8aryl$, —$C(O)Het$, —$C(O)NHR^7Het$, —$R^7C(O)NR^8R^9$, —$C(S)NR^8R^9$, —$R^7C(S)NR^8R^9$, —$R^7(NH)NR^8R^9$, —$C(NH)NR^8R^9$, —$R^7C(NH)NR^8R^9$, —$S(O)_2NR^8R^9$, —$S(O)_2NR^8aryl$, —$R^7SO_2NHCOR^8$, —$R^7SO_2NR^8R^9$, —$R^7SO_2R^8$, —$S(O)_mR^8$, cyano, nitro, and azido;

$R^3$ is selected from the group consisting of hydrogen, halogen, haloalkyl, alkyl, alkoxy, alkenyl, alkynyl, cycloalkyl, cycloalkenyl, Het, aryl, —$NHR^7$, —NHHet, —$NHR^7$Het, —$OR^8$, —O-aryl, —OHet, —$R^7OR^8$, —$NR^8R^9$, —$NR^8$-aryl, —$R^7NR^8R^9$, —$R^7NR^8$-aryl, —$R^7C(O)R^8$, —$C(O)R^8$, —$CO_2R^8$, —$R^7CO_2R^8$, —$C(O)NR^8R^9$, —$C(O)aryl$, —$C(O)NR^8aryl$, —$C(O)Het$, —$C(O)NHR^7Het$, —$R^7C(O)NR^8R^9$, —$C(S)NR^8R^9$, —$R^7C(S)NR^8R^9$, —$R^7(NH)NR^8R^9$, —$C(NH)NR^8R^9$, —$R^7C(NH)NR^8R^9$, —$S(O)_2NR^8R^9$, —$S(O)_2NR^8aryl$, —$R^7SO_2NHCOR^8$, —$R^7SO_2NR^8R^9$, —$R^7SO_2R^8$, —$S(O)_mR^8$, cyano, nitro, and azido;

$R^4$ is selected from the group consisting of hydrogen, halogen, haloalkyl, alkyl, alkoxy, alkenyl, alkynyl, cycloalkyl, cycloalkenyl, Het, aryl, —$NHR^7$, —NHHet, —$NHR^7$Het, —$OR^8$, —O-aryl, —OHet, —$R^7OR^8$, —$NR^8R^9$, —$NR^8$-aryl, —$R^7NR^8R^9$, —$R^7NR^8$-aryl, —$R^7C(O)R^8$, —$C(O)R^8$, —$CO_2R^8$, —$R^7CO_2R^8$, —$C(O)NR^8R^9$, —$C(O)aryl$, —$C(O)NR^8aryl$, —$C(O)Het$, —$C(O)NHR^7Het$, —$R^7C(O)NR^8R^9$, —$C(S)NR^8R^9$, —$R^7C(S)NR^8R^9$, —$R^7(NH)NR^8R^9$, —$C(NH)NR^8R^9$, —$R^7C(NH)NR^8R^9$, —$S(O)_2NR^8R^9$, —$S(O)_2NR^8aryl$, —$R^7SO_2NHCOR^8$, —$R^7SO_2NR^8R^9$, —$R^7SO_2R^8$, —$S(O)_mR^8$, cyano, nitro, and azido;

$R^5$ is, for each occurrence, independently selected from the group consisting of halogen, haloalkyl, alkyl, alkoxy, alkenyl, alkynyl, cycloalkyl, cycloalkenyl, Het, aryl, —$NHR^7$, —NHHet, —$NHR^7$Het, oxo, —$OR^8$, —O-aryl, —OHet, —$R^7OR^8$, —$NR^8R^9$, —$NR^8$-aryl, —$R^7NR^8R^9$, —$R^7NR^8$-aryl, —$R^7C(O)R^8$, —$C(O)R^8$, —$CO_2R^8$, —$R^7CO_2R^8$, —$C(O)NR^8R^9$, —$C(O)aryl$, —$C(O)NR^8aryl$, —$C(O)Het$, —$C(O)NHR^7Het$, —$R^7C(O)NR^8R^9$, —$C(S)NR^8R^9$, —$R^7C(S)NR^8R^9$, —$R^7(NH)NR^8R^9$, —$C(NH)NR^8R^9$, —$R^7C(NH)NR^8R^9$, —$S(O)_2NR^8R^9$, —$S(O)_2NR^8aryl$, —$R^7SO_2NHCOR^8$, —$R^7SO_2NR^8R^9$, —$R^7SO_2R^8$, —$S(O)_mR^8$, cyano, nitro, and azido;

$R^6$ is, for each occurrence, independently selected from hydrogen, halogen, haloalkyl, alkyl, alkoxy, alkenyl, alkynyl, cycloalkyl, cycloalkenyl, —$R^7$-cycloalkyl, aryl, —$NHR^7$, Het, —NHHet, —$NHR^7$Het, —$OR^8$, —O-aryl, —OHet, —$R^7OR^8$, —$NR^8R^9$, —$NR^8$-aryl, —$R^7NR^8R^9$, —$R^7NR^8$-aryl, —$R^7C(O)R^8$, —$C(O)R^8$, —$CO_2R^8$, —$R^7CO_2R^8$, —$C(O)NR^8R^9$, —$C(O)aryl$, —$C(O)NR^8aryl$, —$C(O)Het$, —$C(O)NHR^7Het$, —$R^7C(O)NR^8R^9$, —$C(S)NR^8R^9$, —$R^7C(S)NR^8R^9$, —$R^7(NH)NR^8R^9$, —$C(NH)NR^8R^9$, —$R^7C(NH)NR^8R^9$, —$S(O)_2NR^8R^9$, —$S(O)_2NR^8aryl$, —$R^7SO_2NHCOR^8$, —$R^7SO_2NR^8R^9$, —$R^7SO_2R^8$, —$S(O)_mR^8$, cyano, nitro, and azido;

$R^7$ is independently selected from an alkyl, cycloalkyl alkenyl, cycloalkenyl and alkynyl $R^8$ is independently selected from the group of hydrogen, an alkyl, alkoxy, alkenyl, alkynyl, cycloalkyl, cycloalkenyl, —$R^7$cycloalkyl, —$R^7$OH, —$R^7(OR^7)_w$, and —$R^7NR^{10}R^{11}$ group;

$R^9$ is independently selected from the group of hydrogen, an alkyl, alkoxy, alkenyl, alkynyl, cycloalkyl, cycloalkenyl, —$R^7$cycloalkyl, —$R^7$OH, —$R^7(OR^7)_w$, and —$R^7NR^{10}R^{11}$ group;

$R^{10}$ and $R^{11}$ are the same or different and are independently selected from the group of alkyl, cycloalkyl, alkenyl, cycloalkenyl, and alkynyl;

m, for each occurrence, independently is 0, 1 or 2;
n is 0, 1, 2, 3, 4, 5 or 6;
w is an integer selected from 1-10; and
wherein any two of $R^2$, $R^3$, $R^4$ and $R^5$, or two $R^5$, may combine to form a 5- or 6-membered ring.

In some embodiments, provided herein is a method for reducing the PCSK9 level in a subject, the method comprising administering to the subject an effective amount of a compound of Formula II, III, or IV, or a pharmaceutically acceptable stereoisomer, isotope, solvate or salt thereof:

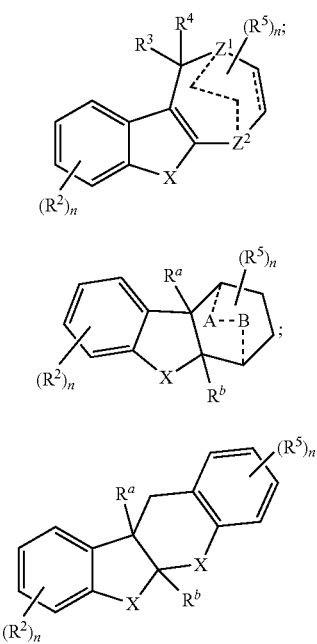

wherein dashed bonds, independently, be present or absent;

A and B are independently O, $NR^1$, $CH_2$, $CH(R^5)$, $C(R^5)_2$, or are absent;

X is $NR^1$;

$Z^1$ is $CH_2$, $CH(R^5)$, $C(R^5)_2$ or is absent;

$Z^2$ is $CH_2$, $CH(R^5)$, $C(R^5)_2$, or is absent; or wherein $Z^1$ and $Z^2$ together form a C:1-3 carbocyclic bridge;

$R^a$ and $R^b$ are absent, or are independently selected from hydrogen, alkyl, hydroxyl, hydroxyalkyl, aryl, benzyl, and amino; or wherein $R^a$ and $R^b$ together a 5- or 6-membered cycloalkyl or heterocycloalkyl with one or more heteroatoms independently selected from O or $NR^1$;

$R^1$ is hydrogen, alkyl, alkenyl, alkynyl, aryl, benzyl, or alkylene optionally substituted with aryl;

$R^2$ is, for each occurrence, independently selected from the group consisting of hydrogen, halogen, haloalkyl, alkyl, alkoxy, alkenyl, alkynyl, cycloalkyl, cycloalkenyl, —$R^7$-cycloalkyl, aryl, —$NHR^7$, Het, —NHHet, —$NHR^7$Het, —$OR^8$, —O-aryl, —OHet, —$R^7OR^8$, —$NR^8R^9$, —$NR^8$-aryl, —$R^7NR^8R^9$, —$R^7NR^8$-aryl, —$R^7C(O)R^8$, —$C(O)R^8$, —$CO_2R^8$, —$R^7CO_2R^8$, —$C(O)NR^8R^9$, —C(O)aryl, —$C(O)NR^8$aryl, —C(O)Het, —$C(O)NHR^7$Het, —$R^7C(O)NR^8R^9$, —$C(S)NR^8R^9$, —$R^7C(S)NR^8R^9$, —$R^7(NH)NR^8R^9$, —$C(NH)NR^8R^9$, —$R^7C(NH)NR^8R^9$, —$S(O)_2NR^8R^9$, —$S(O)_2NR^8$aryl, —$R^7SO_2NHCOR^8$, —$R^7SO_2NR^8R^9$, —$R^7SO_2R^8$, —$S(O)_mR^8$, cyano, nitro, and azido;

$R^3$ is selected from the group consisting of hydrogen, halogen, haloalkyl, alkyl, alkoxy, alkenyl, alkynyl, cycloalkyl, cycloalkenyl, Het, aryl, —$NHR^7$, —NHHet, —$R^7$Het, —$NHR^7$Het, —$OR^8$, —O-aryl, —OHet, —$R^7OR^8$, —$NR^8R^9$, —$NR^8$-aryl, —$R^7NR^8R^9$, —$R^7R^8$-aryl, —$R^7C(O)R^8$, —$C(O)R^8$, —$CO_2R^8$, —$R^7CO_2R^8$, —$C(O)NR^8R^9$, —C(O)aryl, —$C(O)NR^8$aryl, —C(O)Het, —C(O)NHR^7Het, —$R^7C(O)NR^8R^9$, —$C(S)NR^8R^9$, —$R^7C(S)NR^8R^9$, —$R^7(NH)NR^8R^9$, —$C(NH)NR^8R^9$, —$R^7C(NH)NR^8R^9$, —$S(O)_2NR^8R^9$, —$S(O)_2NR^8$aryl, —$R^7SO_2NHCOR^8$, —$R^7SO_2NR^8R^9$, —$R^7SO_2R^8$, —$S(O)_mR^8$, cyano, nitro, and azido;

$R^4$ is selected from the group consisting of hydrogen, halogen, haloalkyl, alkyl, alkoxy, alkenyl, alkynyl, cycloalkyl, cycloalkenyl, Het, aryl, —$NHR^7$, —NHHet, —$R^7$Het-$NHR^7$Het, —$OR^8$, —O-aryl, —OHet, —$R^7OR^8$, —$NR^8R^9$, —$NR^8$-aryl, —$R^7NR^8R^9$, —$R^7R^8$-aryl, —$R^7C(O)R^8$, —$C(O)R^8$, —$CO_2R^8$, —$R^7CO_2R^8$, —$C(O)NR^8R^9$, —C(O)aryl, —$C(O)NR^8$aryl, —C(O)Het, —$C(O)NHR^7$Het, —$R^7C(O)NR^8R^9$, —$C(S)NR^8R^9$, —$R^7C(S)NR^8R^9$, —$R^7(NH)NR^8R^9$, —$C(NH)NR^8R^9$, —$R^7C(NH)NR^8R^9$, —$S(O)_2NR^8R^9$, —$S(O)_2NR^8$aryl, —$R^7SO_2NHCOR^8$, —$R^7SO_2NR^8R^9$, —$R^7SO_2R^8$, —$S(O)_mR^8$, cyano, nitro, and azido;

or, $R^3$ and $R^4$ together may combine to form a 4, 5, or 6 member cycloalkyl, aryl, or Het;

$R^5$ is, for each occurrence, independently selected from the group consisting of hydrogen, halogen, haloalkyl, alkyl, alkoxy, alkenyl, alkynyl, cycloalkyl, cycloalkenyl, Het, aryl, substituted aryl, —$NHR^7$, —NHHet, —$NHR^7$Het, oxo, —$OR^8$, —O-aryl, —OHet, —$R^7OR^8$, —$NR^8R^9$, —$NR^8$-aryl, —$R^7NR^8R^9$, —$R^7R^8$-aryl, —$R^7C(O)R^8$, —$C(O)R^8$, —$CO_2R^8$, —$R^7CO_2R^8$, —$C(O)NR^8R^9$, —C(O)aryl, —$C(O)NR^8$aryl, —C(O)Het, —$C(O)NHR^7$Het, —$R^7C(O)NR^8R^9$, —$C(S)NR^8R^9$, —$R^7C(S)NR^8R^9$, —$R^7(NH)NR^8R^9$, —$C(NH)NR^8R^9$, —$R^7C(NH)NR^8R^9$, —$S(O)_2NR^8R^9$, —$S(O)_2NR^8$aryl, —$R^7SO_2NHCOR^8$, —$R^7SO_2NR^8R^9$, —$R^7SO_2R^8$, —$S(O)_mR^8$, cyano, nitro, and azido;

$R^7$ is independently selected from an alkyl, cycloalkyl alkenyl, cycloalkenyl and alkynyl;

$R^8$ is independently selected from the group of hydrogen, an alkyl, alkoxy, alkenyl, alkynyl, cycloalkyl, cycloalkenyl, —$R^7$cycloalkyl, —$R^7OH$, —$R^7(OR^7)_w$, and —$R^7NR^{10}R^{11}$ group;

$R^9$ is independently selected from the group of hydrogen, an alkyl, alkoxy, alkenyl, alkynyl, cycloalkyl, cycloalkenyl, —$R^7$cycloalkyl, —$R^7OH$, —$R^7(OR^7)_w$, and —$R^7NR^{10}R^{11}$ group;

$R^{13}$ and $R^{11}$ are the same or different and are independently selected from the group of alkyl, cycloalkyl, alkenyl, cycloalkenyl, and alkynyl;

m, for each occurrence, independently is 0, 1 or 2;

n, for each occurrence, independently is 0, 1, 2, 3, 4, 5 or 6; and wherein any two of $R^2$, $R^3$, $R^4$ and $R^5$, or two $R^5$, may combine to form a 5- or 6-membered ring.

In an embodiment, the PCSK9 level is reduced by at least 10%, 20%, 30%, 40%, 50%, 60%, 70%, or 80% compared to the PCSK9 level in the subject prior to administering the compound of Formula I. In an embodiment, levels of both the pro-protein and mature forms of PCSK9 are reduced. In an embodiment, the secretion of PCSK9 is inhibited. In an embodiment, the production of PCSK9 is inhibited.

In an embodiment, the level of low density lipoprotein receptor (LDLR) in the subject is increased. In an embodiment, the amount of low density lipoprotein (LDL) in the cell is decreased.

In another aspect, provided herein is a method of treating or preventing a condition associated with an elevated level of LDL, the method comprising administering to a subject in need of such treatment an effective amount of a compound of Formula I. In an embodiment, the compound of Formula I is administered orally. In an embodiment, the level of LDL in the subject is reduced. In an embodiment, the PCSK9 level in the subject is reduced. In an embodiment, the hepatic level of LDLR in the subject is increased.

In an embodiment, the condition associated with an elevated level of LDL is selected from the group consisting of hypercholesterolemia, hyperlipidemia, dyslipidemia, metabolic syndrome, a diabetic condition, heart disease, cardiovascular disease, an atherosclerotic disease, stroke and Alzheimer's disease.

In an embodiment, the method further comprises administering one or more of additional active agents. In an embodiment, the additional active agent is selected from the group consisting of a statin, ACE inhibitor, Angiotensin II receptor blocker (ARB), antiarrhythmic agent, antiplatelet agent, anti-clotting agent, anti-cholesterol agent, anti-diabetic agent, diuretic, vasodilator, blood thinner, beta blocker, amiodarone, digoxin, and aspirin.

In an embodiment, the compound of Formula I or Formula II has the structure of Formula IIa:

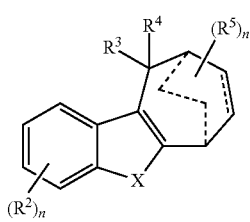

(IIa)

wherein dashed bonds, independently, may be present or absent;

X is NR$^1$;

R$^a$ and R$^b$ are absent, or independently selected from hydrogen, alkyl, hydroxyl, and hydroxyalkyl;

R$^1$ is hydrogen, alkyl, alkenyl, alkynyl aryl, benzyl, or alkylene optionally substituted with aryl;

R$^2$ is, for each occurrence, independently selected from the group consisting of hydrogen, halogen, haloalkyl, alkyl, alkoxy, alkenyl, alkynyl, cycloalkyl, cycloalkenyl, and —CO$_2$R$^8$;

R$^3$ is selected from the group consisting of hydrogen, halogen, haloalkyl, alkyl, alkoxy, alkenyl, alkynyl, cycloalkyl, cycloalkenyl, Het, —CO$_2$R$^8$, aryl, and aryl substituted with alkoxy or haloalkyl;

R$^4$ is selected from the group consisting of hydrogen, halogen, haloalkyl, alkyl, alkoxy, alkenyl, alkynyl, cycloalkyl, cycloalkenyl, Het, —CO$_2$R$^8$, aryl, and aryl substituted with alkoxy or haloalkyl;

or, R$^3$ and R$^4$ together may combine to form a 4, 5, or 6 member cycloalkyl;

R$^5$ is, for each occurrence, independently selected from the group consisting of hydrogen, halogen, haloalkyl, alkyl, alkoxy, alkenyl, alkynyl, cycloalkyl, oxo, cycloalkenyl, Het, aryl, substituted aryl; and wherein n is 0, 1, 2, 3, or 4.

In an embodiment, the compound of Formula IIa has a structure selected from the following:

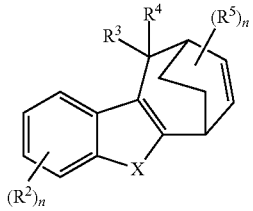

(IIa$^1$)

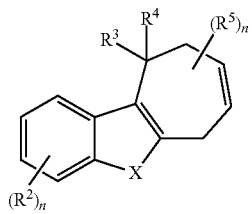

(IIa$^2$)

wherein, X is NR$^1$;

R$^1$ is hydrogen, alkyl, alkenyl, alkynyl, aryl, benzyl, or alkylene optionally substituted with aryl;

R$^2$ is, for each occurrence, independently selected from the group consisting of hydrogen, halogen, haloalkyl, alkyl, alkoxy, alkenyl, alkynyl, cycloalkyl, cycloalkenyl, and —CO$_2$R$^8$;

R$^3$ is selected from the group consisting of hydrogen, halogen, haloalkyl, alkyl, alkoxy, alkenyl, alkynyl, cycloalkyl, cycloalkenyl, Het, —CO$_2$R$^8$, aryl; aryl substituted with alkoxy, haloalkyl;

R$^4$ is selected from the group consisting of hydrogen, halogen, haloalkyl, alkyl, alkoxy, alkenyl, alkynyl, cycloalkyl, cycloalkenyl, Het, —CO$_2$R$^8$, aryl; aryl substituted with alkoxy, haloalkyl;

or, R$^3$ and R$^4$ together may combine to form a 4, 5, or 6 member cycloalkyl;

R$^5$ is, for each occurrence, independently selected from the group consisting of hydrogen, halogen, haloalkyl, alkyl, alkoxy, alkenyl, alkynyl, cycloalkyl, cycloalkenyl, Het, aryl, substituted aryl, oxo; and wherein n is 0, 1, 2, 3, or 4.

In an embodiment, the compound of Formula I or II has the structure of Formula IIb:

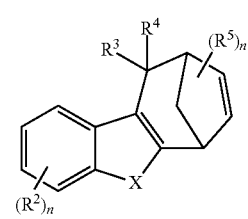

(IIb)

wherein X is NR$^1$;

R$^1$ is hydrogen, alkyl, alkenyl, alkynyl, aryl, benzyl, or alkylene optionally substituted with aryl;

R$^2$ is, for each occurrence, independently selected from the group consisting of hydrogen, halogen, haloalkyl, alkyl, alkoxy, alkenyl, alkynyl, cycloalkyl, cycloalkenyl, and —CO$_2$R$^8$;

R³ is selected from the group consisting of hydrogen, halogen, haloalkyl, alkyl, alkoxy, alkenyl, alkynyl, cycloalkyl, cycloalkenyl, Het, —CO₂R⁸, aryl; aryl substituted to with alkoxy, haloalkyl;

R⁴ is selected from the group consisting of hydrogen, halogen, haloalkyl, alkyl, alkoxy, alkenyl, alkynyl, cycloalkyl, cycloalkenyl, Het, —CO₂R⁸, aryl; aryl substituted with alkoxy, haloalkyl;

or, R³ and R⁴ together may combine to form a 4, 5, or 6 member cycloalkyl;

R⁵ is, for each occurrence, independently selected from the group consisting of hydrogen, halogen, haloalkyl, alkyl, alkoxy, alkenyl, alkynyl, cycloalkyl, cycloalkenyl, Het, aryl, substituted aryl, and oxo; and n is 0, 1, 2, 3 or 4.

In an embodiment, the compound of Formula IIb is selected from compounds IIb¹ and IIb²:

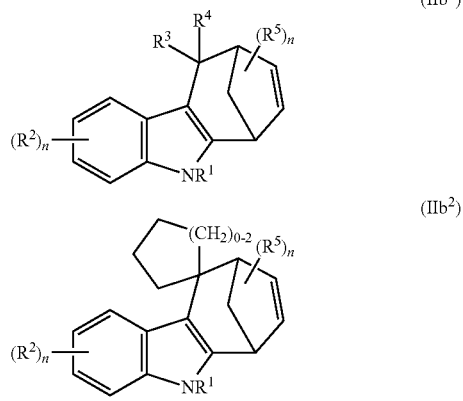

wherein R¹ is hydrogen, alkyl, alkenyl, alkynyl, aryl, benzyl, or alkylene optionally substituted with aryl;

R² is, for each occurrence, independently selected from the group consisting of hydrogen, halogen, haloalkyl, alkyl, alkoxy, alkenyl, alkynyl, cycloalkyl, cycloalkenyl, and —CO₂R⁸;

R³ is selected from the group consisting of hydrogen, halogen, haloalkyl, alkyl, alkoxy, alkenyl, alkynyl, cycloalkyl, cycloalkenyl, Het, —CO₂R⁸, aryl; aryl substituted with alkoxy, haloalkyl;

R⁴ is selected from the group consisting of hydrogen, halogen, haloalkyl, alkyl, alkoxy, alkenyl, alkynyl, cycloalkyl, cycloalkenyl, Het, —CO₂R⁸, aryl; aryl substituted with alkoxy, haloalkyl;

R⁵ is, for each occurrence, independently selected from the group consisting of hydrogen, halogen, haloalkyl, alkyl, alkoxy, oxo, alkenyl, alkynyl, cycloalkyl, cycloalkenyl, Het, aryl, substituted aryl, oxo, and wherein n is 0, 1, 2, 3 or 4.

In an embodiment, the compound of Formula I or Formula II has the structure of Formula IIc¹:

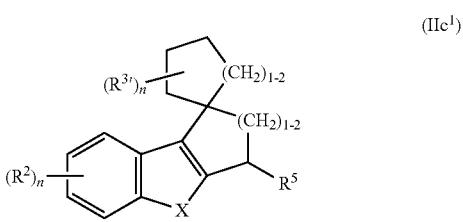

wherein X is NR¹;

R¹ is hydrogen, alkyl, alkenyl, alkynyl, aryl, benzyl, or alkylene optionally substituted with aryl;

R² is, for each occurrence, independently selected from the group consisting of hydrogen, halogen, haloalkyl, alkyl, alkoxy, alkenyl, alkynyl, cycloalkyl, cycloalkenyl, and —CO₂R⁸;

R³' is, for each occurrence, independently selected from the group consisting of hydrogen, halogen, haloalkyl, alkyl, alkoxy, alkenyl, alkynyl, cycloalkyl, cycloalkenyl, Het, aryl, —NHR⁷, —NHHet, —NHR⁷Het, oxo, —OR⁸, —O-aryl, —OHet, —R⁷OR⁸, —NR⁸R⁹, —NR⁸-aryl, —R⁷NR⁸R⁹, —R⁷NR⁸-aryl, —R⁷C(O)R⁸, —C(O)R⁸, —CO₂R⁸, —R⁷CO₂R⁸, —C(O)NR⁸R⁹, —C(O)aryl, —C(O)NR⁸aryl, —C(O)Het, —C(O)NHR⁷Het, —R⁷C(O)NR⁸R⁹, —C(S)NR⁸R⁹, —R⁷C(S)NR⁸R⁹, —R⁷(NH)NR⁸R⁹, —C(NH)NR⁸R⁹, —R⁷C(NH)NR⁸R⁹, —S(O)₂NR⁸R⁹, —S(O)₂NR⁸aryl, —R⁷SO₂NHCOR⁸, —R⁷SO₂NR⁸R⁹, —R⁷SO₂R⁸, —S(O)ₘR⁸, cyano, nitro, and azido; wherein two R³' may combine to form a 5- or 6-membered ring;

R⁵ is selected from the group consisting of hydrogen, halogen, haloalkyl, alkyl, alkoxy, alkenyl, alkynyl, cycloalkyl, cycloalkenyl, Het, aryl, aryl substituted with alkyl or —OCOR¹, and oxo; and n is 0, 1, 2, 3 or 4.

In an embodiment, the compound of Formula I or Formula II has the structure of Formula IIc²:

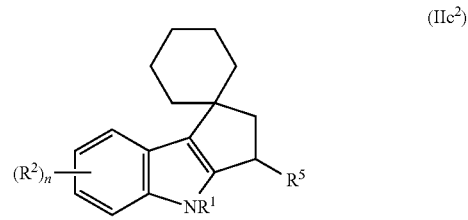

wherein R¹ is hydrogen, alkyl, alkenyl, alkynyl, aryl, benzyl, or alkylene optionally substituted with aryl;

R² is, for each occurrence, independently selected from the group consisting of hydrogen, halogen, haloalkyl, alkyl, alkoxy, alkenyl, alkynyl, cycloalkyl, cycloalkenyl, and —CO₂R⁸; and R⁵ is selected from the group consisting of hydrogen, halogen, haloalkyl, alkyl, alkoxy, alkenyl, alkynyl, cycloalkyl, cycloalkenyl, Het, aryl, aryl substituted with alkyl or —OCOR¹, and oxo; and n is 0, 1, 2, 3 or 4.

In an embodiment, the compound of Formula I or Formula II has the structure of Formula IId¹:

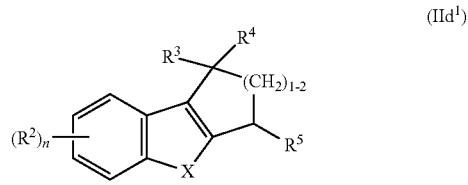

wherein X is NR¹;

R¹ is hydrogen, alkyl, alkenyl, alkynyl, aryl, benzyl, or alkylene optionally substituted with aryl;

R² is, for each occurrence, independently selected from the group consisting of hydrogen, halogen, haloalkyl, alkyl, alkoxy, alkenyl, alkynyl, cycloalkyl, cycloalkenyl, and —CO₂R⁸;

$R^3$ is selected from the group consisting of hydrogen, halogen, haloalkyl, alkyl, alkoxy, alkenyl, alkynyl, cycloalkyl, cycloalkenyl, Het, —$CO_2R^8$, aryl; aryl substituted with alkoxy, haloalkyl;

$R^4$ is selected from the group consisting of hydrogen, halogen, haloalkyl, alkyl, alkoxy, alkenyl, alkynyl, cycloalkyl, cycloalkenyl, Het, —$CO_2R^8$, aryl; aryl substituted with alkoxy, haloalkyl;

or, $R^3$ and $R^4$ together may combine to form a 4, 5, or 6 member cycloalkyl, aryl, or Het;

$R^5$ is selected from the group consisting of hydrogen, halogen, haloalkyl, alkyl, alkoxy, alkenyl, alkynyl, cycloalkyl, cycloalkenyl, Het, aryl, substituted aryl, and oxo;

and n is 0, 1, 2, 3 or 4.

In an embodiment, the compound of Formula I or Formula II has the structure of Formula IId²:

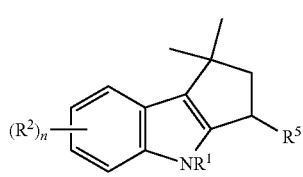

(IId²)

wherein $R^1$ is hydrogen, alkyl, alkenyl, alkynyl, aryl, benzyl, or alkylene optionally substituted with aryl;

$R^2$ is, for each occurrence, independently selected from the group consisting of hydrogen, halogen, haloalkyl, alkyl, alkoxy, alkenyl, alkynyl, cycloalkyl, cycloalkenyl, —$CO_2R^8$;

$R^5$ is selected from the group consisting of halogen, haloalkyl, alkyl, alkoxy, alkenyl, alkynyl, cycloalkyl, cycloalkenyl, Het, aryl, substituted aryl, oxo; and n is 0, 1, 2, 3 or 4.

In an embodiment, the compound of Formula I or Formula II has the structure of Formula IIe:

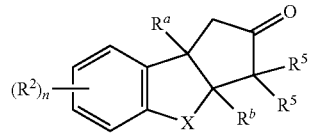

(IIe)

wherein $R^a$ and $R^b$ are absent, or independently selected from hydrogen, alkyl, hydroxyl, hydroxyalkyl; or wherein $R^a$ and $R^b$ together a 5- or 6-membered cycloalkyl or heterocycloalkyl with one or more heteroatoms independently selected from O or $NR^1$;

wherein $R^2$ is, for each occurrence, independently selected from the group consisting of hydrogen, halogen, haloalkyl, alkyl, alkoxy, alkenyl, alkynyl, cycloalkyl, cycloalkenyl, and —$CO_2R^8$;

$R^5$ is, for each occurrence, independently selected from the group consisting of hydrogen, halogen, haloalkyl, alkyl, alkoxy, alkenyl, alkynyl, cycloalkyl, cycloalkenyl, Het, aryl, substituted aryl, oxo; and n is 0, 1, 2, 3 or 4.

In an embodiment, the compound of Formula I or Formula III has the structure of Formula IIIa:

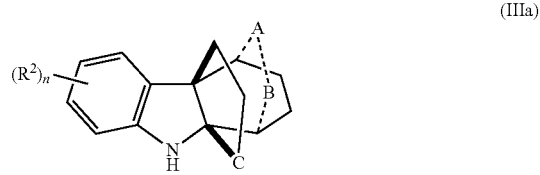

(IIIa)

wherein dashed bonds, independently, may be present or absent;

A and B are independently O, $NR^1$, $CH_2$, $CH(R^5)$, $C(R^5)_2$, or are absent;

C is O, $NR^1$, $CH_2$, $CH(R^5)$, or $C(R^5)_2$, $R^2$ is, for each occurrence, independently selected from the group consisting of hydrogen, halogen, haloalkyl, alkyl, alkoxy, alkenyl, alkynyl, cycloalkyl, cycloalkenyl, —$CO_2R^8$; and n is 0, 1, 2, 3 or 4.

In an embodiment, the compound of Formula I or Formula III has the structure of Formula IIIb:

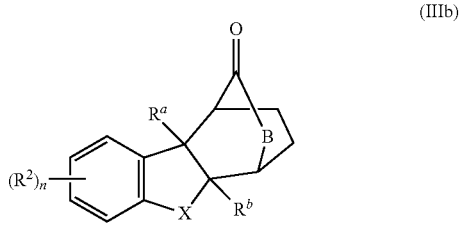

(IIIb)

wherein B is $CH_2$, $CH(R^5)$, $C(R^5)_2$, O, $NR^2$ or is absent;

wherein $R^a$ and $R^b$ are absent, or independently selected from hydrogen, alkyl, hydroxyl, hydroxyalkyl, aryl, benzyl, and amino; or wherein $R^a$ and $R^b$ may combine to form a 5- or 6-membered cycloalkyl or heterocycloalkyl with one or more heteroatoms independently selected from O or $NR^1$;

$R^2$ is, for each occurrence, independently selected from the group consisting of hydrogen, halogen, haloalkyl, alkyl, alkoxy, alkenyl, alkynyl, cycloalkyl, cycloalkenyl, —$CO_2R^8$; and n is 0, 1, 2, 3 or 4.

In an embodiment, the compound of Formula I or Formula IV has the structure of Formula IVa:

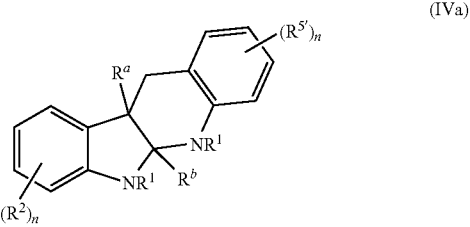

(IVa)

wherein $R^a$ and $R^b$ are absent, or independently selected from hydrogen, alkyl, hydroxyl, hydroxyalkyl, aryl, benzyl, and amino; or wherein $R^a$ and $R^b$ may combine to form a 5- or 6-membered cycloalkyl or heterocycloalkyl with one or more heteroatoms independently selected from O or $NR^1$;

$R^1$, for each occurrence, is independently selected from the group consisting of hydrogen, alkyl, alkenyl, alkynyl, aryl, benzyl, or alkylene optionally substituted with aryl;

R² is, for each occurrence, is independently selected from the group consisting of hydrogen, halogen, haloalkyl, alkyl, alkoxy, alkenyl, alkynyl, cycloalkyl, cycloalkenyl, and —CO₂R⁸;

R⁵' is, for each occurrence, independently selected from the group consisting of halogen, haloalkyl, alkyl, alkoxy, alkenyl, alkynyl, cycloalkyl, cycloalkenyl, Het, aryl, —NHR⁷, —NHHet, —NHR⁷Het, oxo, —OR⁸, —O-aryl, —OHet, —R⁷OR⁸, —NR⁸R⁹, —NR⁸-aryl, —R⁷NR⁸R⁹, —R⁷NR⁸-aryl, —R⁷C(O)R⁸, —C(O)R⁸, —CO₂R⁸, —R⁷CO₂R⁸, —C(O)NR⁸R⁹, —C(O)aryl, —C(O)NR⁸aryl, —C(O)Het, —C(O)NHR⁷Het, —R⁷C(O)NR⁸R⁹, —C(S)NR⁸R⁹, —R⁷C(S)NR⁸R⁹, —R⁷(NH)NR⁸R⁹, —C(NH)NR⁸R⁹, —R⁷C(NH)NR⁸R⁹, —S(O)₂NR⁸R⁹, —S(O)₂NR⁸aryl, —R⁷SO₂NHCOR⁸, —R⁷SO₂NR⁸R⁹, —R⁷SO₂R⁸, —S(O)ₘR⁸, cyano, nitro, and azido; and n is 0, 1, 2, 3 or 4.

In an embodiment, the compound of Formula I is selected from the compounds of Table 1 and pharmaceutically acceptable stereoisomers, isotopes, solvates and salts thereof.

BRIEF DESCRIPTION OF THE DRAWINGS

FIG. 1A shows that compound 34 reduces levels of both the pro-protein and the mature forms of PCSK9 in a dose-dependent manner. FIG. 1B shows that compound 34 reduces levels of PCSK9 mRNA in a dose-dependent manner. See Example 1-6.

FIG. 2A shows media PCSK9 levels versus time for B001 (compound 31), B003 (compound 33), B004 (compound 34), and B005 (compound 35). FIG. 2B shows media PCSK9 levels versus concentration of compound 34. See Example 1-2.

FIG. 4A shows percent cell survival for B001 (compound 31), B003 (compound 33), B004 (compound 34) and B005 (compound 35). FIG. 4B shows percent cell survival versus concentration of compound 34. See Example 1-1.

FIGS. 5A-5B show that compound 34 does not influence PCSK9 detection and does not affect PCSK9/LDLR interaction. FIG. 5A shows PCSK9 levels versus concentration of compound 34, showing that compound 34 does not interfere with PCSK9 detection. FIG. 5B shows arbitrary binding units versus concentration of compound 34, showing that compound 34 does not affect PCSK9 binding to LDLR (EGF-A domain). See Example 1-4.

FIG. 6A shows secreted albumin levels versus concentration of compound 34. FIG. 6B shows intracellular albumin levels versus concentration of compound 34. Reduction in secreted and intracellular albumin at 20 µM and 50 µM of compound 34 are the results of increased cell death in these concentrations (FIG. 4B). See Examples 1-8 and 1-9.

FIG. 7A shows secreted apoE levels versus concentration of compound 34. FIG. 7B shows apoE mRNA levels versus concentration of compound 34. FIG. 7C shows intracellular apoE levels versus concentration of compound 34. See Examples 1-10, 1-11 and 1-12.

FIG. 8A shows protein abundance in the presence of compound 34 versus control. FIG. 8B shows the log 2 changes in the 4000 most abundant proteins in HepG2 cells in the presence of compound 34 compared to controls. See Example 1-13.

FIG. 10A shows a maximal drop in PCSK9 of 28.5%, 6 hours after oral administration of 30 mg/kg of compound 34, with levels getting back to baseline after 18 hours after administration. N=3/group. FIG. 10B shows a maximal drop in PCSK9 of 33.4%, 6 hours after oral administration of 100 mg/kg of compound 34 with levels getting back to baseline after 24 hours after administration. N=3/group.

FIG. 11A shows that mouse plasma cholesterol, which is mostly HDL, is not affected by single oral administration of 100 mg/kg of compound 34. FIG. 11B shows that liver function (measured as AST activity) is not affected by single oral administration of 100 mg/kg of compound 34.

FIG. 12A shows a significant 36.2% drop in plasma PCSK9 on day 5. N=6. FIG. 12B shows that all mice receiving compound 34 presented with a drop in PCSK9 levels.

FIG. 13A shows no significant changes plasma cholesterol, which in the mouse is mostly HDL, is not affected by compound 34. N=6. FIG. 13B shows that liver function (measured as AST activity) is not affected by compound 34. N=6.

FIG. 14A shows immune-blot of LDLR in livers of mice. FIG. 14B is quantification of FIG. 14A and shows that compound 34 increases hepatic LDLR by 16.2%. N=4.

DETAILED DESCRIPTION

Figure 1B:
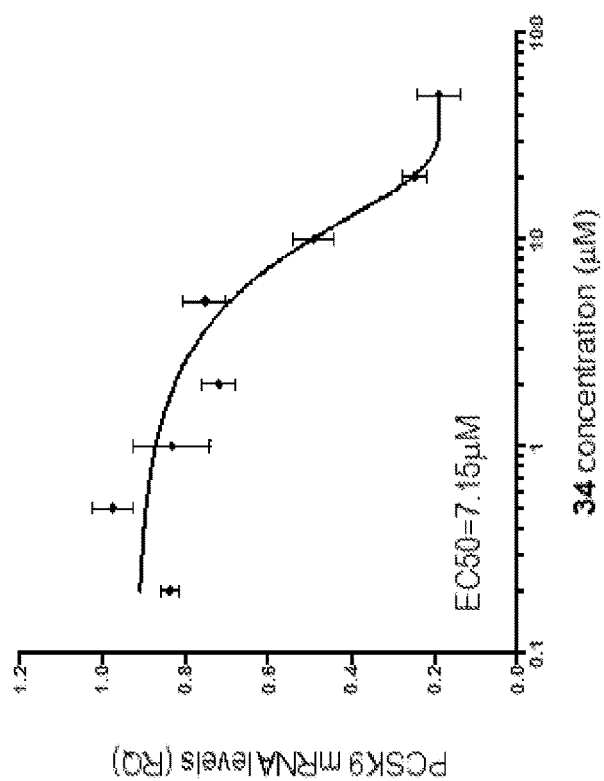
FIGS. 1A-1B show that compound 34 reduces intracellular PCSK9 in HepG2 cells.
Figure 1A:
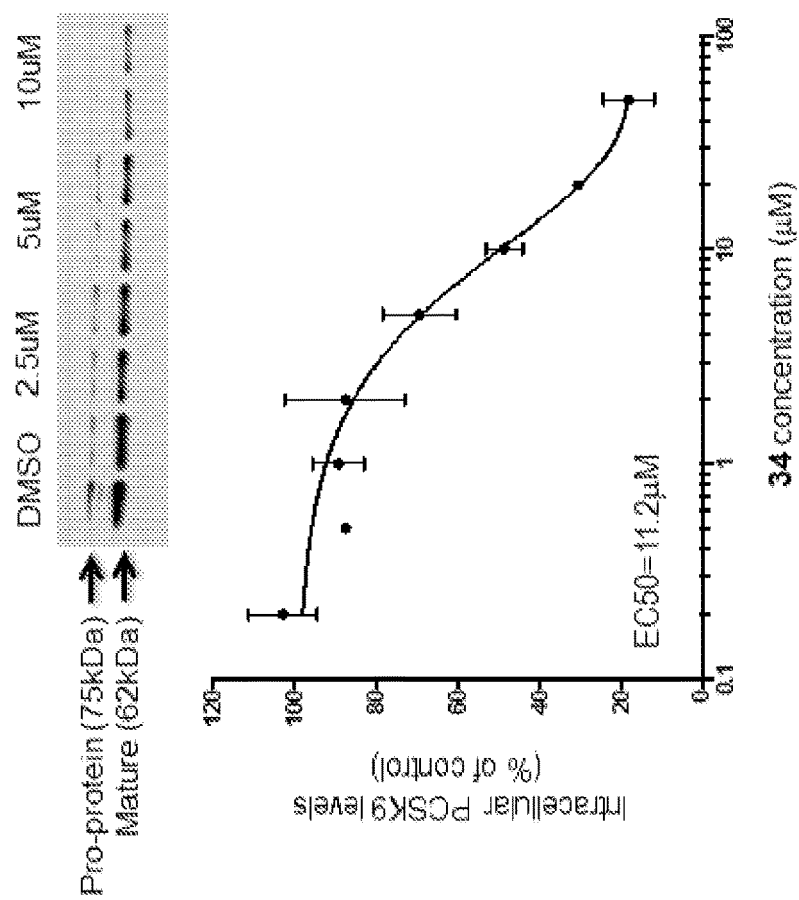

Elevated plasma low-density lipoprotein (LDL) cholesterol is an important risk factor associated with, but not limited to, cardiovascular disease (CVD), hypercholesterolemia, hyperlipidemia, dyslipidemia, obesity and diabetes. Plasma LDL cholesterol is controlled through its production rate and its uptake upon binding the LDL receptor (LDLR), followed by the internalization of the LDL-LDLR complex. Proprotein Convertase Subtilisin-like/Kexin type 9 (hereinafter "PCSK9") is a critical player in LDL metabolism through its interaction with hepatic LDLR. PCSK9 binds to the LDLR in the liver and accelerates its degradation, leading to reduced LDL clearance and elevated plasma LDL cholesterol. PCSK9 is mainly synthesized in liver and is rapidly secreted into plasma after its maturation through an autocatalytic processing at the motif LVFAQ in the endoplasmic reticulum.

Studies have reported that inactivation of PCSK9 in mice reduces plasma cholesterol levels primarily by increasing hepatic expression of LDLR protein and thereby promoting clearance of circulating LDL cholesterol. Partial or complete loss of a functional PCSK9 in humans is not associated with clear deleterious effect, and thus PCSK9 has emerged as an attractive inhibition target for lowering plasma LDL cholesterol. Recent successful demonstrations of anti-PCSK9 antibodies that lowered plasma LDL-cholesterol levels in dyslipidemic and hypercholesterolemic patients have provided strong validation to support the notion that lowering circulating PCSK9 levels to upregulate hepatic LDLR is beneficial for reducing the risk of cardiovascular disease in humans.

PCSK9 is also identified as a protein with a genetic mutation in some forms of familial hypercholesterolemia. Population studies have shown that some PCSK9 mutations are "gain-of-function" and are found in individuals with autosomal dominant hypercholesterolemia, while other "loss-of-function" (LOF) mutations are linked with reduced plasma cholesterol. Morbidity and mortality studies in this group clearly demonstrated that reducing PCSK9 function significantly diminished the risk of cardiovascular disease.

Furthermore, among the metabolic abnormalities that commonly accompany diabetes are disturbances in the production and clearance of plasma lipoproteins. Diabetic dyslipidemia consists of low high-density lipoprotein (HDL), increased triglycerides, and postprandial hyperlipidemia. This pattern is most frequently seen in type 2 diabetes and may be a treatable risk factor for subsequent cardiovascular disease.

Defects in insulin action and hyperglycemia could lead to changes in plasma lipoproteins in patients with diabetes. The lipoprotein abnormalities commonly present in type 2 diabetes include hypertriglyceridemia and reduced HDL cholesterol. In addition, LDL is converted to smaller, more atherogenic, lipoproteins termed as small dense LDL. In contrast to type 1 diabetes, this phenotype is not usually fully corrected with glycemic control. Moreover, this dyslipidemia often is found in prediabetics, patients with insulin resistance but normal indexes of plasma glucose.

METHODS OF THE INVENTION

Methods of the invention are provided in several aspects, including the following.

In a first aspect, provided herein is a method for reducing PCSK9 in a cell, the method comprising contacting the cell with a compound of the invention. In an embodiment, the cell is one of a plurality of cells. In an embodiment, the cell is a hepatocyte cell. In an embodiment, the amount of PCSK9 in the cell is reduced by at least 10%, 20%, 30%, 40%, 50%, 60%, 70%, or 80% compared to amount of PCSK9 in the cell prior to contact with the compound of the invention. In a particular embodiment, the amount of PCSK9 in the cell is reduced by at least 35% when the cell is contacted by a 5 µM solution of a compound of the invention.

In an embodiment, the amounts of both the pro-protein and mature forms of PCSK9 are reduced. In an embodiment, the cell is a hepatocyte cell. In an embodiment, the secretion of PCSK9 is inhibited.

In a second aspect, provided herein is a method for increasing the level of LDLR in a cell, comprising contacting the cell with a compound of the invention. In an embodiment, the cell is one of a plurality of cells. In an embodiment, the cell is a hepatocyte cell. In an embodiment, the level of LDLR in the cell is increased compared to the amount of low density lipoprotein receptor (LDLR) in the cell prior to contact with the compound of the invention. In an embodiment, the level of LDLR in the cell is increased by at least 10%, 20%, 30%, 40%, 50%, 60%, 70%, or 80% compared to level of LDLR in the cell prior to contact with the compound of the invention. In a particular embodiment, the level of LDLR in the cell is increased by at least 20% when the cell is contacted by a 5 µM solution of a compound of the invention.

In a third aspect, provided herein is a method for reducing the PCSK9 level in a subject, the method comprising administering to the subject an effective amount of a compound of the invention. In an embodiment, the amounts of both the pro-protein and mature forms of PCSK9 are reduced. PCSK9 levels may be measured in the serum, plasma, tissue, or isolated cells (e.g., hepatocyte cells) of the subject. In an embodiment, the amount of PCSK9 in the subject is reduced by at least 10%, 20%, 30%, 40%, 50%, 60%, 70%, or 80% compared to amount of PCSK9 in the subject prior to administering the compound of the invention. In an embodiment, the secretion of PCSK9 is inhibited. In an embodiment, the production of PCSK9 is inhibited.

In a fourth aspect, provided herein is a method for increasing the level of LDLR in a subject, comprising administering to the subject an effective amount of a compound of the invention. LDLR level may be measured in the tissue or cells of the subject. In an embodiment, the level of LDLR in the subject is increased compared to the amount of low density lipoprotein receptor (LDLR) in the cell prior to administering the compound of the invention. In an embodiment, the level of LDLR in the subject is increased by at least 10%, 20%, 30%, 40%, 50%, 60%, 70%, or 80% compared to level of LDLR in the subject prior to administering the compound of the invention. In a particular embodiment, the level of LDLR in the subject is increased by at least 16% when about 30 mg/kg or about 100 mg/kg of a compound of the invention is administered to the subject.

In a fifth aspect, provided herein is a method of decreasing the amount of low density lipoprotein (LDL) in a subject, comprising administering to the subject an effective amount of a compound of the invention. LDL level may be measured in the serum or plasma of the subject.

In an embodiment, the amount of low density lipoprotein (LDL) in the subject is reduced compared to the level of LDL in the subject prior to administering the compound of the invention. In an embodiment, the level of LDL in the subject is reduced by at least 10%, 20%, 30%, 40%, 50%, 60%, 70%, or 80% compared to level of LDL in the subject prior to administering the compound of the invention.

In a sixth aspect, provided herein is a method of treating or preventing a condition associated with an elevated level of LDL, comprising administering to a subject in need of such treatment an effective amount of a compound of the invention. In an embodiment, the method is a method of treating a condition associated with an elevated level of LDL. In an embodiment, the method is a method of preventing a condition associated with an elevated level of LDL.

In a seventh aspect, provided herein is a method of treating or preventing a condition associated with an elevated level of PCSK9, comprising administering to a subject in need of such treatment an effective amount of a compound of the invention. In an embodiment, the plasma PCSK9 level in the subject is reduced compared to plasma PCSK9 level in the subject prior to administration of the compound of the invention. In an embodiment, the plasma PCSK9 level in the subject is reduced by at least 10%, 20%, 30%, 40%, 50%, 60%, 70%, or 80% compared to plasma PCSK9 level in the subject prior to administration of the compound of the invention. In a particular embodiment, the plasma PCSK9 level in the subject is reduced by at least 25% when about 30 mg/kg or about 100 mg/kg of a compound of the invention is administered to the subject.

Provided herein are certain embodiments of the above-disclosed methods of treating or preventing.

In an embodiment, the level of LDL in the subject is reduced compared to the level of LDL in the subject prior to administering the compound of the invention.

In an embodiment, the hepatic level of LDLR in the subject is increased compared to amount of hepatic LDLR in the subject prior to administering the compound of the invention.

In an embodiment, the level of high density lipoprotein (HDL) in the subject is not substantially reduced compared to amount of HDL in the subject prior to administering the compound of the invention.

In an embodiment, the condition associated with an elevated level of LDL or PCSK9 is selected from the group consisting of hypercholesterolemia, hyperlipidemia, dyslipidemia, metabolic syndrome, a diabetic condition, heart disease, cardiovascular disease, an atherosclerotic disease, stroke and Alzheimer's disease. In an embodiment, the condition is congestive heart failure.

In an embodiment, the condition associated with dyslipidemia is selected from the group consisting of familial combined hyperlipidemia, familial hypertriglyceridemia, familial hypercholesterolemia, remnant removal disease, hepatic lipase deficiency, dietary indiscretion, hypothyroidism, nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia. In a particular embodiment, the dyslipidemia is associated with a pre-diabetic condition.

In an embodiment, the atherosclerotic disease is selected from the group consisting of coronary artery disease, peripheral arterial disease, stroke (ischemic and hemorrhagic), angina pectoris, cerebrovascular disease, acute coronary syndrome, or myocardial infarction.

In an embodiment, the familial hypercholesterolemia is selected from the group consisting of heterozygous hypercholesterolemia, homozygous hypercholesterolemia, familial defective apolipoprotein B-100, and polygenic hypercholesterolemia.

In an embodiment, the diabetic condition is selected from the group consisting of type 1 diabetes, type 2 diabetes, gestational diabetes, latent autoimmune diabetes in adults (LADA), Maturity Onset Diabetes of the Young (MODY) and Neonatal Diabetes Mellitus (NDM).

In an embodiment, the binding of PCSK9 to LDLR is not affected by the administration to the subject of the compound of the invention. In certain embodiments, administration to a subject of the compound of the invention does not result in increased levels of PCSK9 binding to LDLR, or administration to a subject of the compound of the invention does not result in decreased levels of PCSK9 binding to LDLR.

In an embodiment, the compound of the invention interacts directly with LDLR. In an embodiment, the compound of the invention interacts indirectly with LDLR.

In an embodiment, the albumin level of the subject is not affected by administration to the subject of the compound of the invention. In certain embodiments, administration to a subject of the compound of the invention does not result in increased albumin levels, or administration to the subject of the compound of the invention does not result in decreased albumin levels. The level of albumin may be measured in the serum or plasma.

In an embodiment, the apoE level of the subject is not affected by administration to the subject of the compound of the invention. In certain embodiments, administration to the subject of the compound of the invention does not result in increased apoE levels, or administration to a subject of the compound of the invention does not result in decreased apoE levels. The level of apoE may be measured in the serum or plasma.

In an embodiment, the PCSK9 mRNA of the subject is not inhibited by administration to the subject of the compound of the invention. In certain embodiments, administration to a subject of the compound of the invention does not result in inhibition of PCSK9 mRNA transcription and/or production in the subject.

In an embodiment, the hepatic transaminase level of the subject is not affected by administration to the subject of the compound of the invention. In certain embodiments, administration to the subject of the compound of the invention does not result in increased hepatic transaminase levels, or administration to the subject of the compound of the invention does not result in decreased hepatic transaminase levels.

In some embodiments of the methods described herein, the compound of the invention is administered orally. In some embodiments, the compound of the invention is administered in the form of a pharmaceutical composition.

Combinations

In some embodiments, the methods of the invention further comprise contacting the cell with one or more of additional active agents. In some embodiments, the methods of the invention further comprise administering to the subject one or more of additional active agents.

In some embodiments, the additional active agent is selected from the group consisting of a statin, ACE inhibitor, Angiotensin II receptor blocker (ARB), antiarrhythmic agent, antiplatelet agent, anti-clotting agent, anti-cholesterol agent, anti-diabetic agent, diuretic, vasodilator, blood thinner, beta blocker, amiodarone, digoxin, and aspirin.

Non-limiting examples of statins are atorvastatin, fluvastatin, lovastatin, pitavastatin, pravastatin, rosuvastatin, and simvastatin. In some embodiments, a statin is further combined with niacin, an absorption inhibitor (ezetimibe), a lipid modifying agent, or a combination thereof.

Non-limiting examples of ACE inhibitors are Capoten (captopril), Vasotec (enalapril), Prinivil, Zestril (lisinopril), Lotensin (benazepril), Monopril (fosinopril), Altace (ramipril), Accupril (quinapril), Aceon (perindopril), Mavik (trandolapril), and Univasc (moexipril).

Non-limiting examples of ARBs are Cozaar (losartan), Diovan (valsartan), Avapro (irbesartan), Atacand (candesartan), and Micardis (telmisartan).

Non-limiting examples of antiarrhythmic agents are Tambocor (flecamide), Procanbid (procainamide), Cordarone (amiodarone), and Betapace (sotalol).

Non-limiting examples of anticlotting agents are Tissue plasminogen activator (TPA), Tenecteplase, Alteplase, Urokinase, Reteplase, and Streptokinase.

Non-limiting examples of beta-blockers are Sectral (acebutolol), Zebeta (bisoprolol), Brevibloc (esmolol), Inderal (propranolol), Tenormin (atenolol), Normodyne, Trandate (labetalol), Coreg (carvedilol), Lopressor, and Toprol-XL (metoprolol).

Non-limiting examples of calcium channel blockers are Norvasc (amlodipine), Plendil (felodipine), Cardizem, Cardizem CD, Cardizem SR, Dilacor XR, Diltia XT, Tiazac (diltiazem), Calan, Calan SR, Covera-HS, Isoptin, Isoptin SR, Verelan, Verelan PM (verapamil), Adalat, Adalat CC, Procardia, Procardia XL (nifedipine), Cardene, Cardene SR (nicardipine), Sular (nisoldipine), Vascor (bepridil), and Caduet which is a combination of a statin cholesterol drug and amlodipine.

Non-limiting examples of diuretics are Lasix (furosemide), Bumex (bumetanide), Demadex (torsemide), Esidrix (hydrochlorothiazide), Zaroxolyn (metolazone), and Aldactone (spironolactone).

Non-limiting examples of heart failure drugs are Dobutrex (dobutamine), and Primacor (milrinone).

Non-limiting examples of vasodilators are Dilatrate-SR, Iso-Bid, Isonate, Isorbid, Isordil, Isotrate, Sorbitrate (isosorbide dinitrate), IMDUR (isorbide mononitrate), and BiDil (hydralazine with isosorbide dinitrate).

Non-limiting examples of blood thinners are Warfarin (coumadin), Heparin, Lovenox, and Fragmin.

Non-limiting examples of other anti-cholesterol drugs are holestyramine (Questran), gemfibrozil (Lopid, Gemcor), Omacor, and pantethine.

Non-limiting examples of anti-diabetic drugs are alpha-glucosidase inhibitors, biguanides, dipeptidyl peptidase-4 inhibitors, insulin, meglitinides, sulfonylurea, and thiazolidinediones.

Compounds of the Invention

"Compounds of the invention" refers to compounds disclosed herein, or pharmaceutically acceptable stereoisomers, isotopes, solvates and salts thereof. For example, "compounds of the invention" encompass compounds of Formulas I, II, IIa, IIa$^1$, IIa$^2$, IIb, IIb$^1$, IIb$^2$, IIc$^1$, IIc$^2$, IId$^1$, IId$^2$, IIe, III, IIIa, IIIb, IV, IVa, the compounds of Table 1, and pharmaceutically acceptable stereoisomers, isotopes, solvates and salts thereof. Compounds of the invention include cycloalkyl[b]indoles, e.g., cyclopenta, cyclohexa- and cyclohepta[b]indoles, as previously described. See, e.g., US 2015/0057326 and WO 2013/177241, which are each incorporated herein by reference in their entireties for all they teach and describe.

In various aspects and embodiments described herein, one or more compounds of the invention are administered to a subject, contacted with a cell, used for the treatment of a disorder described herein, and used in the manufacture of a medicament for the treatment of a disorder described herein.

In one aspect, provided herein is a method for reducing the PCSK9 level in a subject, the method comprising administering to the subject an effective amount of a compound of Formula I, or a pharmaceutically acceptable stereoisomer, isotope, solvate or salt thereof:

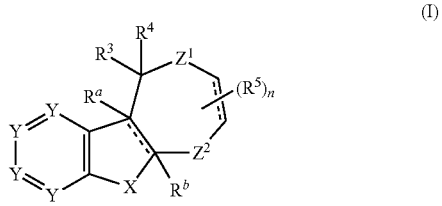

(I)

wherein
dashed bonds, independently, are present or absent;
X is O, S, CR$_2$ or NR$^1$;
Y is, for each occurrence, independently N or C(R$_6$);
Z$^1$ is CH$_2$, CH(R$^5$), C(R$^5$)$_2$ or is absent;
Z$^2$ is CH$_2$, CH(R$^5$), C(R$^5$)$_2$, NR$_2$ or is absent;
R$^a$ and R$^b$ are absent, or independently selected from hydrogen, alkyl, hydroxyl, and amino; wherein R$_a$ and R$_b$ may combine to form a 5- or 6-membered ring;
R$^1$ is hydrogen, alkyl, alkenyl, alkynyl or aryl;
R$^2$ is, for each occurrence, independently selected from the group consisting of hydrogen, halogen, haloalkyl, alkyl, alkoxy, alkenyl, alkynyl, cycloalkyl, cycloalkenyl, —R$^7$-cycloalkyl, aryl, —NHR$^7$, Het, —NHHet, —NHR$^7$Het, —OR$^8$, —O-aryl, —OHet, —R$^7$OR$^8$, —NR$^8$R$^9$, —NR$^8$-aryl, —R$^7$NR$^8$R$^9$, —R$^7$NR$^8$-aryl, —R$^7$C(O)R$^8$, —C(O)R$^8$, —CO$_2$R$^8$, —R$^7$CO$_2$R$^8$, —C(O)NR$^8$R$^9$, —C(O)aryl, —C(O)NR$^8$aryl, —C(O)Het, —C(O)NHR$^7$Het, —R$^7$C(O) NR$^8$R$^9$, —C(S)NR$^8$R$^9$, —R$^7$C(S)NR$^8$R$^9$, —R$^7$(NH)NR$^8$R$^9$, —C(NH)NR$^8$R$^9$, —R$^7$C(NH)NR$^8$R$^9$, —S(O)$_2$NR$^8$R$^9$, —S(O)$_2$NR$^8$aryl, —R$^7$SO$_2$NHCOR$^8$, —R$^7$SO$_2$NR$^8$R$^9$, —R$^7$SO$_2$R$^8$, —S(O)$_m$R$^8$, cyano, nitro, and azido;

R$^3$ is selected from the group consisting of hydrogen, halogen, haloalkyl, alkyl, alkoxy, alkenyl, alkynyl, cycloalkyl, cycloalkenyl, Het, aryl, —NHR$^7$, —NHHet, —NHR$^7$Het, —OR$^8$, —O-aryl, —OHet, —R$^7$OR$^8$, —NR$^8$R$^9$, —NR$^8$-aryl, —R$^7$NR$^8$R$^9$, —R$^7$NR$^8$-aryl, —R$^7$C (O)R$^8$, —C(O)R$^8$, —CO$_2$R$^8$, —R$^7$CO$_2$R$^8$, —C(O)NR$^8$R$^9$, —C(O)aryl, —C(O)NR$^8$aryl, —C(O)Het, —C(O) NHR$^7$Het, —R$^7$C(O)NR$^8$R$^9$, —C(S)NR$^8$R$^9$, —R$^7$C(S) NR$^8$R$^9$, —R$^7$(NH)NR$^8$R$^9$, —C(NH)NR$^8$R$^9$, —R$^7$C(NH) NR$^8$R$^9$, —S(O)$_2$NR$^8$R$^9$, —S(O)$_2$NR$^8$aryl, —R$^7$SO$_2$NHCOR$^8$, —R$^7$SO$_2$NR$^8$R$^9$, —R$^7$SO$_2$R$^8$, —S(O)$_m$R$^8$, cyano, nitro, and azido;

R$^4$ is selected from the group consisting of hydrogen, halogen, haloalkyl, alkyl, alkoxy, alkenyl, alkynyl, cycloalkyl, cycloalkenyl, Het, aryl, —NHR$^7$, —NHHet, —NHR$^7$Het, —OR$^8$, —O-aryl, —OHet, —R$^7$OR$^8$, —NR$^8$R$^9$, —NR$^8$-aryl, —R$^7$NR$^8$R$^9$, —R$^7$NR$^8$-aryl, —R$^7$C (O)R$^8$, —C(O)R$^8$, —CO$_2$R$^8$, —R$^7$CO$_2$R$^8$, —C(O)NR$^8$R$^9$, —C(O)aryl, —C(O)NR$^8$aryl, —C(O)Het, —C(O) NHR$^7$Het, —R$^7$C(O)NR$^8$R$^9$, —C(S)NR$^8$R$^9$, —R$^7$C(S)

NR⁸R⁹, —R⁷(NH)NR⁸R⁹, —C(NH)NR⁸R⁹, —R⁷C(NH) NR⁸R⁹, —S(O)₂NR⁸R⁹, —S(O)₂NR⁸aryl, —R⁷SO₂NHCOR⁸, —R⁷SO₂NR⁸R⁹, —R⁷SO₂R⁸, —S(O)ₘR⁸, cyano, nitro, and azido;

R⁵ is, for each occurrence, independently selected from the group consisting of halogen, haloalkyl, alkyl, alkoxy, alkenyl, alkynyl, cycloalkyl, cycloalkenyl, Het, aryl, —NHR⁷, —NHHet, —NHR⁷Het, oxo, —OR⁸, —O-aryl, —OHet, —R⁷OR⁸, —NR⁸R⁹, —NR⁸-aryl, —R⁷NR⁸R⁹, —R⁷NR⁸-aryl, —R⁷C(O)R⁸, —C(O)R⁸, —CO₂R⁸, —R⁷CO₂R⁸, —C(O)NR⁸R⁹, —C(O)aryl, —C(O)NR⁸aryl, —C(O)Het, —C(O)NHR⁷Het, —R⁷C(O)NR⁸R⁹, —C(S)NR⁸R⁹, —R⁷C(S)NR⁸R⁹, —R⁷(NH)NR⁸R⁹, —C(NH)NR⁸R⁹, —R⁷C(NH)NR⁸R⁹, —S(O)₂NR⁸R⁹, —S(O)₂NR⁸aryl, —R⁷SO₂NHCOR⁸, —R⁷SO₂NR⁸R⁹, —R⁷SO₂R⁸, —S(O)ₘR⁸, cyano, nitro, and azido;

R⁶ is, for each occurrence, independently selected from hydrogen, halogen, haloalkyl, alkyl, alkoxy, alkenyl, alkynyl, cycloalkyl, cycloalkenyl, —R⁷-cycloalkyl, aryl, —NHR⁷, Het, —NHHet, —NHR⁷Het, —OR⁸, —O-aryl, —OHet, —R⁷OR⁸, —NR⁸R⁹, —NR⁸-aryl, —R⁷NR⁸R⁹, —R⁷NR⁸-aryl, —R⁷C(O)R⁸, —C(O)R⁸, —CO₂R⁸, —R⁷CO₂R⁸, —C(O)NR⁸R⁹, —C(O)aryl, —C(O)NR⁸aryl, —C(O)Het, —C(O)NHR⁷Het, —R⁷C(O)NR⁸R⁹, —C(S)NR⁸R⁹, —R⁷C(S)NR⁸R⁹, —R⁷(NH)NR⁸R⁹, —C(NH)NR⁸R⁹, —R⁷C(NH)NR⁸R⁹, —S(O)₂NR⁸R⁹, —S(O)₂NR⁸aryl, —R⁷SO₂NHCOR⁸, —R⁷SO₂NR⁸R⁹, —R⁷SO₂R⁸, —S(O)ₘR⁸, cyano, nitro, and azido;

R⁷ is independently selected from an alkyl, cycloalkyl alkenyl, cycloalkenyl and alkynyl R⁸ is independently selected from the group of hydrogen, an alkyl, alkoxy, alkenyl, alkynyl, cycloalkyl, cycloalkenyl, —R⁷cycloalkyl, —R⁷OH, —R⁷(OR⁷)_w, and —R⁷NR¹⁰R¹¹ group;

R⁹ is independently selected from the group of hydrogen, an alkyl, alkoxy, alkenyl, alkynyl, cycloalkyl, cycloalkenyl, —R⁷cycloalkyl, —R⁷OH, —R⁷(OR⁷)_w, and —R⁷NR¹⁰R¹¹ group;

R¹⁰ and R¹¹ are the same or different and are independently selected from the group of alkyl, cycloalkyl, alkenyl, cycloalkenyl, and alkynyl;

m, for each occurrence, independently is 0, 1 or 2;
n is 0, 1, 2, 3, 4, 5 or 6;
w is an integer selected from 1-10; and
wherein any two of R², R³, R⁴ and R⁵, or two R⁵, may combine to form a 5- or 6-membered ring.

Also provided herein is a method for reducing the PCSK9 level in a subject, the method comprising administering to the subject an effective amount of a compound of Formula II, III, or IV, or a pharmaceutically acceptable stereoisomer, wherein the compound of Formula II, III, or IV is an embodiment of Formula I; or an isotope, solvate or salt thereof:

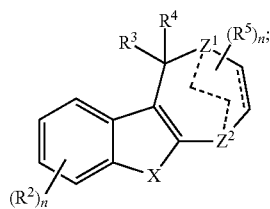

(II)

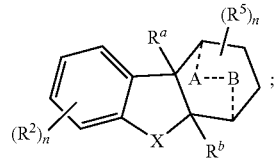

(III)

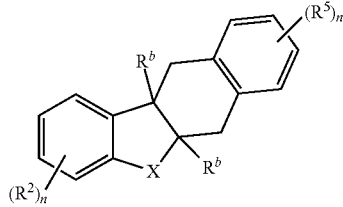

(IV)

wherein dashed bonds, independently, are present or absent;

A and B are independently O, NR¹, CH₂, CH(R⁵), C(R⁵)₂, or are absent;

X is NR¹;

Z¹ is CH₂, CH(R⁵), C(R⁵)₂ or is absent;

Z² is CH₂, CH(R⁵), C(R⁵)₂, or is absent; or wherein Z¹ and Z² together form a C:1-3 carbocyclic bridge;

R^a and R^b are absent, or are independently selected from hydrogen, alkyl, hydroxyl, hydroxyalkyl, aryl, benzyl, and amino; or wherein R^a and R^b together a 5- or 6-membered cycloalkyl or heterocycloalkyl with one or more heteroatoms independently selected from O or NR¹;

R¹ is hydrogen, alkyl, alkenyl, alkynyl, aryl, benzyl, or alkylene optionally substituted with aryl;

R² is, for each occurrence, independently selected from the group consisting of hydrogen, halogen, haloalkyl, alkyl, alkoxy, alkenyl, alkynyl, cycloalkyl, cycloalkenyl, —R⁷-cycloalkyl, aryl, —NHR⁷, Het, —NHHet, —NHR⁷Het, —OR⁸, —O-aryl, —OHet, —R⁷OR⁸, —NR⁸R⁹, —NR⁸-aryl, —R⁷NR⁸R⁹, —R⁷NR⁸-aryl, —R⁷C(O)R⁸, —C(O)R⁸, —CO₂R⁸, —R⁷CO₂R⁸, —C(O)NR⁸R⁹, —C(O)aryl, —C(O)NR⁸aryl, —C(O)Het, —C(O)NHR⁷Het, —R⁷C(O)NR⁸R⁹, —C(S)NR⁸R⁹, —R⁷C(S)NR⁸R⁹, —R⁷(NH)NR⁸R⁹, —C(NH)NR⁸R⁹, —R⁷C(NH)NR⁸R⁹, —S(O)₂NR⁸R⁹, —S(O)₂NR⁸aryl, —R⁷SO₂NHCOR⁸, —R⁷SO₂NR⁸R⁹, —R⁷SO₂R⁸, —S(O)ₘR⁸, cyano, nitro, and azido;

R³ is selected from the group consisting of hydrogen, halogen, haloalkyl, alkyl, alkoxy, alkenyl, alkynyl, cycloalkyl, cycloalkenyl, Het, aryl, —NHR⁷, —NHHet, —R⁷Het, —NHR⁷Het, —OR⁸, —O-aryl, —OHet, —R⁷OR⁸, —NR⁸R⁹, —NR⁸-aryl, —R⁷NR⁸R⁹, —R⁷NR⁸-aryl, —R⁷C(O)R⁸, —C(O)R⁸, —CO₂R⁸, —R⁷CO₂R⁸, —C(O)NR⁸R⁹, —C(O)aryl, —C(O)NR⁸aryl, —C(O)Het, —C(O)NHR⁷Het, —R⁷C(O)NR⁸R⁹, —C(S)NR⁸R⁹, —R⁷C(S)NR⁸R⁹, —R⁷(NH)NR⁸R⁹, —C(NH)NR⁸R⁹, —R⁷C(NH)NR⁸R⁹, —S(O)₂NR⁸R⁹, —S(O)₂NR⁸aryl, —R⁷SO₂NHCOR⁸, —R⁷SO₂NR⁸R⁹, —R⁷SO₂R⁸, —S(O)ₘR⁸, cyano, nitro, and azido;

R⁴ is selected from the group consisting of hydrogen, halogen, haloalkyl, alkyl, alkoxy, alkenyl, alkynyl, cycloalkyl, cycloalkenyl, Het, aryl, —NHR⁷, —NHHet, —R⁷Het —NHR⁷Het, —OR⁸, —O-aryl, —OHet, —R⁷OR⁸, —NR⁸R⁹, —NR⁸-aryl, —R⁷NR⁸R⁹, —R⁷NR⁸-aryl, —R⁷C(O)R⁸, —C(O)R⁸, —CO₂R⁸, —R⁷CO₂R⁸, —C(O)NR⁸R⁹, —C(O)aryl, —C(O)NR⁸aryl, —C(O)Het, —C(O)NHR⁷Het, —R⁷C(O)NR⁸R⁹, —C(S)NR⁸R⁹, —R⁷C(S)NR⁸R⁹, —R⁷(NH)NR⁸R⁹, —C(NH)NR⁸R⁹, —R⁷C(NH)

—NR⁸R⁹, —S(O)₂NR⁸R⁹, —S(O)₂NR⁸aryl, —R⁷SO₂NHCOR⁸, —R⁷SO₂NR⁸R⁹, —R⁷SO₂R⁸, —S(O)ₘR⁸, cyano, nitro, and azido;

or, R³ and R⁴ together may combine to form a 4, 5, or 6 member cycloalkyl, aryl, or Het;

R⁵ is, for each occurrence, independently selected from the group consisting of hydrogen, halogen, haloalkyl, alkyl, alkoxy, alkenyl, alkynyl, cycloalkyl, cycloalkenyl, Het, aryl, substituted aryl, —NHR⁷, —NHHet, —NHR⁷Het, oxo, —OR⁸, —O-aryl, —OHet, —R⁷OR⁸, —NR⁸R⁹, —NR⁸-aryl, —R⁷NR⁸R⁹, —R⁷NR⁸-aryl, —R⁷C(O)R⁸, —C(O)R⁸, —CO₂R⁸, —R⁷CO₂R⁸, —C(O)NR⁸R⁹, —C(O)aryl, —C(O)NR⁸aryl, —C(O)Het, —C(O)NHR⁷Het, —R⁷C(O)NR⁸R⁹, —C(S)NR⁸R⁹, —R⁷C(S)NR⁸R⁹, —R⁷(NH)NR⁸R⁹, —C(NH)NR⁸R⁹, —R⁷C(NH)NR⁸R⁹, —S(O)₂NR⁸R⁹, —S(O)₂NR⁸aryl, —R⁷SO₂NHCOR⁸, —R⁷SO₂NR⁸R⁹, —R⁷SO₂R⁸, —S(O)ₘR⁸, cyano, nitro, and azido;

R⁷ is independently selected from an alkyl, cycloalkyl alkenyl, cycloalkenyl and alkynyl;

R⁸ is independently selected from the group of hydrogen, an alkyl, alkoxy, alkenyl, alkynyl, cycloalkyl, cycloalkenyl, —R⁷cycloalkyl, —R⁷OH, —R⁷(OR⁷)ᵥᵥ, and —R⁷NR¹⁰R¹¹ group;

R⁹ is independently selected from the group of hydrogen, an alkyl, alkoxy, alkenyl, alkynyl, cycloalkyl, cycloalkenyl, —R⁷cycloalkyl, —R⁷OH, —R⁷(OR⁷)ᵥᵥ, and —R⁷NR¹⁰R¹¹ group;

R¹⁰ and R¹¹ are the same or different and are independently selected from the group of alkyl, cycloalkyl, alkenyl, cycloalkenyl, and alkynyl;

m, for each occurrence, independently is 0, 1 or 2;

n, for each occurrence, independently is 0, 1, 2, 3, 4, 5 or 6;

wherein any two of R², R³, R⁴ and R⁵, or two R⁵, may combine to form a 5- or 6-membered ring.

In an embodiment, two R⁵ substituents may be located on the same carbon atom. In an embodiment, the ring formed from two R⁵ substituents may be bridged, fused, or may form a spirocycle.

In an embodiment, the compound of Formula I or II has the structure of Formula IIa:

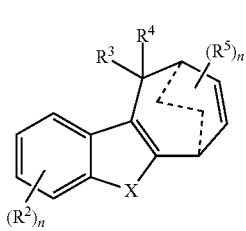

(IIa)

wherein dashed bonds, independently, are present or absent;

X is NR¹;

Rᵃ and Rᵇ are absent, or independently selected from hydrogen, alkyl, hydroxyl, and hydroxyalkyl;

R¹ is hydrogen, alkyl, alkenyl, alkynyl, aryl, benzyl, or alkylene optionally substituted with aryl;

R² is, for each occurrence, independently selected from the group consisting of hydrogen, halogen, haloalkyl, alkyl, alkoxy, alkenyl, alkynyl, cycloalkyl, cycloalkenyl, and —CO₂R⁸;

R³ is selected from the group consisting of hydrogen, halogen, haloalkyl, alkyl, alkoxy, alkenyl, alkynyl, cycloalkyl, cycloalkenyl, Het, —CO₂R⁸, aryl, and aryl substituted with alkoxy or haloalkyl;

R⁴ is selected from the group consisting of hydrogen, halogen, haloalkyl, alkyl, alkoxy, alkenyl, alkynyl, cycloalkyl, cycloalkenyl, Het, —CO₂R⁸, aryl, and aryl substituted with alkoxy or haloalkyl;

or, R³ and R⁴ together may combine to form a 4, 5, or 6 member cycloalkyl;

R⁵ is, for each occurrence, independently selected from the group consisting of hydrogen, halogen, haloalkyl, alkyl, alkoxy, alkenyl, alkynyl, cycloalkyl, oxo, cycloalkenyl, Het, aryl, substituted aryl.

In an embodiment, the compound of Formula IIa has a structure selected from the following:

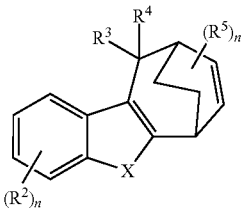

(IIa¹)

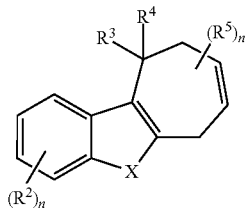

(IIa²)

wherein, X is NR¹;

R¹ is hydrogen, alkyl, alkenyl, alkynyl, aryl, benzyl, or alkylene optionally substituted with aryl;

R² is, for each occurrence, independently selected from the group consisting of hydrogen, halogen, haloalkyl, alkyl, alkoxy, alkenyl, alkynyl, cycloalkyl, cycloalkenyl, and —CO₂R⁸;

R³ is selected from the group consisting of hydrogen, halogen, haloalkyl, alkyl, alkoxy, alkenyl, alkynyl, cycloalkyl, cycloalkenyl, Het, —CO₂R⁸, aryl; aryl substituted with alkoxy, haloalkyl;

R⁴ is selected from the group consisting of hydrogen, halogen, haloalkyl, alkyl, alkoxy, alkenyl, alkynyl, cycloalkyl, cycloalkenyl, Het, —CO₂R⁸, aryl; aryl substituted with alkoxy, haloalkyl;

or, R³ and R⁴ together may combine to form a 4, 5, or 6 member cycloalkyl;

R⁵ is, for each occurrence, independently selected from the group consisting of hydrogen, halogen, haloalkyl, alkyl, alkoxy, alkenyl, alkynyl, cycloalkyl, cycloalkenyl, Het, aryl, substituted aryl, oxo; wherein n is 0, 1, 2, 3, or 4.

In an embodiment, the compound of Formula I or Formula II has the structure of Formula IIb:

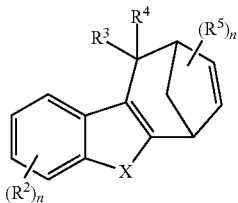

(IIb)

wherein X is NR$^1$;

R$^1$ is hydrogen, alkyl, alkenyl, alkynyl, aryl, benzyl, or alkylene optionally substituted with aryl;

R$^2$ is, for each occurrence, independently selected from the group consisting of hydrogen, halogen, haloalkyl, alkyl, alkoxy, alkenyl, alkynyl, cycloalkyl, cycloalkenyl, and —CO$_2$R$^8$;

R$^3$ is selected from the group consisting of hydrogen, halogen, haloalkyl, alkyl, alkoxy, alkenyl, alkynyl, cycloalkyl, cycloalkenyl, Het, —CO$_2$R$^8$, aryl; aryl substituted to with alkoxy, haloalkyl;

R$^4$ is selected from the group consisting of hydrogen, halogen, haloalkyl, alkyl, alkoxy, alkenyl, alkynyl, cycloalkyl, cycloalkenyl, Het, —CO$_2$R$^8$, aryl; aryl substituted with alkoxy, haloalkyl;

or, R$^3$ and R$^4$ together may combine to form a 4, 5, or 6 member cycloalkyl;

R$^5$ is, for each occurrence, independently selected from the group consisting of hydrogen, halogen, haloalkyl, alkyl, alkoxy, alkenyl, alkynyl, cycloalkyl, cycloalkenyl, Het, aryl, substituted aryl, and oxo; and n is 0, 1, 2, 3 or 4.

In an embodiment, the compound of Formula IIb is selected from compounds IIb$^1$ and IIb$^2$:

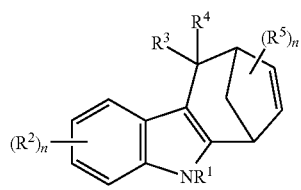

(IIb$^1$)

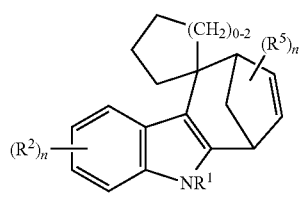

(IIb$^2$)

wherein R$^1$ is hydrogen, alkyl, alkenyl, alkynyl, aryl, benzyl, or alkylene optionally substituted with aryl;

R$^2$ is, for each occurrence, independently selected from the group consisting of hydrogen, halogen, haloalkyl, alkyl, alkoxy, alkenyl, alkynyl, cycloalkyl, cycloalkenyl, and —CO$_2$R$^8$;

R$^3$ is selected from the group consisting of hydrogen, halogen, haloalkyl, alkyl, alkoxy, alkenyl, alkynyl, cycloalkyl, cycloalkenyl, Het, —CO$_2$R$^8$, aryl; aryl substituted with alkoxy, haloalkyl;

R$^4$ is selected from the group consisting of hydrogen, halogen, haloalkyl, alkyl, alkoxy, alkenyl, alkynyl, cycloalkyl, cycloalkenyl, Het, —CO$_2$R$^8$, aryl; aryl substituted with alkoxy, haloalkyl;

R$^5$ is, for each occurrence, independently selected from the group consisting of hydrogen, halogen, haloalkyl, alkyl, alkoxy, oxo, alkenyl, alkynyl, cycloalkyl, cycloalkenyl, Het, aryl, substituted aryl, oxo, and wherein n is 0, 1, 2 or 4.

In an embodiment, the compound of Formula I or Formula II has the structure of Formula IIc$^1$:

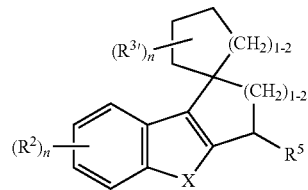

(IIc$^1$)

wherein X is NR$^1$;

R$^1$ is hydrogen, alkyl, alkenyl, alkynyl, aryl, benzyl, or alkylene optionally substituted with aryl;

R$^2$ is, for each occurrence, independently selected from the group consisting of hydrogen, halogen, haloalkyl, alkyl, alkoxy, alkenyl, alkynyl, cycloalkyl, cycloalkenyl, and —CO$_2$R$^8$;

R$^{3'}$ is, for each occurrence, independently selected from the group consisting of hydrogen, halogen, haloalkyl, alkyl, alkoxy, alkenyl, alkynyl, cycloalkyl, cycloalkenyl, Het, aryl, —NHR$^7$, —NHHet, —NHR$^7$Het, oxo, —OR$^8$, —O-aryl, —OHet, —R$^7$OR$^8$, —NR$^8$R$^9$, —NR$^8$-aryl, —R$^7$NR$^8$R$^9$, —R$^7$NR$^8$-aryl, —R$^7$C(O)R$^8$, —C(O)R$^8$, —CO$_2$R$^8$, —R$^7$CO$_2$R$^8$, —C(O)NR$^8$R$^9$, —C(O)aryl, —C(O)NR$^8$aryl, —C(O)Het, —C(O)NHR$^7$Het, —R$^7$C(O)NR$^8$R$^9$, —C(S)NR$^8$R$^9$, —R$^7$C(S)NR$^8$R$^9$, —R$^7$(NH)NR$^8$R$^9$, —C(NH)NR$^8$R$^9$, —R$^7$C(NH)NR$^8$R$^9$, —S(O)$_2$NR$^8$R$^9$, —S(O)$_2$NR$^8$aryl, —R$^7$SO$_2$NHCOR$^8$, —R$^7$SO$_2$NR$^8$R$^9$, —R$^7$SO$_2$R$^8$, —S(O)$_m$R$^8$, cyano, nitro, and azido; wherein two R$^{3'}$ may combine to form a 5- or 6-membered ring;

R$^5$ is selected from the group consisting of hydrogen, halogen, haloalkyl, alkyl, alkoxy, alkenyl, alkynyl, cycloalkyl, cycloalkenyl, Het, aryl, aryl substituted with alkyl or —OCOR$^1$, and oxo; and n is 0, 1, 2, 3 or 4.

In an embodiment, the compound of Formula I or Formula II has the structure of Formula IIc$^2$:

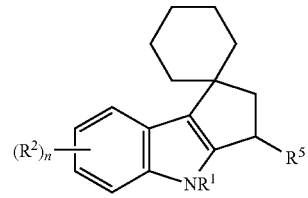

(IIc$^2$)

wherein R$^1$ is hydrogen, alkyl, alkenyl, alkynyl, aryl, benzyl, or alkylene optionally substituted with aryl;

R$^2$ is, for each occurrence, independently selected from the group consisting of hydrogen, halogen, haloalkyl, alkyl, alkoxy, alkenyl, alkynyl, cycloalkyl, cycloalkenyl, and —CO$_2$R$^8$;

R$^5$ is selected from the group consisting of hydrogen, halogen, haloalkyl, alkyl, alkoxy, alkenyl, alkynyl, cycloalkyl, cycloalkenyl, Het, aryl, aryl substituted with alkyl or —OCOR$^1$, and oxo; and n is 0, 1, 2, 3 or 4.

In an embodiment, the compound of Formula I or Formula II has the structure of Formula IId¹:

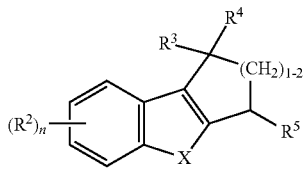

(IId¹)

wherein X is NR¹;
R¹ is hydrogen, alkyl, alkenyl, alkynyl, aryl, benzyl, or alkylene optionally substituted with aryl;
R² is, for each occurrence, independently selected from the group consisting of hydrogen, halogen, haloalkyl, alkyl, alkoxy, alkenyl, alkynyl, cycloalkyl, cycloalkenyl, and —CO₂R⁸;
R³ is selected from the group consisting of hydrogen, halogen, haloalkyl, alkyl, alkoxy, alkenyl, alkynyl, cycloalkyl, cycloalkenyl, Het, —CO₂R⁸, aryl; aryl substituted with alkoxy, haloalkyl;
R⁴ is selected from the group consisting of hydrogen, halogen, haloalkyl, alkyl, alkoxy, alkenyl, alkynyl, cycloalkyl, cycloalkenyl, Het, —CO₂R⁸, aryl; aryl substituted with alkoxy, haloalkyl;
or, R³ and R⁴ together may combine to form a 4, 5, or 6 member cycloalkyl, aryl, or Het;
R⁵ is selected from the group consisting of hydrogen, halogen, haloalkyl, alkyl, alkoxy, alkenyl, alkynyl, cycloalkyl, cycloalkenyl, Het, aryl, substituted aryl, and oxo; and n is 0, 1, 2, 3 or 4.

In an embodiment, the compound of Formula I or Formula II has the structure of Formula IId²:

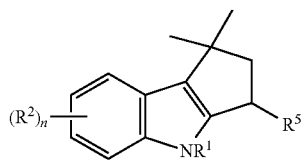

(IId²)

wherein R¹ is hydrogen, alkyl, alkenyl, alkynyl, aryl, benzyl, or alkylene optionally substituted with aryl;
R² is, for each occurrence, independently selected from the group consisting of hydrogen, halogen, haloalkyl, alkyl, alkoxy, alkenyl, alkynyl, cycloalkyl, cycloalkenyl, —CO₂R⁸;
R⁵ is selected from the group consisting of halogen, haloalkyl, alkyl, alkoxy, alkenyl, alkynyl, cycloalkyl, cycloalkenyl, Het, aryl, substituted aryl, oxo; and n is 0, 1, 2, 3 or 4.

In an embodiment, the compound of Formula I or Formula II has the structure of Formula IIe:

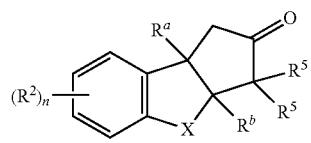

(IIe)

wherein Rᵃ and Rᵇ are absent, or independently selected from hydrogen, alkyl, hydroxyl, hydroxyalkyl; or wherein Rᵃ and Rᵇ together a 5- or 6-membered cycloalkyl or heterocycloalkyl with one or more heteroatoms independently selected from O or NR¹;
wherein R² is, for each occurrence, independently selected from the group consisting of hydrogen, halogen, haloalkyl, alkyl, alkoxy, alkenyl, alkynyl, cycloalkyl, cycloalkenyl, and —CO₂R⁸;
R⁵ is, for each occurrence, independently selected from the group consisting of hydrogen, halogen, haloalkyl, alkyl, alkoxy, alkenyl, alkynyl, cycloalkyl, cycloalkenyl, Het, aryl, substituted aryl, oxo; and n is 0, 1, 2, 3 or 4.

In an embodiment, the compound of Formula I or Formula III has the structure of Formula IIIa:

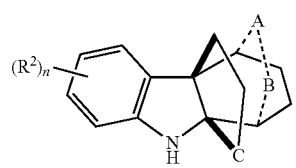

(IIIa)

wherein dashed bonds, independently, are present or absent;
A and B are independently O, NR¹, CH₂, CH(R⁵), C(R⁵)₂, or are absent;
C is O, NR¹, CH₂, CH(R⁵), or C(R⁵)₂,
R² is, for each occurrence, independently selected from the group consisting of hydrogen, halogen, haloalkyl, alkyl, alkoxy, alkenyl, alkynyl, cycloalkyl, cycloalkenyl, —CO₂R⁸; and n is 0, 1, 2, 3 or 4.

In an embodiment, the compound of Formula I or Formula III has the structure of Formula IIIb:

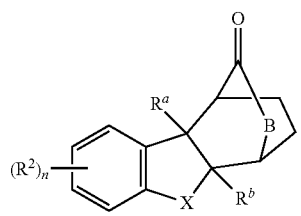

(IIIb)

wherein B is CH₂, CH(R⁵), C(R⁵)₂, O, NR² or is absent;
wherein Rᵃ and Rᵇ are absent, or independently selected from hydrogen, alkyl, hydroxyl, hydroxyalkyl, aryl, benzyl, and amino; or wherein Rᵃ and Rᵇ may combine to form a 5- or 6-membered cycloalkyl or heterocycloalkyl with one or more heteroatoms independently selected from O or NR¹;
R² is, for each occurrence, independently selected from the group consisting of hydrogen, halogen, haloalkyl, alkyl, alkoxy, alkenyl, alkynyl, cycloalkyl, cycloalkenyl, —CO₂R⁸; and n is 0, 1, 2, 3 or 4.

In an embodiment, the compound of Formula I or Formula IV has the structure of Formula IVa:

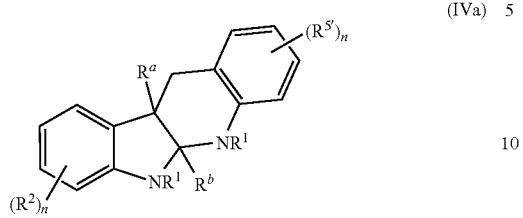
(IVa)

wherein $R^a$ and $R^b$ are absent, or independently selected from hydrogen, alkyl, hydroxyl, hydroxyalkyl, aryl, benzyl, and amino; or wherein $R^a$ and $R^b$ may combine to form a 5- or 6-membered cycloalkyl or heterocycloalkyl with one or more heteroatoms independently selected from O or $NR^1$;

$R^1$, for each occurrence, is independently selected from the group consisting of hydrogen, alkyl, alkenyl, alkynyl, aryl, benzyl, or alkylene optionally substituted with aryl;

$R^2$ is, for each occurrence, is independently selected from the group consisting of hydrogen, halogen, haloalkyl, alkyl, alkoxy, alkenyl, alkynyl, cycloalkyl, cycloalkenyl, and —$CO_2R^8$;

$R^{5'}$ is, for each occurrence, independently selected from the group consisting of halogen, haloalkyl, alkyl, alkoxy, alkenyl, alkynyl, cycloalkyl, cycloalkenyl, Het, aryl, —$NHR^7$, —NHHet, —$NHR^7$Het, oxo, —$OR^8$, —O-aryl, —OHet, —$R^7OR^8$, —$NR^8R^9$, —$NR^8$-aryl, —$R^7NR^8R^9$, —$R^7NR^8$-aryl, —$R^7C(O)R^8$, —$C(O)R^8$, —$CO_2R^8$, —$R^7CO_2R^8$, —$C(O)NR^8R^9$, —C(O)aryl, —$C(O)NR^8$aryl, —C(O)Het, —$C(O)NHR^7$Het, —$R^7C(O)NR^8R^9$, —C(S)$NR^8R^9$, —$R^7C(S)NR^8R^9$, —$R^7(NH)NR^8R^9$, —C(NH)$NR^8R^9$, —$R^7C(NH)NR^8R^9$, —$S(O)_2NR^8R^9$, —$S(O)_2NR^8$aryl, —$R^7SO_2NHCOR^8$, —$R^7SO_2NR^8R^9$, —$R^7SO_2R^8$, —$S(O)_mR^8$, cyano, nitro, and azido; and n is 0, 1, 2, 3 or 4.

In certain embodiments, the compound of the invention has the physical form of an oil, a wax, an amorphous solid, or a crystalline solid.

In an embodiment, the compound of the invention is selected from Table 1, or a pharmaceutically acceptable stereoisomer, isotope, solvate or salt thereof.

TABLE 1

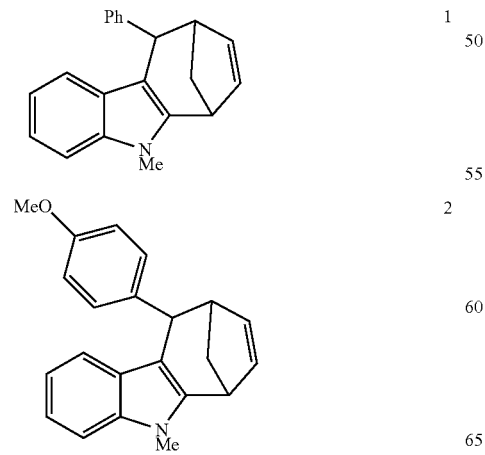

| | |
|---|---|
| 1 | (Ph structure) |
| 2 | (MeO structure) |

TABLE 1-continued

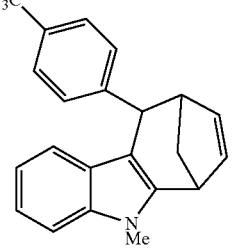

3

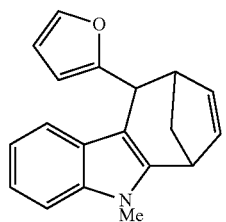 [SMILES: Cn1c2c(c3ccccc31)C(c1ccco1)C1C=CC2C1]

4

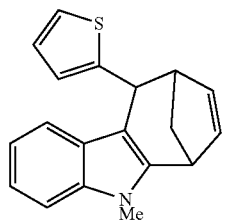 [SMILES: Cn1c2c(c3ccccc31)C(c1cccs1)C1C=CC2C1]

5

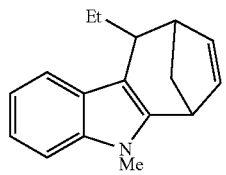 [SMILES: CCC1c2c(n(C)c3ccccc23)C2C=CC1C2]

6

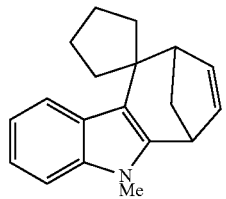 [SMILES: Cn1c2c(c3ccccc31)C1(CCCC1)C1C=CC2C1]

7

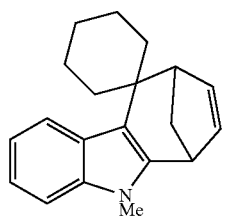 [SMILES: Cn1c2c(c3ccccc31)C1(CCCCC1)C1C=CC2C1]

8

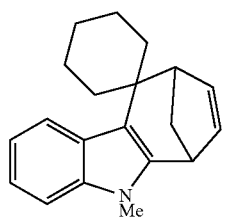 [SMILES: Cn1c2c(c3ccccc31)C1(CCCCC1)C1C=CC2C1]

9

TABLE 1-continued
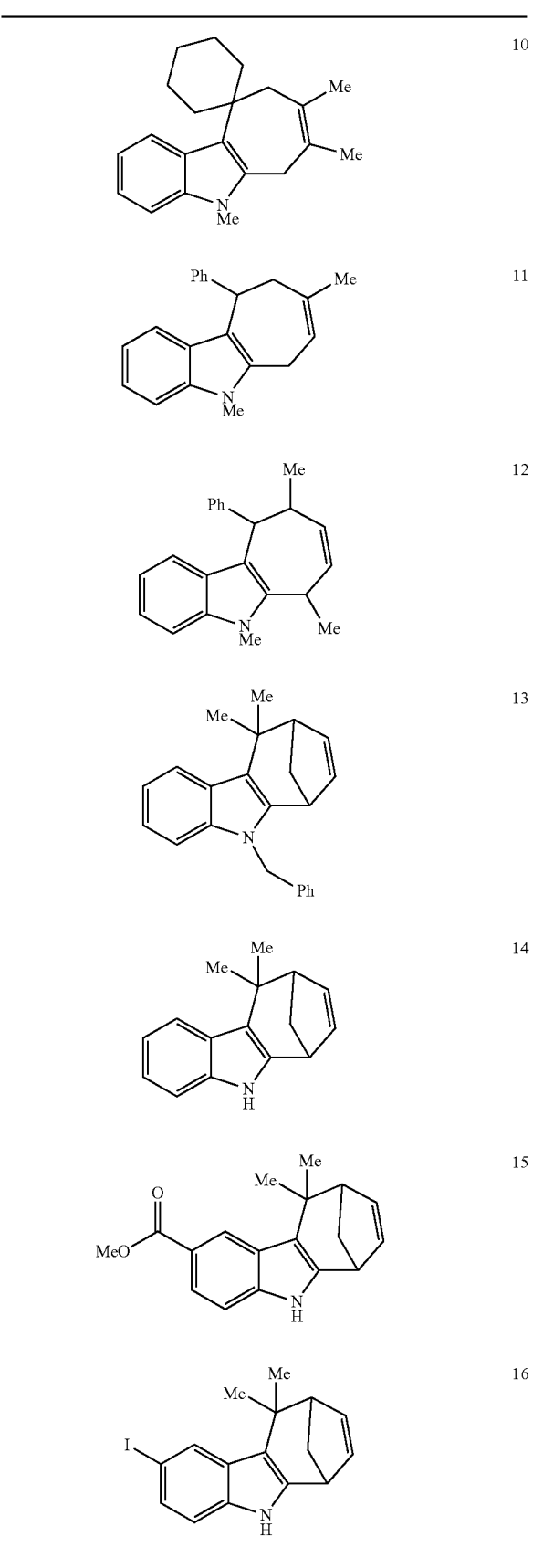
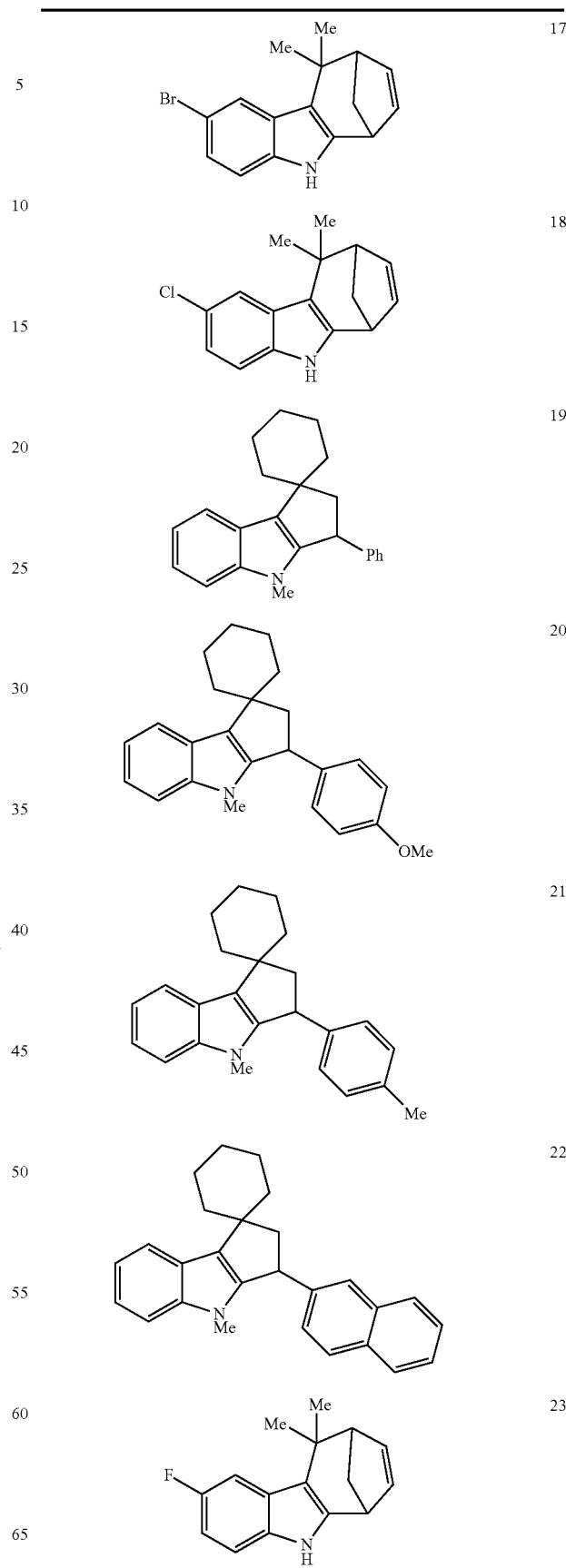

TABLE 1-continued
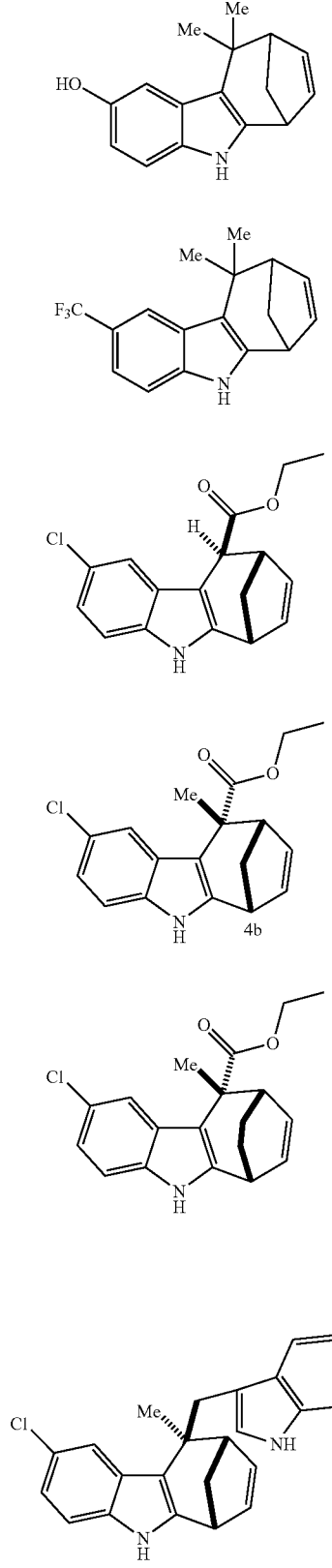
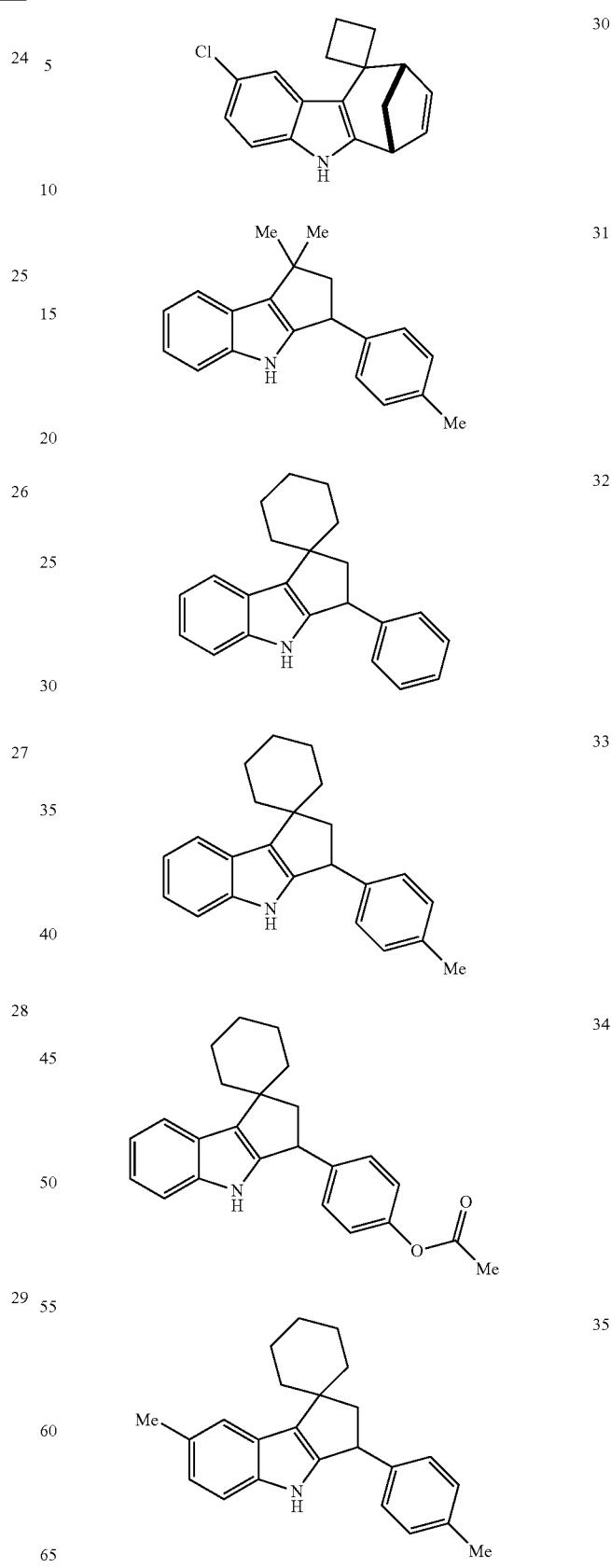

TABLE 1-continued
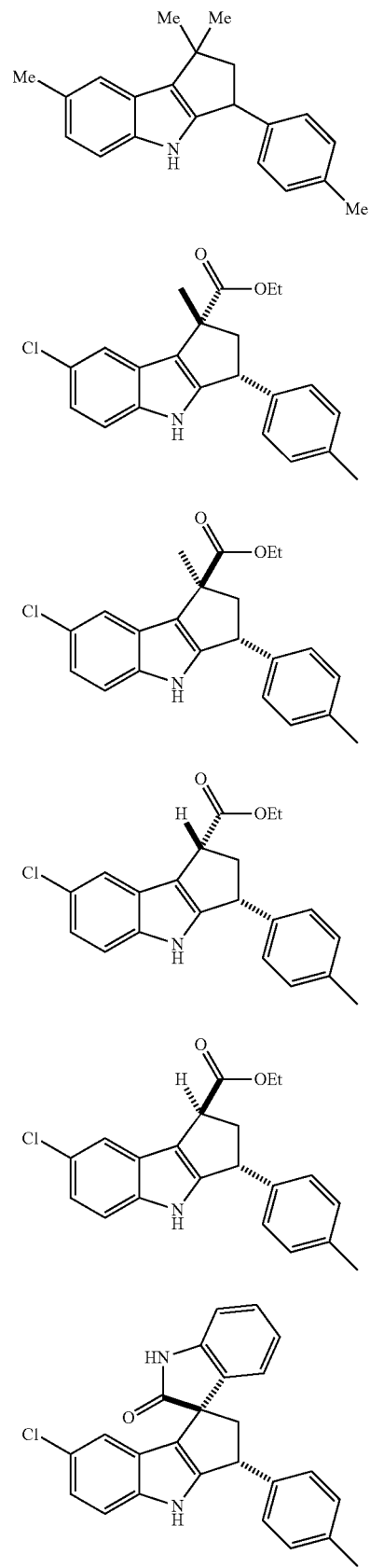
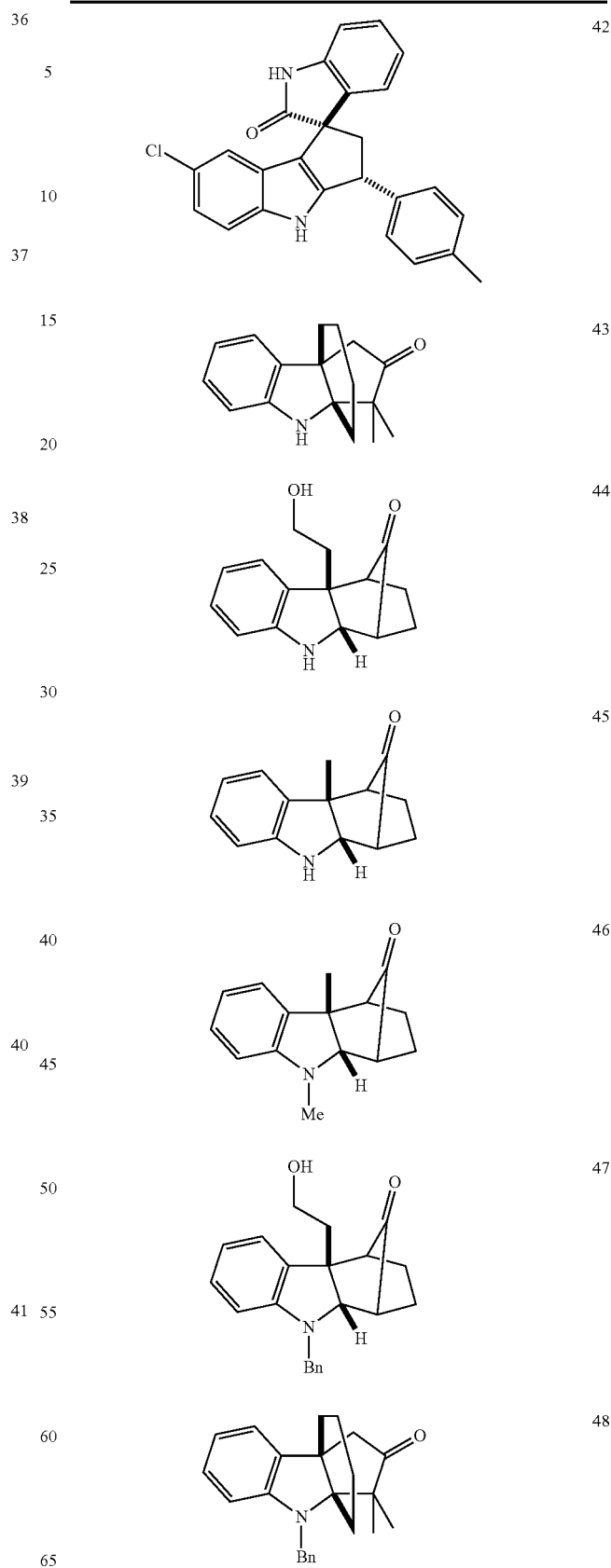

TABLE 1-continued
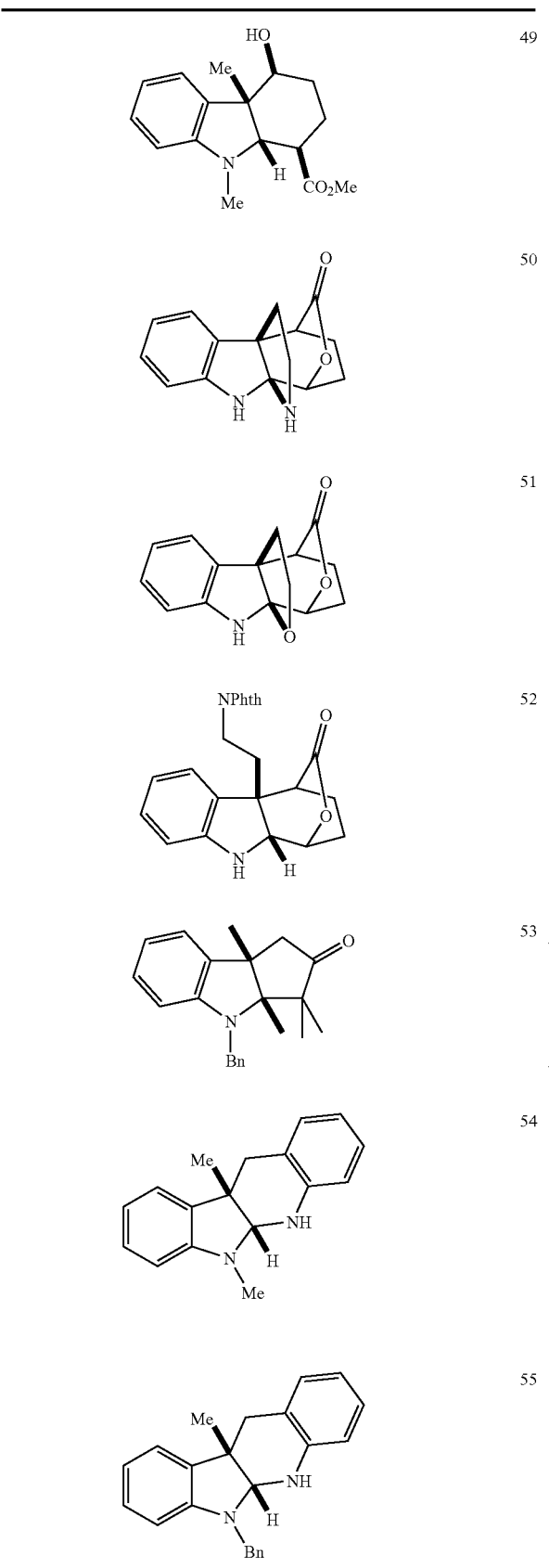
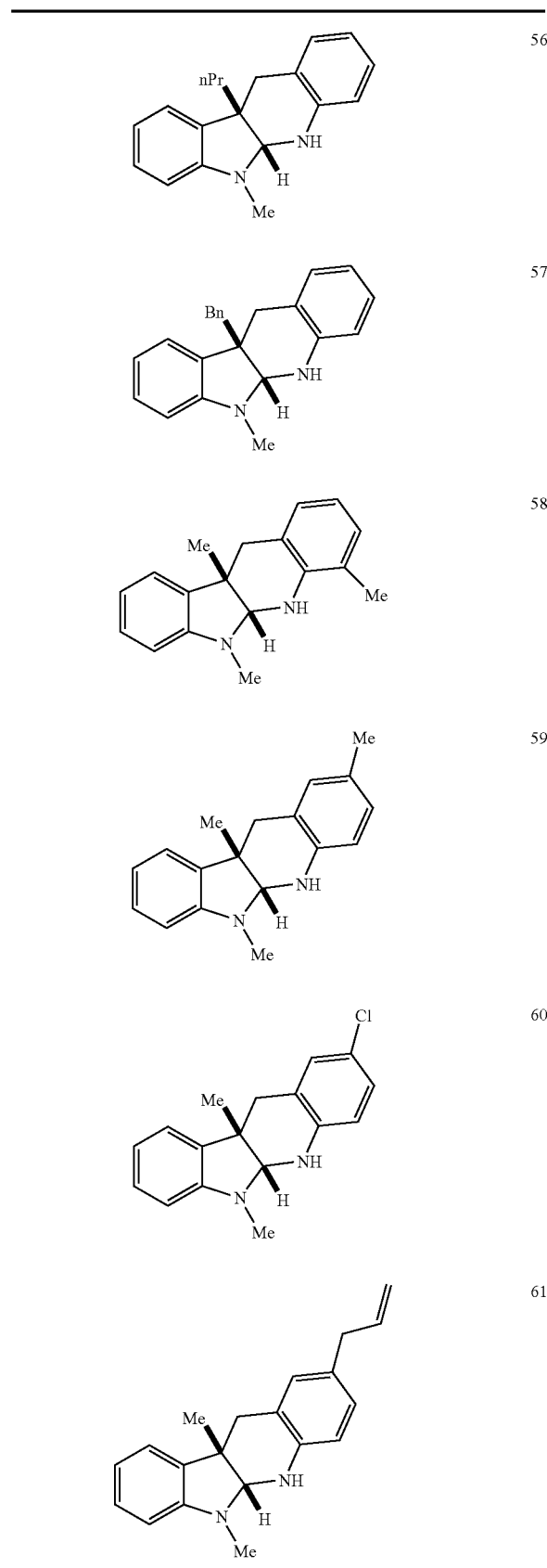

TABLE 1-continued

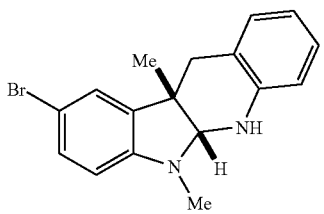 [SMILES: CN1c2ccc(Br)cc2[C@]2(C)Cc3ccccc3N[C@H]12]

62

In an embodiment, the compound of the invention does not affect the binding of PCSK9 to LDLR. For example, administration to a subject of the compound of the invention may not result in increased levels of PCSK9 binding to LDLR, or administration to a subject of the compound of the invention may not result in decreased levels of PCSK9 binding to LDLR.

In an embodiment, the compound of the invention does not affect albumin level. For example, administration to a subject of the compound of the invention may not result in increased albumin levels, or administration to a subject of the compound of the invention may not result in decreased albumin levels.

In an embodiment, the compound of the invention does not affect apoE level. For example, administration to a subject of the compound of the invention may not result in increased apoE levels, or administration to a subject of the compound of the invention may not result in decreased apoE levels.

In an embodiment, the compound of the invention inhibits PCSK9 mRNA. For example, the compound of the invention may inhibit PCSK9 mRNA transcription and/or production.

In an embodiment, the compound of the invention does not affect hepatic transaminase levels. For example, administration to a subject of the compound of the invention may not result in increased hepatic transaminase levels, or administration to a subject of the compound of the invention may not result in decreased hepatic transaminase levels.

Pharmaceutical Compositions

A pharmaceutical composition of a compound of the invention is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), and transmucosal administration (e.g., rectally or vaginally). Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The instant application further relates to storage stable forms containing compounds of the invention, e.g., lyophilates, suspensions, and buffered or temperature stable compositions.

Dosages and Modes of Administration

The compounds of the invention may be administered using any amount and any route of administration effective for the indicated purpose (e.g., as indicated in any one of several aspects and embodiments provided herein). Thus, the expression "effective amount" as used herein, refers to a sufficient amount of agent to achieve the indicated purpose (e.g., to reduce the level of PCSK9, to reduce the level of LDL, to increase the level of LDLR, to treat or prevent a condition associated with elevated PCSK9 levels, or to treat or prevent a condition associated with elevated LDL levels). The exact amount required will vary from subject to subject, depending on the species, age, and general condition of the subject, the severity of the diseases, the particular compound, its mode of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds of the invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety).

Definitions

As used herein, the term "alkyl" refers to a fully saturated branched or unbranched hydrocarbon moiety. Preferably the alkyl comprises 1 to 20 carbon atoms, 1 to 16 carbon atoms, 1 to 10 carbon atoms, or more preferably 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$ alkyl includes, but is not limited to, methyl, ethyl, propyl, butyl, isopropyl, tert-butyl and isobutyl.

As used herein, the term "alkoxy" refers to —O-alkyl.

The term "alkenyl" refers to a straight or branched chain aliphatic hydrocarbon containing one or more carbon-to-carbon double bonds. Examples include, but are not limited to, vinyl, allyl, and the like. Preferably the alkenyl group comprises 2 to 20 carbon atoms, 2 to 16 carbon atoms, 2 to 10 carbon atoms, 2 to 6 carbon atoms, or 2 to 3 carbon atoms.

The term "alkynyl" refers to a straight or branched chain aliphatic hydrocarbon containing one or more carbon-to-carbon triple bonds. Examples include, but are not limited to, acetylenyl, paropargyl, and the like. Preferably the alkynyl group comprises 2 to 20 carbon atoms, 2 to 16 carbon atoms, 2 to 10 carbon atoms, 2 to 6 carbon atoms, or 2 to 3 carbon atoms.

The term "cycloalkyl" refers to an optionally substituted non-aromatic cyclic hydrocarbon ring, which optionally includes an alkylene linker through which the cycloalkyl may be attached. Exemplary "cycloalkyl" groups include, but are not limited to, cyclopropyl, cyclobutyl, cyclopentyl, cyclohexyl, cycloheptyl, and substituted versions thereof. As used herein, the term "cycloalkyl" includes an optionally substituted fused polycyclic hydrocarbon saturated ring and aromatic ring system, namely polycyclic hydrocarbons with less than maximum number of non-cumulative double bonds, for example where a saturated hydrocarbon ring (such as a cyclopentyl ring) is fused with an aromatic ring (herein "aryl," such as a benzene ring) to form, for example, groups such as indane.

The term "cycloalkenyl" refers to an optionally substituted non-aromatic cyclic hydrocarbon ring containing one or more carbon-to-carbon double bonds which optionally includes an alkylene linker through which the cycloalkenyl may be attached. Exemplary "cycloalkenyl" groups include, but are not limited to, cyclopropenyl, cyclobutenyl, cyclopentenyl, cyclohexenyl, cycloheptenyl, and substituted versions thereof.

The term "aryl" refers to an optionally substituted benzene ring or to an optionally substituted fused benzene ring system, for example anthracene, phenanthrene, or naphthalene ring systems. Examples of "aryl" groups include, but are not limited to, phenyl, 2-naphthyl, 1-naphthyl, and the like.

The term "heteroaryl" (i.e., "Het") refers to an optionally substituted monocyclic five to seven membered aromatic ring, or to an optionally substituted fused bicyclic aromatic ring system comprising two of such aromatic rings, one of which may be aryl. These heteroaryl rings contain one or more nitrogen, sulfur, and/or oxygen atoms, where N-oxides, sulfur oxides, and dioxides are permissible heteroatom substitutions. Examples of "heteroaryl" groups used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, benzimidizolyl, imidazopyridinyl, pyrazolopyridinyl, pyrazolopyrimidinyl, and the like.

As used herein, the term "amino" (alone or in combination with another term(s)) refers to —$NH_2$, or a mono- or disubstituted derivative, i.e., a secondary or tertiary amine.

As used herein, the term "halogen" refers to fluorine, chlorine, bromine, iodine or astatine. In this respect, the term "haloalkyl" refers to an alkyl group, as defined herein, that is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, e.g., fluoro, chloro, bromo, iodo and astatino. The term "haloalkyl"

should be interpreted to include such substituents as perfluoroalkyl groups and the like.

In some embodiments, the alkyl, alkenyl, alkynyl, cycloalkyl, cycloalkenyl, amino, aryl, and heteroaryl groups described herein are optionally substituted.

As used herein throughout the specification, the phrase "optionally substituted" or variations thereof denote an optional substitution, including multiple degrees of substitution, with one or more substituent group. The phrase should not be interpreted so as to be imprecise or duplicative of substitution patterns herein described or depicted specifically. Rather, those of ordinary skill in the art will appreciate that the phrase is included to provide for obvious modifications, which are encompassed within the scope of the appended claims.

Exemplary optional substituent groups include acyl; alkyl; alkenyl; alkynyl; alkylsulfonyl; alkoxy; alkoxycarbonyl; cyano; halogen; haloalkyl; hydroxy; nitro; oxo; aryl, which may be further substituted with acyl, alkoxy, alkyl, alkenyl, alkynyl, alkylsulfonyl, cyano, halogen, haloalkyl, hydroxy, oxo, or nitro; heteroaryl, which may be further substituted with acyl, alkoxy, alkyl, alkenyl, alkynyl, alkylsulfonyl, cyano, halogen, haloalkyl, hydroxy, oxo, or nitro; arylsulfonyl, which may be further substituted with acyl, alkoxy, alkyl, alkenyl, alkynyl, alkylsulfonyl, cyano, halogen, haloalkyl, hydroxy, or nitro; heteroarylsulfonyl, which may be further substituted with acyl, alkoxy, alkyl, alkenyl, alkynyl, alkylsulfonyl, cyano, halogen, haloalkyl, hydroxy, oxo, or nitro; aryloxy, which may be further substituted with acyl, alkoxy, alkyl, alkenyl, alkynyl, alkylsulfonyl, cyano, halogen, haloalkyl, hydroxy, or nitro; heteroaryloxy, which may be further substituted with acyl, alkoxy, alkyl, alkenyl, alkynyl, alkylsulfonyl, cyano, halogen, haloalkyl, hydroxy, or nitro; or aryloxycarbonyl, which may be further substituted with acyl, alkoxy, alkyl, alkenyl, alkynyl, alkylsulfonyl, cyano, halogen, haloalkyl, hydroxy, phthalimidyl, or nitro.

For example, an optionally substituted alkyl group encompasses hydroxyalkyl, alkoxyalkyl, benzyl, and the like.

As used herein, the dashed bonds may be independently present or absent. The number of bonds arising from the entirety of dashed bonds in a given structure may, where four dashed bonds are shown, comprise no bonds, one bond, two bonds, three bonds, or four bonds; where three dashed bonds are shown, comprise no bonds, one bond, two bonds, or three bonds.

Compounds of the invention may be provided as mixtures of stereoisomers as well as purified enantiomers or enantiomerically/diastereomerically enriched mixtures.

As used herein, the singular form "a", "an", and "the" includes plural references unless indicated otherwise. The term "plurality" refers to two or more of anything, such as cells. For the purposes of the present invention, the terms "a", "an" or "the" refers to one or more of anything, such as a cell or the cell or an antigen or the antigen. For the purpose of the present invention, a plurality of anything may be homogenous or heterogeneous.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

The term proprotein convertase subtilisin kexin type 9 (PCSK9), also known as neural apoptosis-regulated convertase (NARC-1), as used herein, refers to any form of PCSK9 and variants thereof that retain at least part of the activity of PCSK9. Unless indicated differently, such as by specific reference to human PCSK9, PCSK9 includes all mammalian species of native sequence PCSK9, e.g., human, canine, feline, equine, and bovine.

The term "PCSK9 activity" as used herein encompasses any "biological activity of PCSK9" and/or "biological effect elicited by PCSK9". In one embodiment, PCSK9 activity includes the ability of PCSK9 to interact or bind to a substrate or receptor. In another embodiment, the biological activity of PCSK9 is the ability of PCSK9 to bind to a LDL-receptor (LDLR). In yet another embodiment, PCSK9 binds to and catalyzes a reaction involving LDLR. In certain embodiments, PCSK9 activity includes the ability of PCSK9 to decrease or reduce the availability of LDLR. In certain embodiments, the biological activity of PCSK9 includes the ability of PCSK9 to increase the amount of LDL in a subject. In certain embodiments, the biological activity of PCSK9 includes the ability of PCSK9 to decrease the amount of LDLR that is available to bind to LDL in a subject. In certain embodiments, the biological activity of PCSK9 includes the ability of PCSK9 to decrease the amount of LDLR that is available to bind to LDL. In certain embodiments, biological activity of PCSK9 includes any biological activity resulting from PCSK9 signaling. In yet another embodiment, biological activity of PCSK9 encompasses a PCSK9 secretory pathway. In yet another embodiment, biological effect elicited by PCSK9 may be associated with any of foregoing conditions disclosed herein.

As used herein, a "PCSK9 inhibitor" or a compound or a composition thereof that "inhibits" PCSK9 activity refers to a compound that is able to inhibit a biological activity of PCSK9 or a biological effect elicited by PCSK9. In some embodiment, downstream pathway(s) mediated by PCSK9 signaling, including PCSK9-mediated down-regulation of the LDLR, and PCSK9-mediated decrease in LDL blood clearance are inhibited. Such compound may block, antagonize, suppress, reduce, decrease, or neutralize PCSK9 activity in any meaningful degree determined by an ordinary medical practitioner or skilled person in the art.

The term "reduce" in the context of, but not limited to, PCSK9 level or levels, and/or low density lipoprotein level or levels, means a statistically significant decrease in such level. The decrease can be, for example, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, and is preferably down to a level accepted as within the range of normal for a subject without any of foregoing disorders. Alternatively, the degree of decrease may be measured in terms of a reduction of a parameter that is functionally linked to PCSK9 and/or LDL level, e.g., an expression level of a gene associated with changes of cholesterol level.

As described herein, one or more of "active agents" is a therapeutically effective agent that can be simultaneously, sequentially, non-simultaneously and/or separately administered with the compound 34 (B004) or a pharmaceutical composition thereof by the same or different means of administration. In certain embodiments, active agents are the agents used to treat conditions associated with high cholesterol. In another embodiment, active agents are the agents used to treat any of foregoing conditions described herein. In certain embodiment, active agents are the agents that allows for mitigation of undesirable side-effects the methods of treatment described herein.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

"Treat," "treatment," or "treating," as used herein, relates to the application or administration of a therapeutic agent, i.e., a compound of the invention, to a subject, or application or administration of a therapeutic agent to an isolated tissue or cell line from a subject, who has a disease or disorder, a symptom of a disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

As used herein, the term "prevent" or "prevention" means that no disorder or disease has developed if none had yet occurred, or that no further disorder or disease has developed if there had already been development of the disorder or disease.

As used herein, the term "subject" refers to a human or a non-human mammal. Non-human mammals include, for example, livestock and pets, such as ovine, bovine, porcine, canine, feline and murine mammals. In a particular embodiment, the subject is a mammal. In another particular embodiment, the subject is human.

A "diabetic condition" includes, but is not limited to, type 1 diabetes, type 2 diabetes, gestational diabetes, latent autoimmune diabetes in adults (LADA), Maturity Onset Diabetes of the Young (MODY) and Neonatal Diabetes Mellitus (NDM). A diabetic condition refers to a condition in which blood glucose levels are higher than the normal blood glucose range for a subject without foregoing non-limiting exemplary diabetic conditions. The normal blood glucose range may be determined by an ordinary medical practitioner or a skilled person in the art, and may vary depending on factors known in the art, e.g., administration of other agents that affect blood glucose levels.

A "prediabetic condition" as described herein means a blood glucose level in a subject is higher than the range of normal for a subject without any of foregoing non-limiting exemplary diabetic conditions, yet not high enough to be classified as any of foregoing non-limiting exemplary diabetic conditions. An ordinary medical practitioner or a skilled person in the art may diagnose a subject with a prediabetic condition by using a diagnostic test or a combination thereof that are well-known in the art, e.g., glycated hemoglobin (A1C) test and fasting blood sugar test.

As used herein, a condition "associated" with any of foregoing diseases or an "association" with any of foregoing diseases may be determined by an ordinary medical practitioner or a skilled person in the art. Signs and symptoms of such association may be closely correlated with signs and/or symptoms of any of foregoing diseases disclosed herein. Signs and symptoms of such association may not be closely correlated with signs and/or symptoms of any of foregoing diseases disclosed herein. In some embodiment, a condition associated with any of foregoing diseases maybe a primary association to any of foregoing diseases disclosed herein. In some embodiment, a condition associated with any of foregoing diseases maybe a secondary association to any of foregoing diseases disclosed herein.

The term "hypercholesterolemia," as used herein, refers to a condition in which cholesterol levels are elevated above a desired level. In certain embodiments, the LDL-cholesterol level is elevated above the desired level. In certain embodiments, the plasma LDL-cholesterol levels are elevated above the desired level. In certain embodiments, hypercholesterolemia may be familial hypercholesterolemia including by way of example heterozygous hypercholesterolemia, homozygous hypercholesterolemia, familial defective apolipoprotein B-100, and polygenic hypercholesterolemia. The desired level range may be determined by an ordinary medical practitioner or a skilled person in the art, and may vary depending on factors known in the art, e.g., administration of other agents that affect cholesterol levels.

The term "atherosclerotic disease" encompasses arteriosclerosis, arteriolosclerosis, and atherosclerosis, and a condition associated with arteriosclerosis, arteriolosclerosis, and atherosclerosis. Non-limiting examples of atherosclerotic diseases are a coronary heart disease, coronary artery disease, peripheral arterial disease, stroke (ischemic and hemorrhagic), angina pectoris, cerebrovascular disease, acute coronary syndrome, or myocardial infarction.

As used herein, the term "in vivo" refers to a process taking place inside a living subject. The term "in vitro" refers to a process taking place outside a living subject.

EXAMPLES

The compounds of Table 1, and methods of making various compounds of Table 1, are disclosed in U.S. Patent Application Publication No. 2015/0057326A1. Representative synthesis and characterization procedures and data are also disclosed in the following publications, which are incorporated herein by reference: (1) Angew. Chem. Int. Ed. 2012, 51, 10390-10393, and corresponding Supporting Information; (2) J. Am. Chem. Soc. 2014, 136, 6288-6296, and corresponding Supporting Information; (3) J. Am. Chem. Soc. 2015, 137, 14861-14864, and corresponding Supporting Information; (4) Nature: Scientific Reports, 6, 28934, 1-14, and corresponding Supporting Information; (5) Tetrahedron 67, 2011, 4327-4332, and corresponding Supporting Information.

Example 1

In vitro studies in human hepatoma cells (HepG2)

1-1) Cell Survival

Figure 4B:
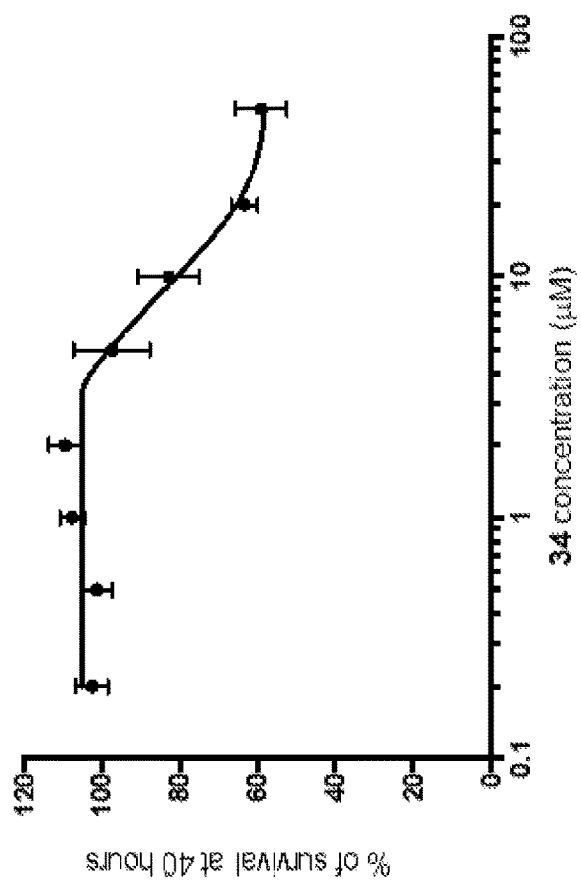
FIGS. 4A-4B show that compound 34 does not affect HepG2 cell survival at concentrations up to 5 µM. Cell survival was measured using MTT (3-(4,5-dimethylthiazol-2-yl)-2,5-diphenyltetrazolium.
Figure 4A:
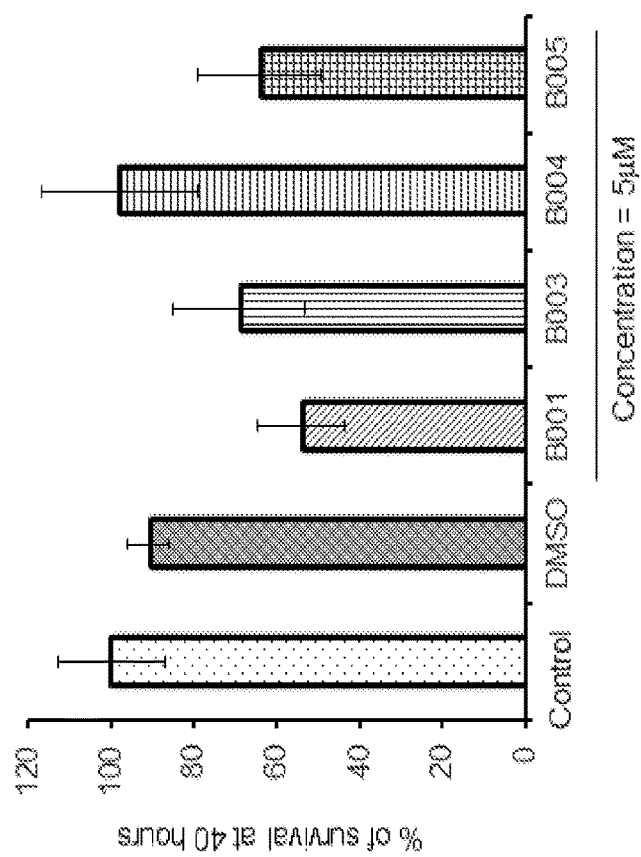

To study the effect of the compound on cell viability we used $1.25 \times 10^5$ HepG2 cells in 96-well culture plates, followed by incubation with media only, media+0.1% DMSO or Media+5 uM of 31/33/34/35 in 0.1% DMSO or with increasing concentration (0.2-50 µM) of 34 in 0.1% DMSO for 40 hours followed by a viability assay knows as MTT. The MTT assay is a colorimetric assay for assessing cell metabolic activity. NAD(P)H-dependent cellular oxidoreductase enzymes may, reflects the number of viable cells present. These enzymes are capable of reducing the tetrazolium dye MTT 3-(4,5-dimethylthiazol-2-yl)-2,5-diphenyltetrazolium bromide to its insoluble formazan, which has a purple color. Tetrazolium dye assays (commonalty known as the MTT assay) is used to measure cytotoxicity (loss of viable cells). See FIGS. 4A-B.

1-2) Secreted PCSK9

Figure 2A:
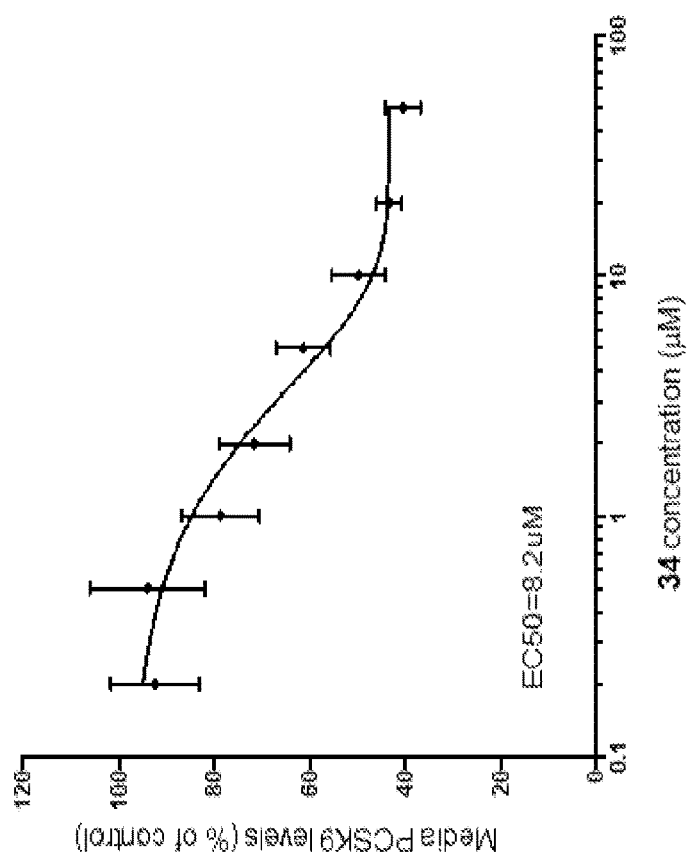
FIGS. 2A-2B show that compound 34 reduces PCSK9 accumulation in media of HepG2 cells. 5 µM of B001 (compound 31), B003 (compound 33), B004 (compound 34) and B005 (compound 35) significantly reduced accumulation of PCSK9 in culture media in a time-dependent and concentration-dependent manner.
Figure 2B:
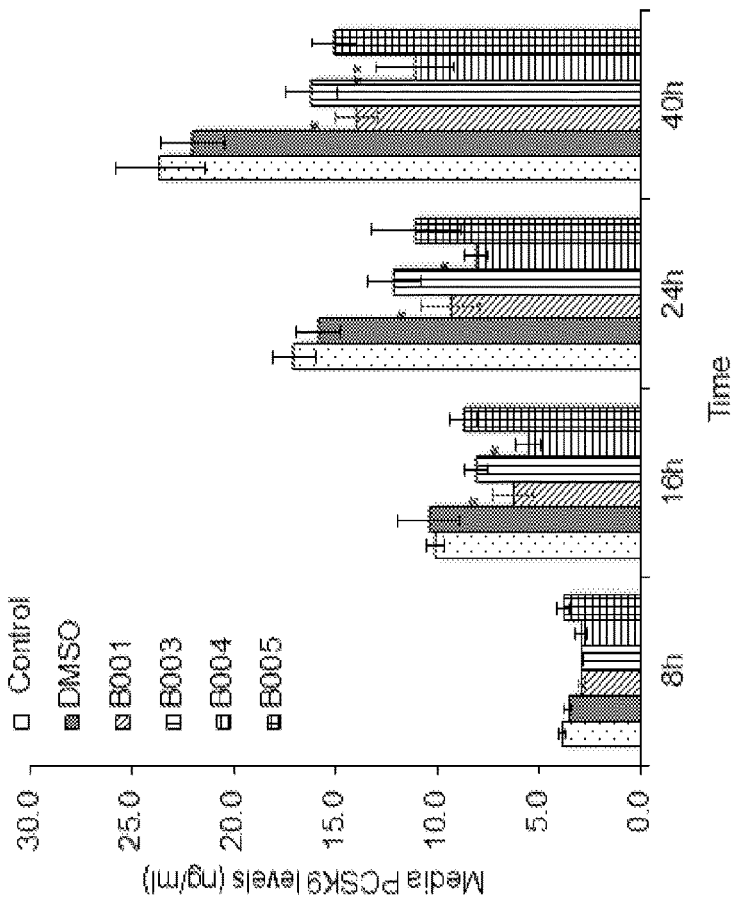
Figure 3:
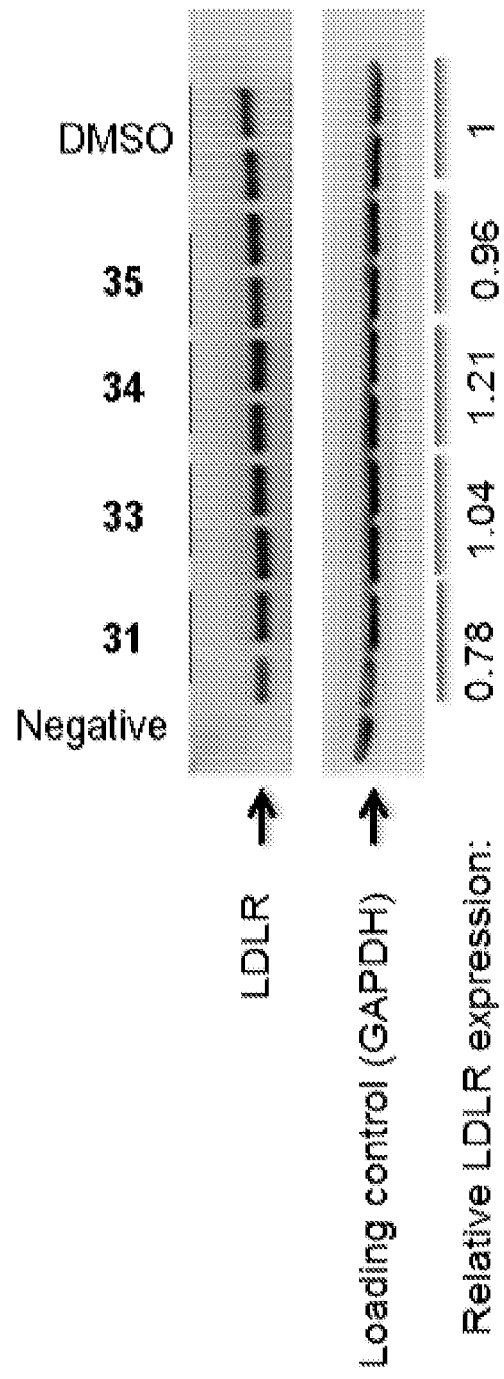
FIG. 3 shows that B004 increases LDLR in HepG2 cells. After 40 hours of incubation with 5 µM compound 34 there is a 21% increase in LDLR protein levels. See Example 1-7.

To study the effect of the compounds on PCSK9 secretion we used $1 \times 10^6$ HepG2 cells in 6-well culture plates, followed by incubation with media only, media+0.1% DMSO or Media+5 uM of 31/33/34/35 in 0.1% DMSO and collection of 50 ul of media at 8, 16, 24 and 40 hours or incubation with increasing concentration (0.2-50 µM) of 34 in 0.1% DMSO for 24 hours and collection of 50 ul of media. The collected media was analyzed for PCSK9 levels using commercially available ELISA kit (MBL-international, catalog # CY-8079) following the manufacturer instruction. See FIGS. 2A-B.

1-3) PCSK9 Detection

To study whether 34 directly interfere with PCSK9 detection we used recombinant PCSK9 (30 ng/ml) was mixed with increasing concentration (0.2-50 µM) of 34 in 0.1% DMSO followed by detection of PCSK9 using commercially available ELISA kit (MBL-international, catalog # CY-8079) following the manufacturer instruction. See FIG. 5A 1-4) PCSK9-LDLR Interaction To study whether increasing concentrations of 34 (0.2-50 µM) directly interfere with PCSK9-LDLR interaction we used a commercially available ELISA kit (MBL-international, catalog # CY-8150) following the manufacturer instruction. See FIG. 5B.

1-5) Intracellular PCSK9 Protein

To study whether 34 affect intracellular PCSK9 levels we used $1 \times 10^6$ HepG2 cells in 6-well culture plates, followed by incubation with media+0.1% DMSO or increasing concentration (0.2-50 uM) of 34 in 0.1% DMSO for 24 hours. After 24 hours media was aspirated, cells were washed with HBSS followed by protein extraction using commercially available RIPA buffer (SIGMA-ALDRICH, catalog #20-188). Protein extracts (20 µg) were used for immunodetection of intracellular PCSK9 (western blot analysis) with a commercially available primary antibody against PCSK9 (MBL-international, catalog # CY-1037), HRP-conjugated secondary antibody (SIGMA-ALDRICH, catalog #12-348) visualized using an enhanced chemiluminescence (ECL) solution (Cumaric acid, Luminol and hydrogen peroxide), developed in a LiCore imager. See FIG. 1A.

1-6) PCSK9 Transcription

To study whether 34 affect PCSK9 mRNA levels we used $1 \times 10^6$ HepG2 cells in 6-well culture plates, followed by incubation with media+0.1% DMSO or increasing concentration (0.2-50 µM) of 34 in 0.1% DMSO for 24 hours. After 24 hours media was aspirated, cells were washed with HBSS followed by RNA extraction kit (RNeasy, QIAGEN cat #74-104). mRNA was reversed transcribed to cDNA using commercially available kit (ThermoFisher, cat #4368814) and analyzed using real-time PCR for PCSK9 transcript levels using the relative expression method known as delta-delta CT. See FIG. 1B.

1-7) LDLR Levels

To study whether 34 affect LDLR levels we used $1 \times 10^6$ HepG2 cells in 6-well culture plates, followed by incubation with media+0.1% DMSO or 5 µm of 31/33/34/35 for 24 hours. After 24 hours media was aspirated, cells were washed with HBSS followed by protein extraction using commercially available RIPA buffer (SIGMA-ALDRICH, catalog #20-188). Protein extracts (IMO were used for immunodetection of intracellular LDLR (western blot analysis) with a commercially available primary antibody against LDLR (ABCAM, catalog #14056), HRP-conjugated secondary antibody (ABCAM, catalog #97135) visualized using an enhanced chemiluminescence (ECL) solution (Cumaric acid, Luminol and hydrogen peroxide), developed in a LiCore imager. See FIG. 3.

1-8) Albumin Secretion

Figure 6A:
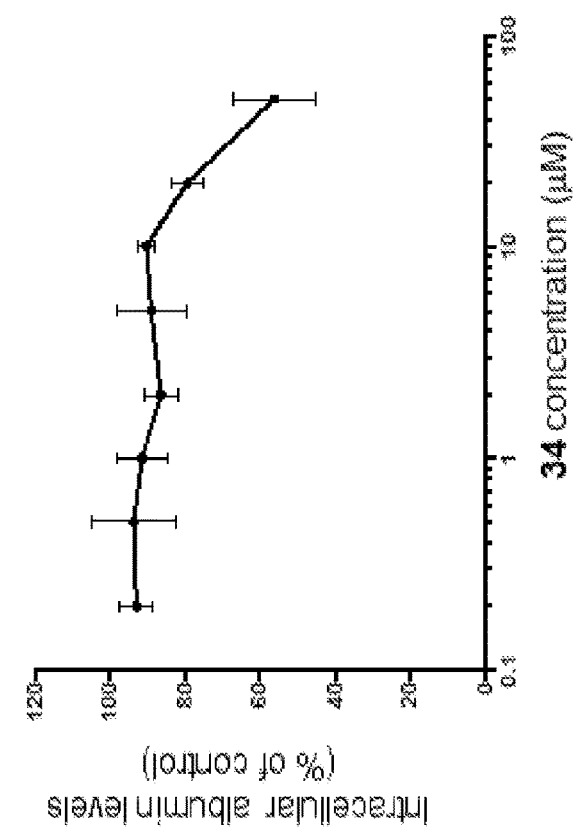
FIGS. 6A-6B show that up to 10 µM of compound 34 does not does not affect albumin level in HepG2 cells. After 40 hours of incubation with up to 10 µM of compound 34 there were no changes in secreted or intracellular albumin.

To study the effect of 34 on albumin secretion we used $1 \times 10^6$ HepG2 cells in 6-well culture plates, followed by incubation with media+0.1% DMSO or with increasing concentration (0.2-50 µM) of 34 in 0.1% DMSO for 24 hours and collection of 500 µl of media. The collected media was analyzed for albumin levels using commercially available ELISA kit (ABCAM, catalog #108788) following the manufacturer instruction. See FIG. 6A.

1-9) Intracellular Albumin

Figure 6B:
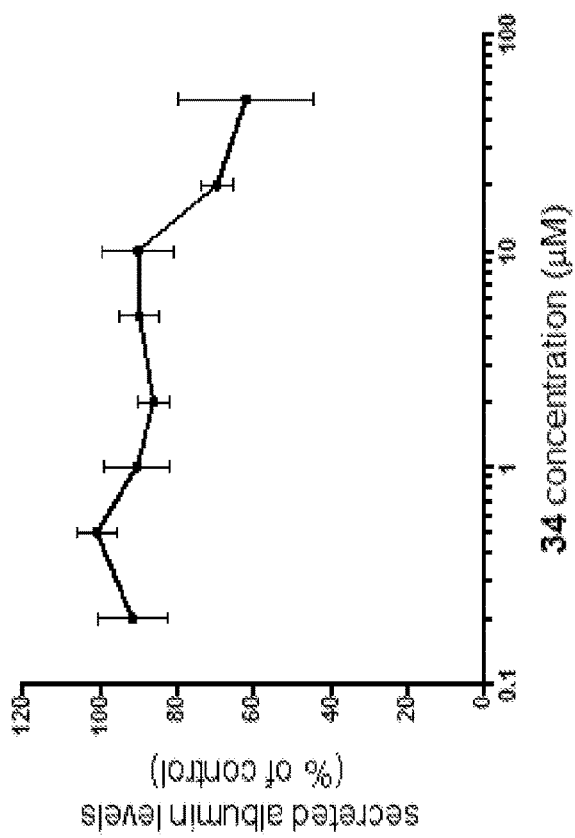

To study whether 34 affect intracellular albumin levels we used 1×10$^6$ HepG2 cells in 6-well culture plates, followed by incubation with media+0.1% DMSO or with increasing concentration (0.2-50 µM) of 34 in 0.1% DMSO for 24 hours. After 24 hours media was aspirated, cells were washed with HBSS followed by protein extraction using commercially available RIPA buffer (SIGMA-ALDRICH, catalog #20-188). Protein extracts (5 µgr) were used for albumin detection using commercially available ELISA kit (ABCAM, catalog #108788) following the manufacturer instruction. See FIG. 6B.

1-10) apoE Secretion

Figure 7A:
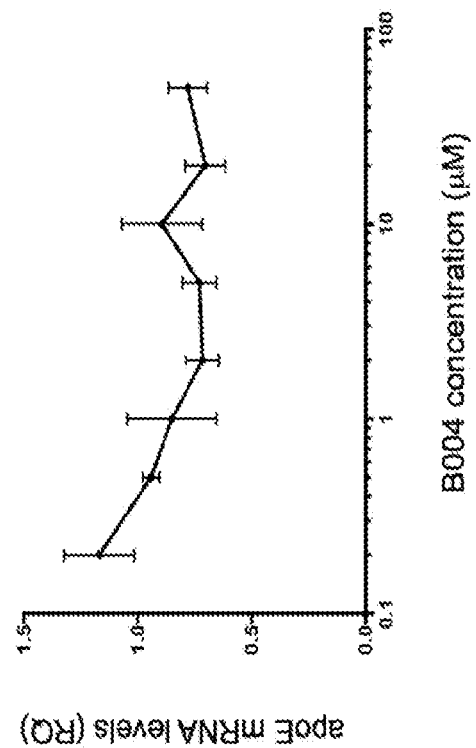
FIGS. 7A-7C show that compound 34 does not does not affect apoE level in HepG2 cells. After 40 hours of incubation with compound 34 there were no changes in secreted, intracellular, or mRNA levels of apoE.

To study the effect of 34 on apoE secretion we used 1×10$^6$ HepG2 cells in 6-well culture plates, followed by incubation with media+0.1% DMSO or with increasing concentration (0.2-50 uM) of 34 in 0.1% DMSO for 24 hours and collection of 50 µl of media. The collected media was analyzed for apoE levels using commercially available ELISA kit (ABCAM, catalog #108813) following the manufacturer instruction. See FIG. 7A.

1-11) Intracellular apoE

Figure 7B:
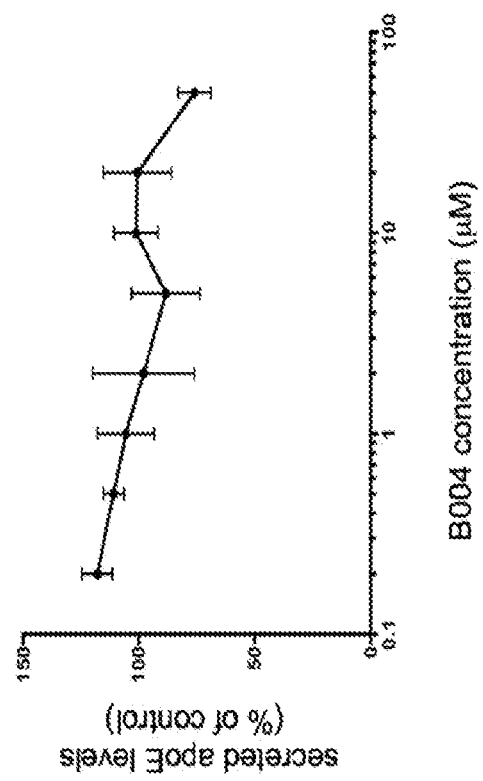
Figure 7C:
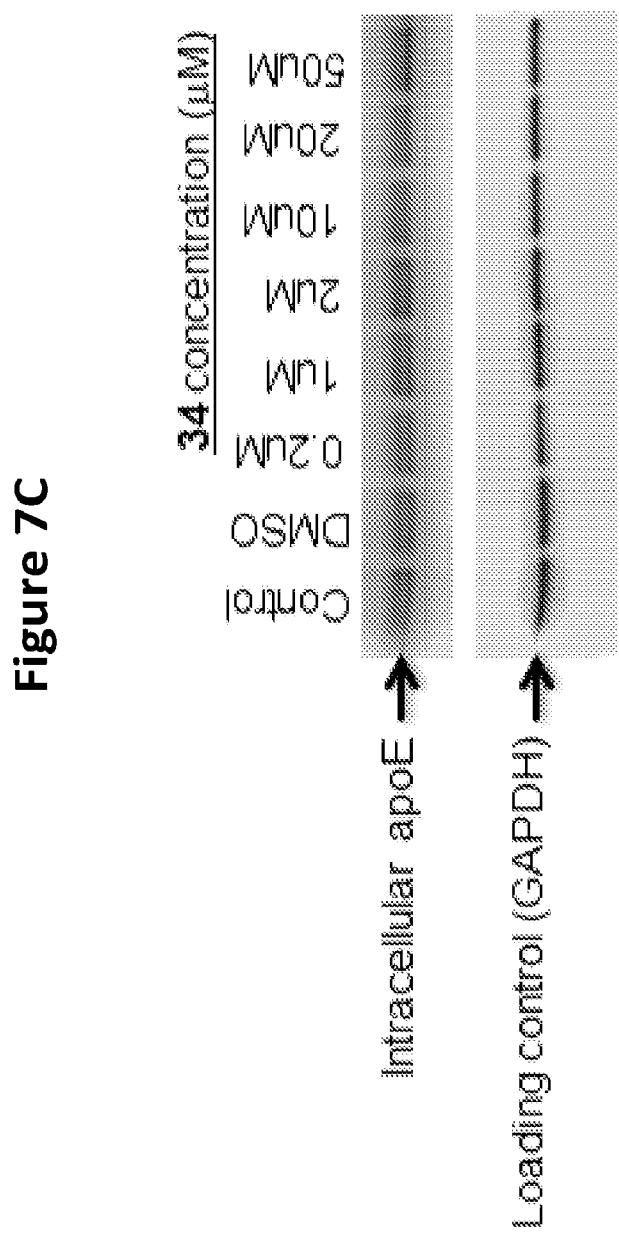

To study whether 34 affect intracellular apoE levels we used 1×10$^6$ HepG2 cells in 6-well culture plates, followed by incubation with media+0.1% DMSO or DMSO or with increasing concentration (0.2-50 µM) of 34 in 0.1% DMSO for 24 hours. After 24 hours media was aspirated, cells were washed with HBSS followed by protein extraction using commercially available RIPA buffer (SIGMA-ALDRICH, catalog #20-188). Protein extracts (25 µgr) were used for immunodetection of intracellular LDLR (western blot analysis) with a commercially available primary antibody against apoE (ABCAM, catalog #1906), HRP-conjugated secondary antibody (SIGMA-ALDRIC, catalog # A5420) visualized using an enhanced chemiluminescence (ECL) solution (Cumaric acid, Luminol and hydrogen peroxide), developed in a LiCore imager. See FIG. 7C.

1-12) apoE Transcription

To study whether 34 affect apoE transcription we used 1×10$^6$ HepG2 cells in 6-well culture plates, followed by incubation with media+0.1% DMSO or DMSO or with increasing concentration (0.2-50 µM) of 34 in 0.1% DMSO for 24 hours. After 24 hours media was aspirated, cells were washed with HBSS followed by RNA extraction kit (RNeasy, QIAGEN cat #74-104). mRNA was reversed transcribed to cDNA using commercially available kit (ThermoFisher, cat #4368814) and analyzed using real-time PCR for apoE transcript levels using the relative expression method known as delta-delta CT. See FIG. 7B.

1-13) Proteomics

Figure 8B:
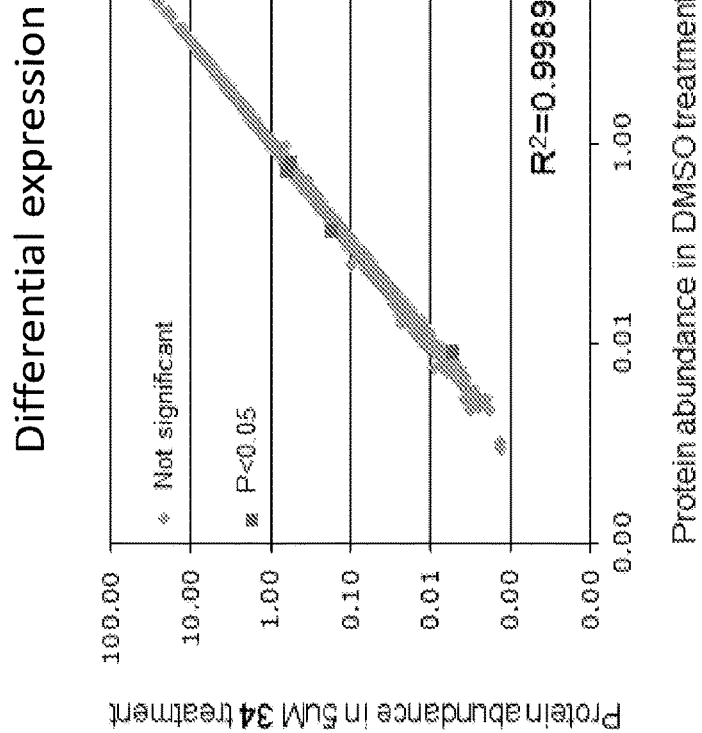
FIGS. 8A-8B show that compound 34 does not affect expression of other proteins in HepG2 cells. Incubation with 5 µM of compound 34 does not affect the levels of the 4000 most abundant proteins in HepG2 cells.
Figure 8A:
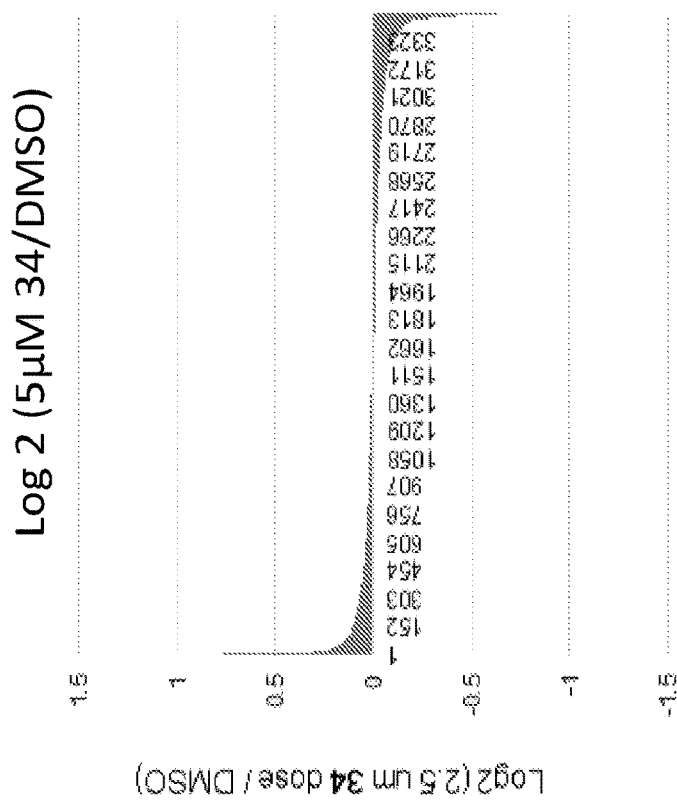
Figure 9:
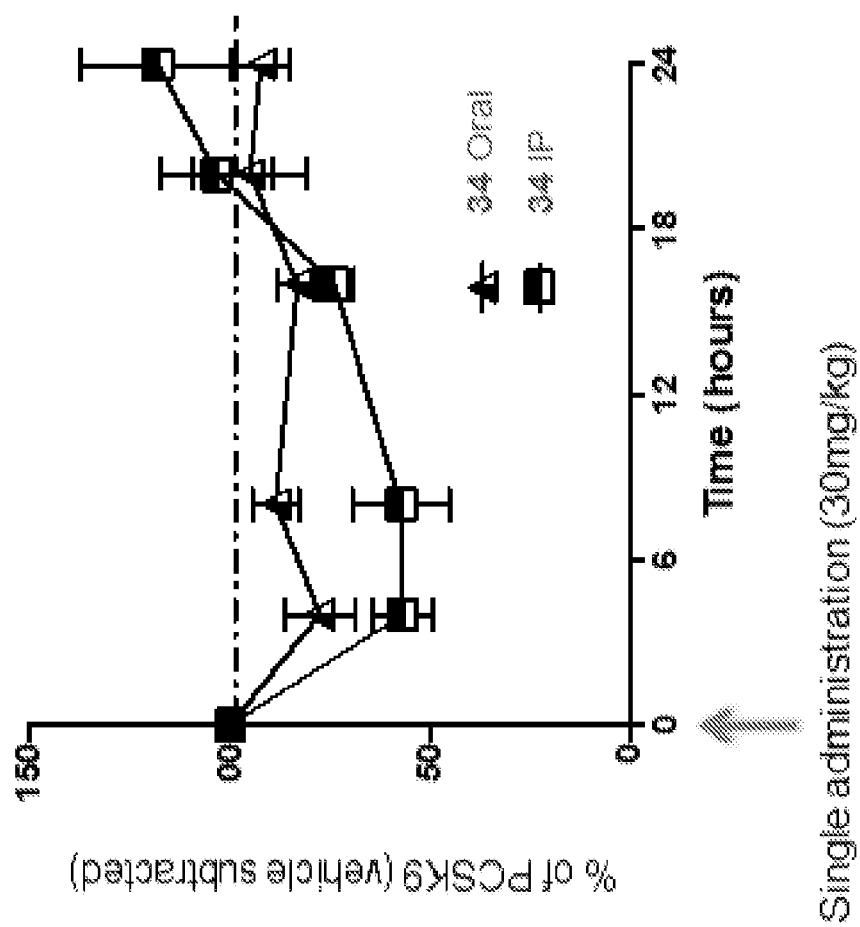
FIG. 9 show that a single administration of 30 mg/kg of compound 34 reduces plasma PCSK9 levels in mice in a time-dependent manner. The maximal drop in PCSK9 was 43.2% with intraperitoneal (IP) injection, and 22.5% with oral gavage (Oral), 4 hours after administration, with levels getting back to baseline after 20 hours after administration. N=2/group.
Figure 10A:
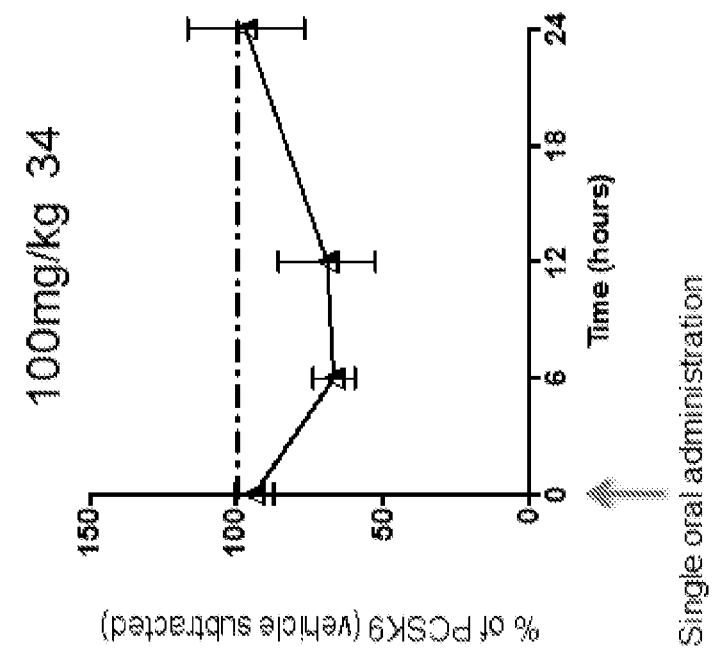
FIGS. 10A-10B show that a single administration of compound 34 reduces plasma PCSK9 levels in a time-dependent and dose-dependent manner in mice.
Figure 10B:
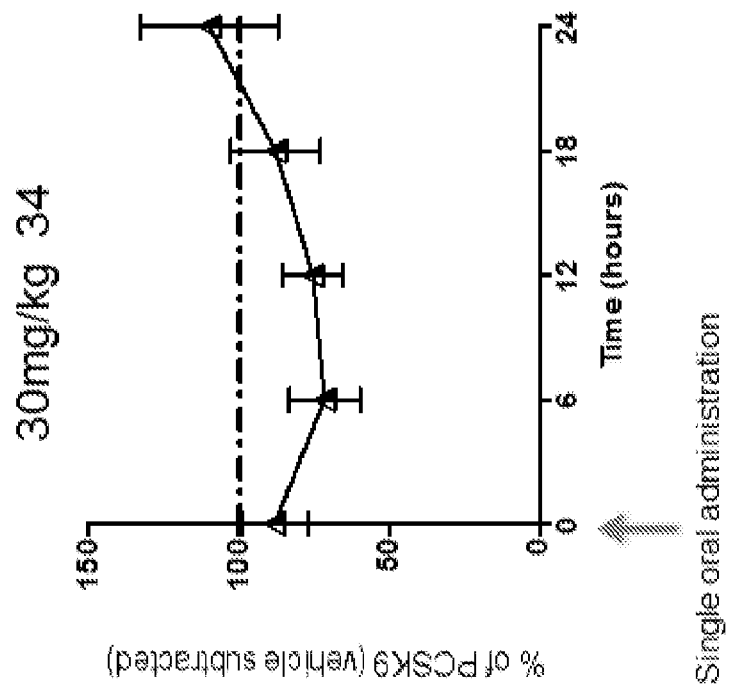

To study whether 34 affect total protein levels in hepG2 in an unbiased analysis we used 1×106 HepG2 cells in 6-well culture plates, followed by incubation with media+ 0.1% DMSO or DMSO or with increasing concentration (2.5-10 µM) of 34 in 0.1% DMSO for 24 hours. After 24 hours media was aspirated, cells were washed with HBSS followed by shotgun proteomics analysis of the most abundant ~4000 cellular proteins. Spectral count for each protein was compared between untreated (0.1% DMSO) to treated (34 at 5 µM) samples. See FIGS. 8A-B.

Example 2

In Vivo Studies Mice

1) Single-dose experiments: mice were administered (oral gavage or intra-peritoneal injection) with 200 µl of 34 (30 mg/kg or 100 mg/kg) in 0.1% Tween 80+1% hydroxyethyl cellulose (HEC) in buffered (PBS pH7.4) solution. After 34 administration, 50-70 µl of blood was collected from the retro-orbital plexus every 4-6 hours (for a total of 24 hours). Blood was left to clot at room temperature for 20 min, followed by serum separation (spin at 1000 g for 10 min). Serum was analyzed as specified in the "Serum analyses" section.

2) Daily dosage experiments: mice were administered daily oral gavage with 200 µl of 34 (100 mg/kg) in 0.1% Tween80+1% hydroxyethyl cellulose (HEC) in buffered (PBS pH7.4) solution. 50-70 µl of blood was collected from the retro-orbital plexus on day 3 and day 5 after 34 administration, on day 5 mice were euthanized and liver were collected and analyzed as mentioned below under the "Liver analyses" section. Blood was left to clot at room temperature for 20 min, followed by serum separation (spin at 1000 g for 10 min). Serum was analyzed as described below:

Serum Analyses:

PCSK9 levels—using commercially available ELISA kit (MBL-international, catalog # CY-8079) following the manufacturer instruction. See FIGS. 9, 10A-B, 12A-B.

Figure 11B:
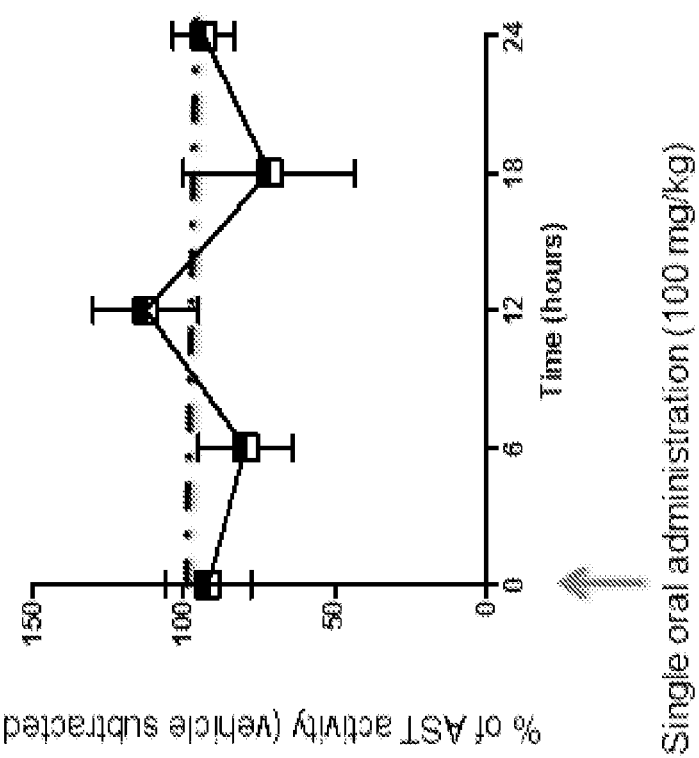
FIGS. 11A-11B show that single oral administration of compound 34 does not affect HDL-cholesterol levels or hepatic transaminase levels in mice.
Figure 11A:
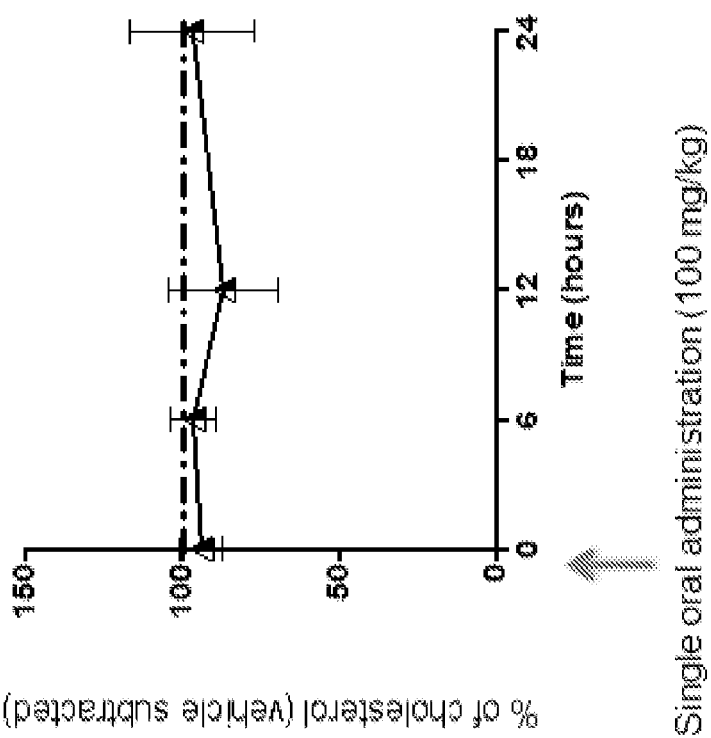
Figure 12B:
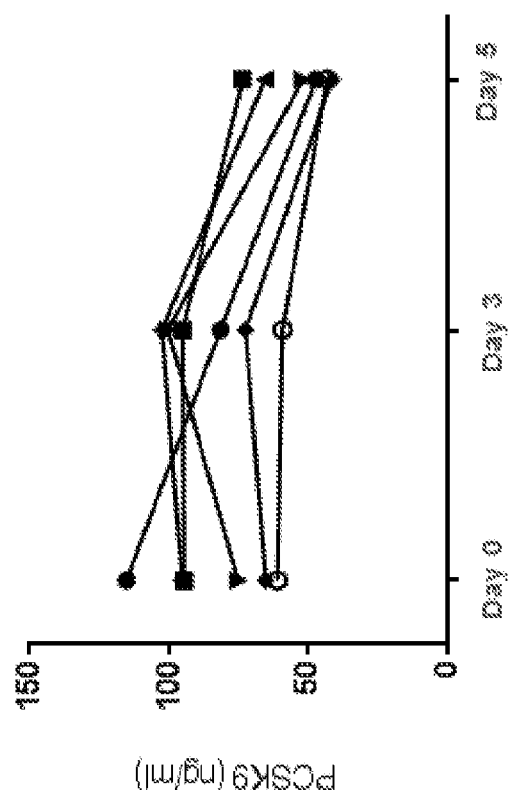
FIGS. 12A-12B show that 5-Day oral administration of compound 34 (100 mg/kg/day) reduces plasma PCSK9 in mice.
Figure 12A:
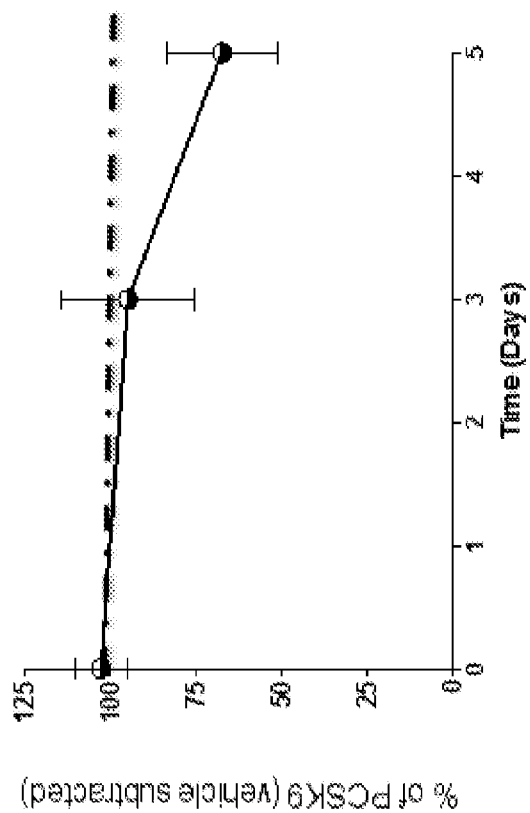
Figure 13B:
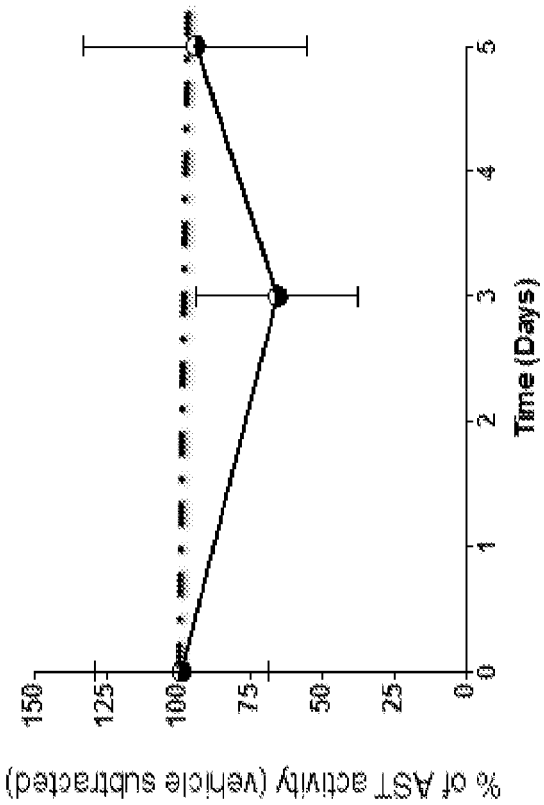
FIGS. 13A-13B show that compound 5-Day oral administration of compound 34 (100 mg/kg/day) does not affect HDL cholesterol levels or hepatic transaminase levels in mice.
Figure 13A:
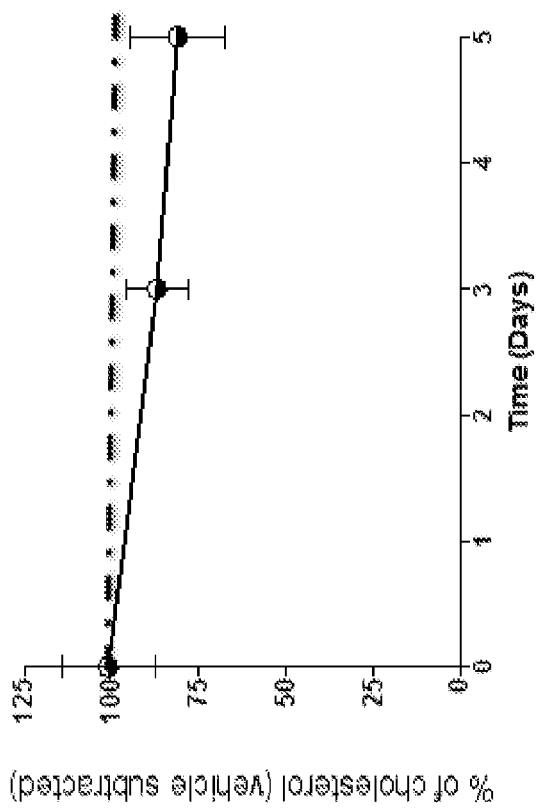

Total cholesterol—using commercially available colorimetric assay (WAKO, catalog #439-17501) following the manufacturer instruction. See FIGS. 11A, 13A.

AST activity—using commercially available activity assay (SIGMA-ALDRICH, catalog # MAK055) following the manufacturer instruction. See FIGS. 11B and 13B.

Figure 14A:
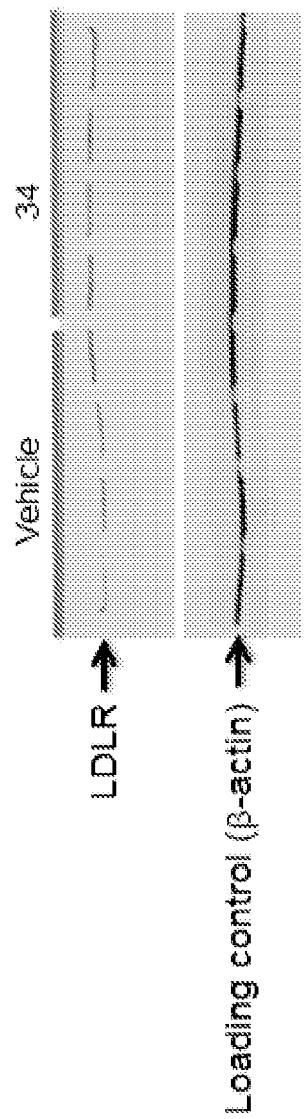
FIGS. 14A-14B show that compound 34 increases hepatic LDLR levels in mice. Livers were collected from mice on day 5 after daily oral administration of 34 (100 mg/kg/day).
Figure 14B:
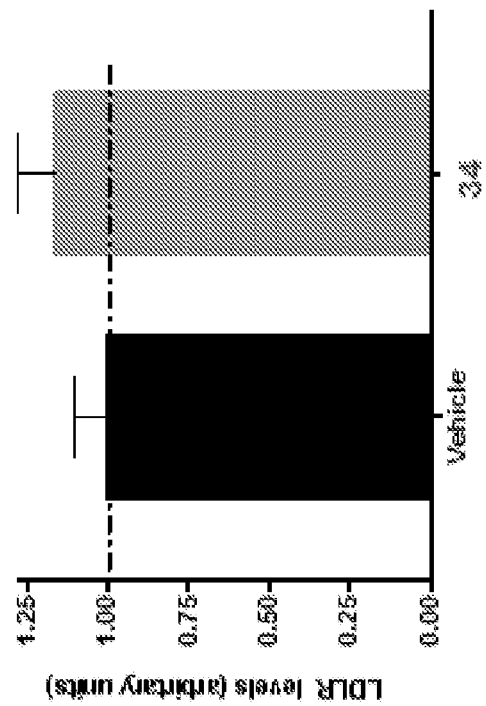

Liver Analyses:

Hepatic LDLR levels—To study whether 34 affect hepatic LDLR levels we used 10 mg of PBS-flushed livers. Livers were minced and proteins were extracted using available RIPA buffer (SIGMA-ALDRICH, catalog #20-188). Protein extracts (5 µgr) were used for immunodetection of intracellular LDLR (western blot analysis) with a commercially available primary antibody against LDLR (ABCAM, catalog #14056), HRP-conjugated secondary antibody (AB-CAM, catalog #97135) visualized using an enhanced chemiluminescence (ECL) solution (Cumaric acid, Luminol and hydrogen peroxide), developed in a LiCore imager. See FIGS. 14A-B.

Figure 15:
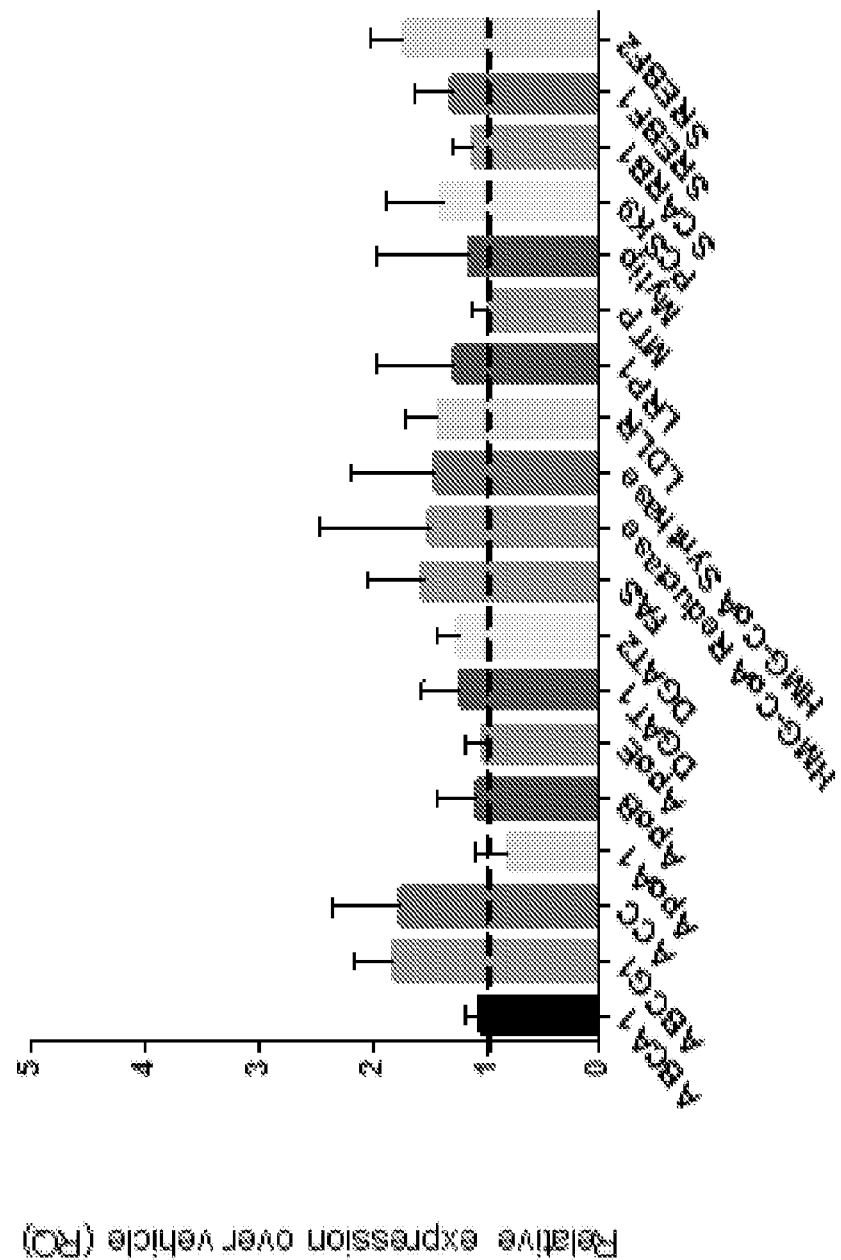
FIG. 15 shows that compound 34 does not affect hepatic expression of lipid-related genes. Livers were collected from mice on day 5 after daily oral administration of 34 (100 mg/kg/day). N=4 mice/treatment groups (vehicle or 34).

Hepatic gene expression—To study whether 34 affect hepatic gene expression we used 10 mg of PBS-flushed livers. Livers were minced followed by RNA extraction kit (RNeasy, QIAGEN cat #74-104). mRNA was reversed transcribed to cDNA using commercially available kit (ThermoFisher, cat #4368814) and analyzed using real-time PCR for transcript levels of the following genes. ABCA1, ABCG1, ACC, apoA1, apoB, apoE, DGAT1, DGAT2, FAS, HMG-CoA reductase, HMG-CoA synthase, LDLR, LRP1, MTP, Mylip, PCSK9, SCARB1, SREBF1 and SREBF2. Gene expression was measured using expression method known as delta-delta CT. See FIG. 15.

Figure 16:
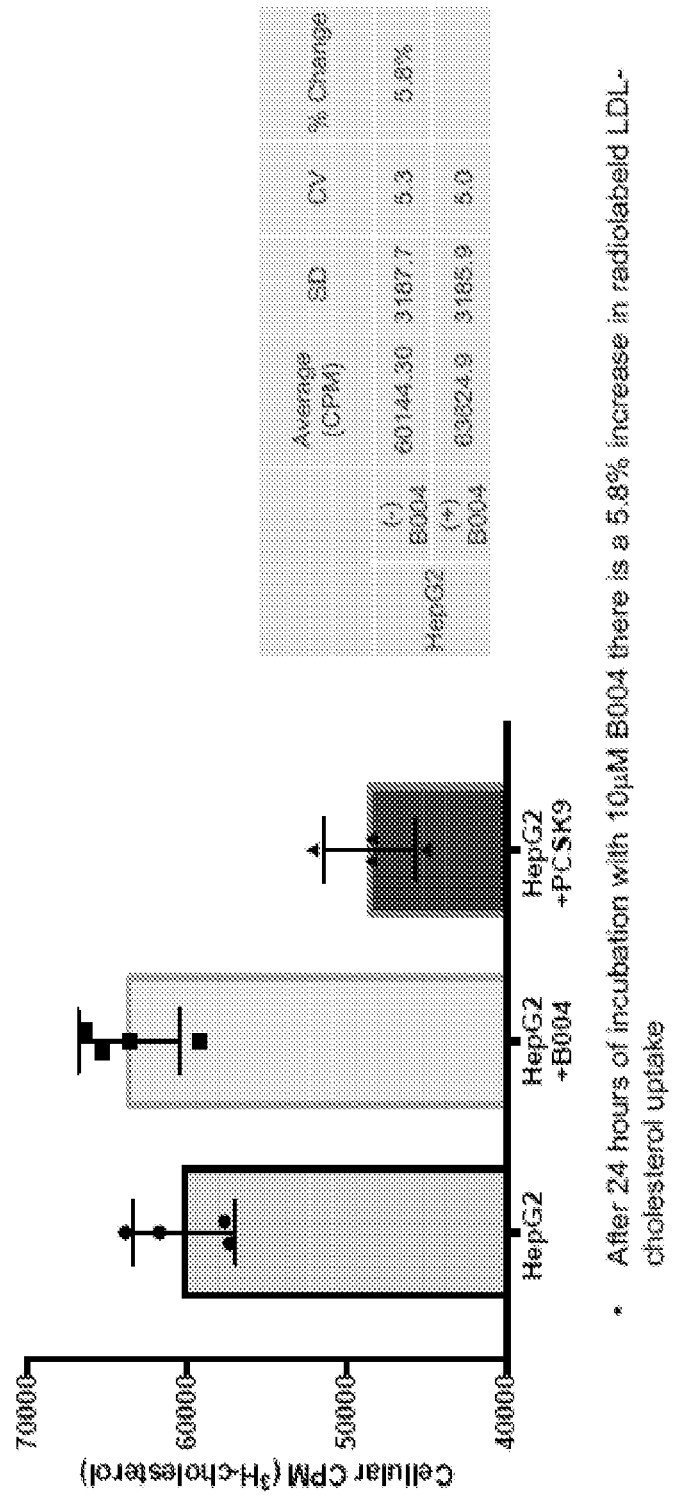
FIG. 16 shows that Compound 34 increases LDL-cholesterol uptake in HepG2 cells.

To determine whether Compound 34 increases LDL-cholesterol uptake, LDL was isolated from human plasma using ultracentrifugation and the cholesterol content of the particle was radiolabeled with 3H-cholesterol. Hepatoma cells (HepG2) were cultured (0.25×10$^6$ cell/well in a 24-well plate) with or without 10 uM of B004 (compound 34) for 24 hours in DMEM. Radiolabeled LDL-cholesterol (LDL-c) was added to the cells for 4 hours. Cells were washed 3 times with PBS and left to air dry. 500 µl of isopropanol was added to each well and incubate with shaking at room temperature for 3 hours in a sealed container. 50 µl of the isopropanol was placed into a scintillation vial together with 4.5 ml of scintillation liquid cocktail (Scintiverse BD). 3H-cholesterol levels were read using a beta emission radioactive counter. Results are shown in FIG. 16.

Example 3

The below data (Table 2) was generated using the assays as discussed in Examples 1-2. Blanks mean no testing was performed. Compounds that exhibit >10% inhibition for the single point (SP) assays were active; less than 10% means either weakly active or inactive. Compound 32 is weakly active and compounds 31, 33, 34, 35 are particularly strongly active, although many compounds tested were weakly active. For the SP assays, the higher the number, the higher the inhibition, e.g., the better the activity of the compound. Compounds with a determined IC50 are particularly active, the IC50 values were determined via dose response curve (under the heading CRC which stands for concentration response curve aka dose response curve).

TABLE 2

| Compound | Primary SP Basal_PCSK9 HepG2 SP | | | Primary CRC Basal_PCSK9 | Secondary Basal_PCSK9 ELISA RPH | |
|---|---|---|---|---|---|---|
| | % Inhib @ 2 µM | % Inhib @ 5 µM | % Inhib @ 50 µM | HepG2 IC50 (µM) | % Inhib @ 20 µM | % Inhib @ 100 µM |
| 1 | 0 | | | | | |
| 2 | | 39.51 | | | | |
| 3 | | −0.4577 | | | | |
| 4 | | 11.69 | | | | |
| 5 | | 30.55 | | | | |
| 6 | | −5.193 | | | | |
| 9 | | 21.92 | | | | |
| 10 | | 11.61 | | | | |
| 11 | | 38.95 | | | | |
| 13 | | 18.09 | | | | |
| 14 | 47.9 | | | >50.0 | | |
| 16 | | 9.989 | | | | |
| 17 | | 37.33 | | | | |
| 18 | | 21.64 | | | | |
| 19 | | 7.268 | | | | |
| 20 | | 15.69 | | | | |
| 21 | | 12.18 | | | | |
| 22 | | 77.2 | | | | |
| 24 | | 4.997 | | | | |
| 31 | | 26.2 | 87.5 | 4.115 | 4.269 | 19.03 |
| | | | | | 7.302 | 22.14 |
| | | | | | −6.645 | |
| | | | | | −32.27 | |
| 32 | | 8.8 | 11.9 | | | |
| 33 | | 18.9 | 53.4 | 2.121 | −4.143 | 25.95 |
| | | | | | 2.541 | 29.77 |
| | | | | | 3.284 | |
| | | | | | −5.595 | |
| 34 | | 5.2 | 100.1 | 3.501 | | |
| 35 | | 26.4 | 90 | 3.141 | | |
| 36 | | 24.5 | 96.5 | 18.57 | | |
| 43 | | | −1.9 | | | |
| | | | −109.9 | | | |
| 44 | | | −32.0 | | | |
| | | | 6.1 | | | |
| 45 | | | −0.4 | | | |
| | | | −14.2 | | | |
| 46 | | | −47.3 | | | |
| | | | 10.3 | | | |
| 47 | | | −3.9 | | | |
| | | | −29.5 | | | |
| 48 | | | −7.0 | | | |
| | | | 43.7 | | | |
| 49 | | | −13.7 | | | |
| | | | −22.9 | | | |
| 50 | | | −12.3 | | | |
| | | | 2.3 | | | |
| 51 | | | −13.1 | | | |
| | | | 0.2 | | | |
| 52 | | | −20.3 | | | |
| | | | −17.9 | | | |
| 53 | | | −20.1 | | | |
| | | | −22.3 | | | |

TABLE 3
| Compound | Primary SP PCSK9 AlphaLisa Huh7 SP | | | | Primary CRC PCSK9 AlphaLisa |
|---|---|---|---|---|---|
| | % Inhib @ 10.1 μM | % Inhib @ 10 μM | % Inhib @ 5 μM | inhib @ 5 μM | Huh7 CRC Rel IC50 |
| 54 | | −11.97 | | | |
| 55 | | −22.6 | | | |
| 56 | | 23.45 | | | |
| | | 32.56 | | | |
| 57 | | 17.71 | | | |
| 58 | | −2.718 | | | |
| 59 | −5.307 | | | | |
| 60 | | 9.09 | | | |
| 61 | | −16.91 | | | |
| 62 | | 10.55 | | | |
| | | 20.08 | | | |
| 7 | | −34.71 | | | |
| 8 | | −44.02 | | | |
| 12 | | −261.1 | | | |
| 14 | | | | −0.3249 | |
| 15 | | −117.8 | | | |
| 22 | | | | 44.69 | >40.0 |
| | | | | | >40.0 |
| 23 | | −35.06 | | | |
| 25 | | −334 | | | |
| 26 | | | | −19.62 | |
| 27 | | | | −18.63 | |
| 28 | | | | 13.48 | |
| 29 | | | | 36.17 | |
| 30 | | | | −33.06 | |
| 31 | | | | 15.65 | |
| 33 | | | | 30.51 | |
| 34 | | | 14.55 | | |
| 36 | | | 12.75 | | |
| 37 | | | | 26.88 | |
| 38 | | | 16.56 | | |
| 39 | | | | −2.219 | |
| 40 | | | | −60.29 | |
| 41 | | | | −0.1365 | |
| 42 | | | | 6.969 | |
| 48 | | | | 20.5 | |
The invention claimed is:
1. A method for reducing the PCSK9 level in a subject, the method comprising administering to the subject an effective amount of a compound selected from a group consisting of:
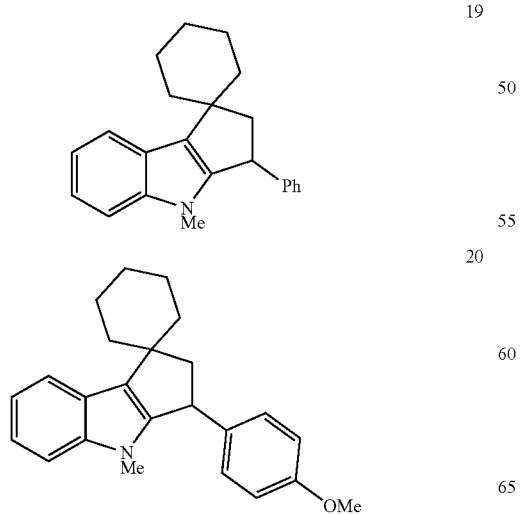
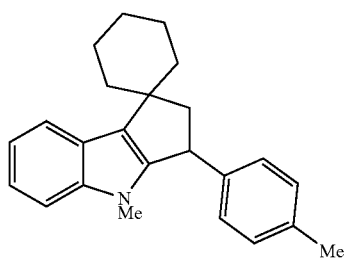
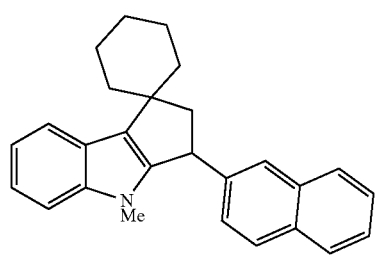

-continued

32
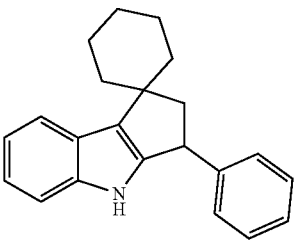

33
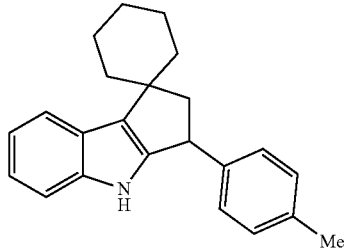

34
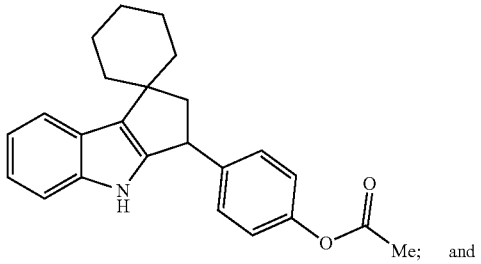

35
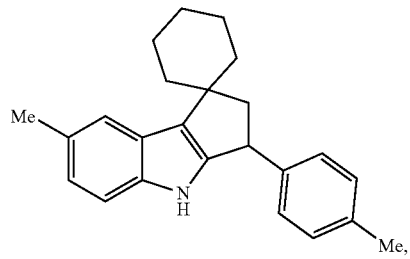

or a pharmaceutically acceptable stereoisomer, isotope, solvate or salt thereof, wherein the subject has a condition associated with an elevated level of PCSK9.

2. The method of claim 1, wherein the PCSK9 level is reduced by at least 10%, 20%, 30%, 40%, 50%, 60%, 70%, or 80% compared to the PCSK9 level in the subject prior to administering the compound of Formula II.

3. The method of claim 1, wherein the levels of both the pro-protein and mature forms of PCSK9 are reduced.

4. The method claim 1, wherein the secretion or production of PCSK9 is inhibited.

5. The method of claim 1, wherein the level of low density lipoprotein receptor (LDLR) in the subject is increased.

6. The method of claim 1 , wherein the amount of low density lipoprotein (LDL) in the cell is decreased.

7. The method of claim 1, wherein the compound is:

34
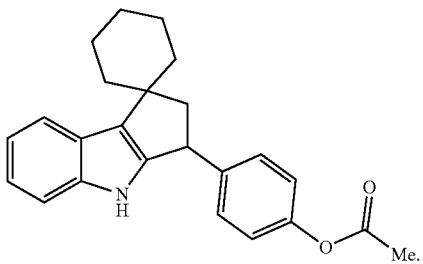

8. The method of claim 1, wherein the condition is selected from the group consisting of hypercholesterolemia, hyperlipidemia, dyslipidemia, metabolic syndrome, a diabetic condition, heart disease, cardiovascular disease, an atherosclerotic disease, stroke and Alzheimer's disease.

* * * * *